United States Patent
Stewart et al.

(10) Patent No.: US 7,736,851 B2
(45) Date of Patent: *Jun. 15, 2010

(54) DNA CLONING METHOD

(75) Inventors: Francis Stewart, Leimen (DE);
Youming Zhang, Heidelberg (DE);
Frank Buchholz, Bremen (DE)

(73) Assignee: Europaisches Laboratorium fur Molekularbiologie (EMBL), Heidelberg (DE)

( * ) Notice: Subject to any disclaimer, the term of this patent is extended or adjusted under 35 U.S.C. 154(b) by 611 days.

This patent is subject to a terminal disclaimer.

(21) Appl. No.: 10/842,534

(22) Filed: May 11, 2004

(65) Prior Publication Data

US 2004/0203057 A1    Oct. 14, 2004

Related U.S. Application Data

(62) Division of application No. 10/231,013, filed on Aug. 30, 2002, now Pat. No. 6,787,316, which is a division of application No. 09/555,510, filed as application No. PCT/EP98/07945 on Dec. 7, 1998, now Pat. No. 6,509,156.

(30) Foreign Application Priority Data

Dec. 5, 1997  (EP)  ................................. 97121462
Oct. 5, 1998  (EP)  ................................. 98118756

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/24.3

(58) Field of Classification Search ........................ None
See application file for complete search history.

(56) References Cited

U.S. PATENT DOCUMENTS 6,509,156 B1 *  1/2003  Stewart et al. .................. 435/6
6,787,316 B2 *  9/2004  Stewart et al. .................. 435/6

FOREIGN PATENT DOCUMENTS

WO    WO 95/22625    8/1995

OTHER PUBLICATIONS

Murphy, K.C., "Use of Bacteriophage Lambda Recombination Functions to Promote Gene Replacement in *Escherichia coli*", J. Bacter., vol. 180, pp. 2063-2071 (1998).*
Takahashi et al., PNAS USA, vol. 87, pp. 2790-2794 (1990).*
Nussbaum, A. and Cohen A., Use of Bioluminescence Gene Reporter for the Investigation of Red-dependent and Gam-dependent Plasmid Recombination in *Escherichia coli* K12, J. Mol. Biol., vol. 203, pp. 391-402 (1988).*

(Continued)

*Primary Examiner*—Teresa E Strzelecka
(74) *Attorney, Agent, or Firm*—Rothwell, Figg, Ernst & Manbeck, P.C.

(57) ABSTRACT

The invention relates to methods for cloning DNA molecules using recE/recT-mediated homologous recombination mechanism between at least two DNA molecules where one DNA molecule is a circular or linear DNA molecule and the second DNA molecule is a circular DNA molecule, and the second DNA molecule contains two regions with sequence homology to the first DNA molecule. Competent cells and vectors are also described.

24 Claims, 65 Drawing Sheets

OTHER PUBLICATIONS

Figure 1:
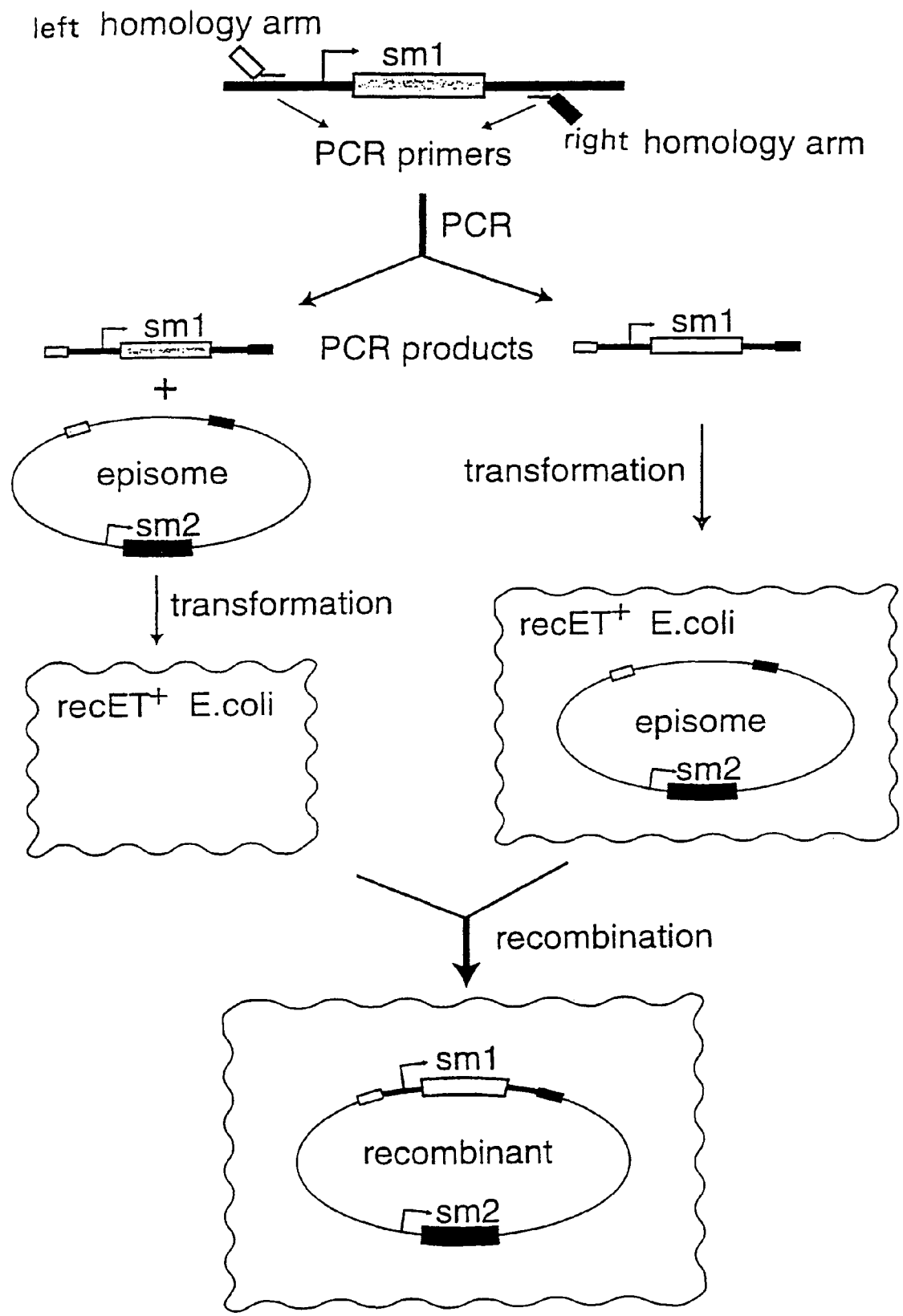

Nussbaum A. et al., Genetics, vol. 130, pp. 37-49 (1992).*

Degryse et al., "Homologous recombination based modification in *Escherichia coli* and germ line transmission in transgenic mice of a bacterial artificial chromosome", Nature Biotechnology, vol. 15, Sep. 1997, pp. 859-865.

Degryse et al., "Evaluation of *Escherichia coli* recBC sbcBC mutants for cloning by recombination in vivo", Journal of Biotechnology, vol. 2, No. 39, Apr. 15, 1995, pp. 181-187.

GeneBank Accession No. V00638, "Lambda genomes from map unit 74 backward to map unit 67".

Hall, S.D., et al., "Identification and Characterization of the *Escherichia coli* RecT Protein, a Protein Encoded by the recE Region That Promotes Denaturation of Homologous Single-Stranded DNA", Journal of Bacteriology, Washington, D.C., vol. 175, No. 1, Jan. 1993, p. 277-287.

Hall, D.S. et al., "Homologous Pairing and strand exchange promoted by the *Escherichia coli* RecT protein", PNAS USA, vol. 91, pp. 3205-3209 (1994).

Kolodner et al., "homologous pairing proteins encloded by the *Escherichia coli* recE and recT genes" Molecular Microbiology, vol. 11, No. 1, 1994, pp. 23-30.

Luisi-Deluca et al., "Genetic and physical analysis of plasmid recombination in recB recC sbcB and recB recC sbcA *Escherichia coli* K-12 mutants", Genetics, vol. 122, 1989, pp. 269-278.

Murphy, "Lambda Gam protein inhibits the helicase and Chi-stimulated recombination activities of *Escherichia coli* RecBCD enzyme," Journal of Bacteriology, vol. 173, No. 18, Sep. 1991, pp. 5808-5821.

Nussbaum et al., "Restrictuion-stimulated homologous recombination of plasmids by the RecE pathway of *Escherichia coli*", Genetics, vol. 130, No. 1, Jan. 1992, pp. 37-49.

Oliner et al., "In vivo cloning of PCR Products in *E. coli*", Nucleic Acids Research, vol. 21, No. 22, pp. 5192-5197 (1993).

Stratagene Catalog, p. 39 (1988).

A. Clark, et al.: "Genetic and Molecular Analyses of the C-Terminal Region of the recE Gene from the Rac Prophage of *Escherichia coli* K-12 Reveal the recT Gene," J. Bacteriol., vol. 175, No. 23, pp. 7673-7682, Dec. 1993.

NCBI Accession No. M24905.1, Search Pages, 2 pages.

NCBI Accession No. L23927.1, Search Pages, 3 pages.

NCBI Accession No. J02459 M17233 M24325 V00636 00906, Search Pages, 37 pages.

TaKaRa Biotechnology Guide: "Guide Genetic Engineering Research," pp. 163-169, 1994-1995.

B. Sauer, et al.: "Site-specific DNA recombination in mammalian cells by the Cre recombinase of bacteriophage P1," Proc. Natl. Acad. Sci. USA, vol. 85, pp. 5166-5170, Jul. 1988.

Y. Sakaki, et al.: "Purification and Properties of the γ-Protein Specified by Bacteriophage λ: An Inhibitor of the Host RecBC Recombination Enzyme," Proc. Nat. Acad. Sci. USA, vol. 70, No. 8, pp. 2215-2219, Aug. 1973.

A. Poteete, et al.: "Activation of RecF-Dependent Recombination in *Escherichia coli* by Bacteriophage λ- and P22-Encoded Functions," J. Bacteriol., vol. 170, No. 9, pp. 4379-4381, Sep. 1988.

A. Poteete, et al.: "Modulation of *Escherichia coli* RecBCD Activity by the Bacteriophage λ Gam and P22 Abc Functions," J. Bacteriol., vol. 171, No. 5, pp. 2012-2021, May 1988.

M. Behme, et al.: "Postinfection Control by Bacteriophage T4 of *Escherichia coli* recBC Nuclease Activity," J. Virol., vol. 18, No. 1, pp. 20-25, Apr. 1976.

K. Murphy, et al.: "Properties of *Escherichia coli* Expressing Bacteriophage P22 Abc (Anti-RecBCD) Proteins, Including Inhibition of Chi Activity," J. Bacteriol., vol. 175, No. 6, pp. 1756-1766, Mar. 1993.

* cited by examiner

*a*

*b*

| P1 DNA digested with EcoR I | hybridized with a bla probe (Amp) | hybridized with a Hoxa-3 probe |

Lane 1:    1 of P1-Hox clone in NS3145 original bacterial strain (Kan resistance)

Lane 2-3:  2 of P1-Hox clones in JC9604 before homologous recombination (Kan resistance)

Lane 4-6:  3 of P1-Hox clones in JC9604 after homologous recombination (Amp resistance)

*a*

*b* pZero-2.1 alone pZero-2.1 + PCR products

IPTG + Kan t-recE --- truncated recE (from 588 aa ---> end. 866 aa)

Figure 7b

```
  1 ATCGATGCATAATGTGCCTGTCAAATGGACGAAGCAGGGATTC
 44 TGCAAACCCTATGCTACTCCGTCAAGCCGTCAATTGTCTGATT
 87 CGTTACCAA TTA TGA CAA CTT GAC GGC TAC ATC
          293◄• • • Ser Leu Lys Val Ala Val Asp
120 ATT CAC TTT TTC TTC ACA ACC GGC ACG GAA CTC
285◄Asn Val Lys Glu Glu Cys Gly Ala Arg Phe Glu
153 GCT CGG GCT GGC CCC GGT GCA TTT TTT AAA TAC
274◄Ser Pro Ser Ala Gly Thr Cys Lys Lys Phe Val
186 CCG CGA GAA ATA GAG TTG ATC GTC AAA ACC AAC
263◄Arg Ser Phe Tyr Leu Gln Asp Asp Phe Gly Val
219 ATT GCG ACC GAC GGT GGC GAT AGG CAT CCG GGT
252◄Asn Arg Gly Val Thr Ala Ile Pro Met Arg Thr
252 GGT GCT CAA AAG CAG CTT CGC CTG GCT GAT ACG
241◄Thr Ser Leu Leu Leu Lys Ala Gln Ser Ile Arg
285 TTG GTC CTC GCG CCA GCT TAA GAC GCT AAT CCC
230◄Gln Asp Glu Arg Trp Ser Leu Val Ser Ile Gly
318 TAA CTG CTG GCG GAA AAG ATG TGA CAG ACG CGA
219◄Leu Gln Gln Arg Phe Leu His Ser Leu Arg Ser
351 CGG CGA CAA GCA AAC ATG CTG TGC GAC GCT GGC
208◄Pro Ser Leu Cys Val His Gln Ala Val Ser Ala
    EcoRV
384 GAT ATC AAA ATT GCT GTC TGC CAG GTG ATC GCT
197◄Ile Asp Phe Asn Ser Asp Ala Leu His Asp Ser
417 GAT GTA CTG ACA AGC CTC GCG TAC CCG ATT ATC
186◄Ile Tyr Gln Cys Ala Glu Arg Val Arg Asn Asp
```

Figure 7b (cont'd)

```
450 CAT CGG TGG ATG GAG CGA CTC GTT AAT CGC TTC
175◀Met Pro Pro His Leu Ser Glu Asn Ile Ala Glu

483 CAT GCG CCG CAG TAA CAA TTG CTC AAG CAG ATT
164◀Met Arg Arg Leu Leu Leu Gln Glu Leu Leu Asn

516 TAT CGC CAG CAG CTC CGA ATA GCG CCC TTC CCC
153◀Ile Ala Leu Leu Glu Ser Tyr Arg Gly Glu Gly

549 TTG CCC GGC GTT AAT GAT TTG CCC AAA CAG GTC
142◀Gln Gly Ala Asn Ile Ile Gln Gly Phe Leu Asp

582 GCT GAA ATG CGG CTG GTG CGC TTC ATC CGG GCG
131◀Ser Phe His Pro Gln His Ala Glu Asp Pro Arg

615 AAA GAA CCC CGT ATT GGC AAA TAT TGA CGG CCA
120◀Phe Phe Gly Thr Asn Ala Phe Ile Ser Pro Trp

648 GTT AAG CCA TTC ATG CCA GTA GGC GCG CGG ACG
109◀Asn Leu Trp Glu His Trp Tyr Ala Arg Pro Arg

681 AAA GTA AAC CCA CTG GTG ATA CCA TTC GCG AGC
98◀Phe Tyr Val Trp Gln His Tyr Trp Glu Arg Ala

714 CTC CGG ATG ACG ACC GTA GTG ATG AAT CTC TCC
87◀Glu Pro His Arg Gly Tyr His His Ile Glu Gly

747 TGG CGG GAA CAG CAA AAT ATC ACC CGG TCG GCA
76◀Pro Pro Phe Leu Leu Ile Asp Gly Pro Arg Cys

780 AAC AAA TTC TCG TCC CTG ATT TTT CAC CAC CCC
65◀Val Phe Glu Arg Gly Gln Asn Lys Val Val Gly

813 CTG ACC GCG AAT GGT GAG ATT GAG AAT ATA ACC
54◀Gln Gly Arg Ile Thr Leu Asn Leu Ile Tyr Gly

846 TTT CAT TCC CAG CGG TCG GTC GAT AAA AAA ATC
43◀Lys Met Gly Leu Pro Arg Asp Ile Phe Phe Asp
```

Figure 7b (cont'd)

```
 879 GAG ATA ACC GTT GGC CTC AAT CGG CGT TAA ACC
 32◀Leu Tyr Gly Asn Ala Glu Ile Pro Thr Leu Gly
 912 CGC CAC CAG ATG GGC ATT AAA CGA GTA TCC CGG
 21◀Ala Val Leu His Ala Asn Phe Ser Tyr Gly Pro
 945 CAG CAG GGG ATC ATT TTG CGC TTC AGC CAT
 10◀Leu Leu Pro Asp Asn Gln Ala Glu Ala Met
 975 ACTTTTCATA CTCCCGCCAT TCAGAGAAGA AACCAATTGT
1015 CCATATTGCA TCAGACATTG CCGTCACTGC GTCTTTTACT
1055 GGCTCTTCTC GCTAACCAAA CCGGTAACCC CGCTTATTAA
1095 AAGCATTCTG TAACAAAGCG GGACCAAAGC CATGACAAAA
1135 ACGCGTAACA AAAGTGTCTA TAATCACGGC AGAAAAGTCC
1175 ACATTGATTA TTTGCACGGC GTCACACTTT GCTATGCCAT
                                    BamHI
1215 AGCATTTTTA TCCATAAGAT TAGCGGATCC TACCTGACGC
1255 TTTTTATCGC AACTCTCTAC TGTTTCTCCA TACCCGTTTT
        NheI         EcoRI     NcoI
1295 TTTGGGCTAG CAGGAGGAAT TCACC ATG GAT CCC GTA
                                 1▶Met Asp Pro Val
1332 ATC GTA GAA GAC ATA GAG CCA GGT ATT TAT TAC
  5▶Ile Val Glu Asp Ile Glu Pro Gly Ile Tyr Tyr
1365 GGA ATT TCG AAT GAG AAT TAC CAC GCG GGT CCC
 16▶Gly Ile Ser Asn Glu Asn Tyr His Ala Gly Pro
1398 GGT ATC AGT AAG TCT CAG CTC GAT GAC ATT GCT
```

Figure 7b (cont'd)

```
       27▶ Gly  Ile  Ser  Lys  Ser  Gln  Leu  Asp  Asp  Ile  Ala
      1431  GAT  ACT  CCG  GCA  CTA  TAT  TTG  TGG  CGT  AAA  AAT

38▶ Asp  Thr  Pro  Ala  Leu  Tyr  Leu  Trp  Arg  Lys  Asn
      1464  GCC  CCC  GTG  GAC  ACC  ACA  AAG  ACA  AAA  ACG  CTC

49▶ Ala  Pro  Val  Asp  Thr  Thr  Lys  Thr  Lys  Thr  Leu
      1497  GAT  TTA  GGA  ACT  GCT  TTC  CAC  TGC  CGG  GTA  CTT

60▶ Asp  Leu  Gly  Thr  Ala  Phe  His  Cys  Arg  Val  Leu
                             EcoRI
      1530  GAA  CCG  GAA  GAA  TTC  AGT  AAC  CGC  TTT  ATC  GTA

71▶ Glu  Pro  Glu  Glu  Phe  Ser  Asn  Arg  Phe  Ile  Val
      1563  GCA  CCT  GAA  TTT  AAC  CGC  CGT  ACA  AAC  GCC  GGA

82▶ Ala  Pro  Glu  Phe  Asn  Arg  Arg  Thr  Asn  Ala  Gly
      1596  AAA  GAA  GAA  GAG  AAA  GCG  TTT  CTG  ATG  GAA  TGC

93▶ Lys  Glu  Glu  Glu  Lys  Ala  Phe  Leu  Met  Glu  Cys
      1629  GCA  AGC  ACA  GGA  AAA  ACG  GTT  ATC  ACT  GCG  GAA

104▶ Ala  Ser  Thr  Gly  Lys  Thr  Val  Ile  Thr  Ala  Glu
      1662  GAA  GGC  CGG  AAA  ATT  GAA  CTC  ATG  TAT  CAA  AGC

115▶ Glu  Gly  Arg  Lys  Ile       Leu  Met  Tyr  Gln  Ser
```

Figure 7b (cont'd)

1695 GTT ATG GCT TTG CCG CTG GGG CAA TGG CTT GTT

126▶ Val Met Ala Leu Pro Leu Gly Gln Trp Leu Val

1728 GAA AGC GCC GGA CAC GCT GAA TCA TCA ATT TAC

137▶ Glu Ser Ala Gly His Ala Glu Ser Ser Ile Tyr

1761 TGG GAA GAT CCT GAA ACA GGA ATT TTG TGT CGG

148▶ Trp Glu Asp Pro Glu Thr Gly Ile Leu Cys Arg

1794 TGC CGT CCG GAC AAA ATT ATC CCT GAA TTT CAC

159▶ Cys Arg Pro Asp Lys Ile Ile Pro Glu Phe His

1827 TGG ATC ATG GAC GTG AAA ACT ACG GCG GAT ATT

170▶ Trp Ile Met Asp Val Lys Thr Thr Ala Asp Ile

1860 CAA CGA TTC AAA ACC GCT TAT TAC GAC TAC CGC

181▶ Gln Arg Phe Lys Thr Ala Tyr Tyr Asp Tyr Arg

1893 TAT CAC GTT CAG GAT GCA TTC TAC AGT GAC GGT

192▶ Tyr His Val Gln Asp Ala Phe Tyr Ser Asp Gly

1926 TAT GAA GCA CAG TTT GGA GTG CAG CCA ACT TTC

203▶ Tyr Glu Ala Gln Phe Gly Val Gln Pro Thr Phe

1959 GTT TTT CTG GTT GCC AGC ACA ACT ATT GAA TGC

214▶ Val Phe Leu Val Ala Ser Thr Thr Ile Glu Cys

1992 GGA CGT TAT CCG GTT GAA ATT TTC ATG ATG GGC

Figure 7b (cont'd)

```
225▶ Gly Arg Tyr Pro Val Glu Ile Phe Met Met Gly
2025 GAA GAA GCA AAA CTG GCA GGT CAA CAG GAA TAT

236▶ Glu Glu Ala Lys Leu Ala Gly Gln Gln Glu Tyr
2058 CAC CGC AAT CTG CGA ACC CTG TCT GAC TGC CTG

247▶ His Arg Asn Leu Arg Thr Leu Ser Asp Cys Leu
                          BalI
2091 AAT ACC GAT GAA TGG CCA GCT ATT AAG ACA TTA

258▶ Asn Thr Asp Glu Trp Pro Ala Ile Lys Thr Leu
2124 TCA CTG CCC CGC TGG GCT AAG GAA TAT GCAA

269▶ Ser Leu Pro Arg Trp Ala Lys Glu Tyr AlaA
2155 ATG ACT AAG CAA CCA CCA ATC GCA AAA GCC GAT
  1▶ Met Thr Lys Gln Pro Pro Ile Ala Lys Ala Asp
279▶ s nAs p• • •
2188 CTG CAA AAA ACT CAG GGA AAC CGT GCA CCA GCA
 12▶ Leu Gln Lys Thr Gln Gly Asn Arg Ala Pro Ala
2221 GCA GTT AAA AAT AGC GAC GTG ATT AGT TTT ATT
 23▶ Ala Val Lys Asn Ser Asp Val Ile Ser Phe Ile
2254 AAC CAG CCA TCA ATG AAA GAG CAA CTG GCA GCA
 34▶ Asn Gln Pro Ser Met Lys Glu Gln Leu Ala Ala
                          NdeI
2287 GCT CTT CCA CGC CAT ATG ACG GCT GAA CGT ATG
 45▶ Ala Leu Pro Arg His Met Thr Ala Glu Arg Met
```

Figure 7b (cont'd)

```
2320 ATC CGT ATC GCC ACC ACA GAA ATT CGT AAA GTT
  56▶ Ile Arg Ile Ala Thr Thr Glu Ile Arg Lys Val
2353 CCG GCG TTA GGA AAC TGT GAC ACT ATG AGT TTT
  67▶ Pro Ala Leu Gly Asn Cys Asp Thr Met Ser Phe
2386 GTC AGT GCG ATC GTA CAG TGT TCA CAG CTC GGA
  78▶ Val Ser Ala Ile Val Gln Cys Ser Gln Leu Gly
2419 CTT GAG CCA GGT AGC GCC CTC GGT CAT GCA TAT
  89▶ Leu Glu Pro Gly Ser Ala Leu Gly His Ala Tyr
2452 TTA CTG CCT TTT GGT AAT AAA AAC GAA AAG AGC
 100▶ Leu Leu Pro Phe Gly Asn Lys Asn Glu Lys Ser
2485 GGT AAA AAG AAC GTT CAG CTA ATC ATT GGC TAT
 111▶ Gly Lys Lys Asn Val Gln Leu Ile Ile Gly Tyr
2518 CGC GGC ATG ATT GAT CTG GCT CGC CGT TCT GGT
 122▶ Arg Gly Met Ile Asp Leu Ala Arg Arg Ser Gly
2551 CAA ATC GCC AGC CTG TCA GCC CGT GTT GTC CGT
 133▶ Gln Ile Ala Ser Leu Ser Ala Arg Val Val Arg
2584 GAA GGT GAC GAG TTT AGC TTC GAA TTT GGC CTT
 144▶ Glu Gly Asp Glu Phe Ser Phe Glu Phe Gly Leu
2617 GAT GAA AAG TTA ATA CAC CGC CCG GGA GAA AAC
 155▶ Asp Glu Lys Leu Ile His Arg Pro Gly Glu Asn
2650 GAA GAT GCC CCG GTT ACC CAC GTC TAT GCT GTC
 166▶ Glu Asp Ala Pro Val Thr His Val Tyr Ala Val
2683 GCA AGA CTG AAA GAC GGA GGT ACT CAG TTT GAA
 177▶ Ala Arg Leu Lys Asp Gly Gly Thr Gln Phe Glu
2716 GTT ATG ACG CGC AAA CAG ATT GAG CTG GTG CGC
 188▶ Val Met Thr Arg Lys Gln Ile Glu Leu Val Arg
```

Figure 7b (cont'd)

```
2749  AGC  CTG  AGT  AAA  GCT  GGT  AAT  AAC  GGG  CCG  TGG
199▶  Ser  Leu  Ser  Lys  Ala  Gly  Asn  Asn  Gly  Pro  Trp

2782  GTA  ACT  CAC  TGG  GAA  GAA  ATG  GCA  AAG  AAA  ACG
210▶  Val  Thr  His  Trp  Glu  Glu  Met  Ala  Lys  Lys  Thr

2815  GCT  ATT  CGT  CGC  CTG  TTC  AAA  TAT  TTG  CCC  GTA
221▶  Ala  Ile  Arg  Arg  Leu  Phe  Lys  Tyr  Leu  Pro  Val

2848  TCA  ATT  GAG  ATC  CAG  CGT  GCA  GTA  TCA  ATG  GAT
232▶  Ser  Ile  Glu  Ile  Gln  Arg  Ala  Val  Ser  Met  Asp
                                              PstI

2881  GAA  AAG  GAA  CCA  CTG  ACA  ATC  GAT  CCT  GCA  GAT
243▶  Glu  Lys  Glu  Pro  Leu  Thr  Ile  Asp  Pro  Ala  Asp

2914  TCC  TCT  GTA  TTA  ACC  GGG  GAA  TAC  AGT  GTA  ATC
254▶  Ser  Ser  Val  Leu  Thr  Gly  Glu  Tyr  Ser  Val  Ile
                              BglII     HindIII
2947  GAT  AAT  TCA  GAG  GAA  TAG  ATCTAAGCTT
265▶  Asp  Asn  Ser  Glu  Glu  •••
```

2975 GGCTGTTTTG GCGGATGAGA GAAGATTTTC AGCCTGATAC
3015 AGATTAAATC AGAACGCAGA AGCGGTCTGA TAAAACAGAA
3055 TTTGCCTGGC GGCAGTAGCG CGGTGGTCCC ACCTGACCCC
3095 ATGCCGAACT CAGAAGTGAA ACGCCGTAGC GCCGATGGTA
3135 GTGTGGGGTC TCCCCATGCG AGAGTAGGGA ACTGCCAGGC
3175 ATCAAATAAA ACGAAAGGCT CAGTCGAAAG ACTGGGCCTT
3215 TCGTTTTATC TGTTGTTTGT CGGTGAACGC TCTCCTGAGT
3255 AGGACAAATC CGCCGGGAGC GGATTTGAAC GTTGCGAAGC
3295 AACGGCCCGG AGGGTGGCGG GCAGGACGCC CGCCATAAAC
3335 TGCCAGGCAT CAAATTAAGC AGAAGGCCAT CCTGACGGAT

Figure 7b (cont'd)

```
3375 GGCCTTTTTG CGTTTCTACA AACTCTTTTG TTTATTTTTC
3415 TAAATACATT CAAATATGTA TCCGCTCATG AGACAATAAC
3455 CCTGATAAAT GCTTCAATAA TATTGAAAAA GGAAGAGT AT
                                              1▶ Me
3495  G   AGT  ATT  CAA  CAT  TTC  CGT  GTC  GCC  CTT  ATT
   1▶ t   Ser  Ile  Gln  His  Phe  Arg  Val  Ala  Leu  Ile

3526  CCC  TTT  TTT  GCG  GCA  TTT  TGC  CTT  CCT  GTT  TTT
  12▶ Pro  Phe  Phe  Ala  Ala  Phe  Cys  Leu  Pro  Val  Phe

3559  GCT  CAC  CCA  GAA  ACG  CTG  GTG  AAA  GTA  AAA  GAT
  23▶ Ala  His  Pro  Glu  Thr  Leu  Val  Lys  Val  Lys  Asp

3592  GCT  GAA  GAT  CAG  TTG  GGT  GCA  CGA  GTG  GGT  TAC
  34▶ Ala  Glu  Asp  Gln  Leu  Gly  Ala  Arg  Val  Gly  Tyr

3625  ATC  GAA  CTG  GAT  CTC  AAC  AGC  GGT  AAG  ATC  CTT
  45▶ Ile  Glu  Leu  Asp  Leu  Asn  Ser  Gly  Lys  Ile  Leu

3658  GAG  AGT  TTT  CGC  CCC  GAA  GAA  CGT  TTT  CCA  ATG
  56▶ Glu  Ser  Phe  Arg  Pro  Glu  Glu  Arg  Phe  Pro  Met

3691  ATG  AGC  ACT  TTT  AAA  GTT  CTG  CTA  TGT  GGC  GCG
  67▶ Met  Ser  Thr  Phe  Lys  Val  Leu  Leu  Cys  Gly  Ala

3724  GTA  TTA  TCC  CGT  GTT  GAC  GCC  GGG  CAA  GAG  CAA
  78▶ Val  Leu  Ser  Arg  Val  Asp  Ala  Gly  Gln  Glu  Gln

3757  CTC  GGT  CGC  CGC  ATA  CAC  TAT  TCT  CAG  AAT  GAC
  89▶ Leu  Gly  Arg  Arg  Ile  His  Tyr  Ser  Gln  Asn  Asp
                      ScaI
3790  TTG  GTT  GAG  TAC  TCA  CCA  GTC  ACA  GAA  AAG  CAT
 100▶ Leu  Val  Glu  Tyr  Ser  Pro  Val  Thr  Glu  Lys  His

3823  CTT  ACG  GAT  GGC  ATG  ACA  GTA  AGA  GAA  TTA  TGC
 111▶ Leu  Thr  Asp  Gly  Met  Thr  Val  Arg  Glu  Leu  Cys
```

Figure 7b (cont'd)

```
3856 AGT GCT GCC ATA ACC ATG AGT GAT AAC ACT GCG
122▶ Ser Ala Ala Ile Thr Met Ser Asp Asn Thr Ala

3889 GCC AAC TTA CTT CTG ACA ACG ATC GGA GGA CCG
133▶ Ala Asn Leu Leu Leu Thr Thr Ile Gly Gly Pro

3922 AAG GAG CTA ACC GCT TTT TTG CAC AAC ATG GGG
144▶ Lys Glu Leu Thr Ala Phe Leu His Asn Met Gly

3955 GAT CAT GTA ACT CGC CTT GAT CGT TGG GAA CCG
155▶ Asp His Val Thr Arg Leu Asp Arg Trp Glu Pro

3988 GAG CTG AAT GAA GCC ATA CCA AAC GAC GAG CGT
166▶ Glu Leu Asn Glu Ala Ile Pro Asn Asp Glu Arg

4021 GAC ACC ACG ATG CCT GTA GCA ATG GCA ACA ACG
177▶ Asp Thr Thr Met Pro Val Ala Met Ala Thr Thr

4054 TTG CGC AAA CTA TTA ACT GGC GAA CTA CTT ACT
188▶ Leu Arg Lys Leu Leu Thr Gly Glu Leu Leu Thr

4087 CTA GCT TCC CGG CAA CAA TTA ATA GAC TGG ATG
199▶ Leu Ala Ser Arg Gln Gln Leu Ile Asp Trp Met

4120 GAG GCG GAT AAA GTT GCA GGA CCA CTT CTG CGC
210▶ Glu Ala Asp Lys Val Ala Gly Pro Leu Leu Arg

4153 TCG GCC CTT CCG GCT GGC TGG TTT ATT GCT GAT
221▶ Ser Ala Leu Pro Ala Gly Trp Phe Ile Ala Asp

4186 AAA TCT GGA GCC GGT GAG CGT GGG TCT CGC GGT
232▶ Lys Ser Gly Ala Gly Glu Arg Gly Ser Arg Gly

4219 ATC ATT GCA GCA CTG GGG CCA GAT GGT AAG CCC
243▶ Ile Ile Ala Ala Leu Gly Pro Asp Gly Lys Pro

4252 TCC CGT ATC GTA GTT ATC TAC ACG ACG GGG AGT
254▶ Ser Arg Ile Val Val Ile Tyr Thr Thr Gly Ser
```

Figure 7b (cont'd)

```
4285 CAG GCA ACT ATG GAT GAA CGA AAT AGA CAG ATC
265▶Gln Ala Thr Met Asp Glu Arg Asn Arg Gln Ile
4318 GCT GAG ATA GGT GCC TCA CTG ATT AAG CAT TGG
276▶Ala Glu Ile Gly Ala Ser Leu Ile Lys His Trp
4351 TAA CTGTCAGACC AAGTTTACTC ATATATACTT
287▶•••
4384 TAGATTGATT TACGCGCCCT GTAGCGGCGC ATTAAGCGCG
4424 GCGGGTGTGG TGGTTACGCG CAGCGTGACC GCTACACTTG
4464 CCAGCGCCCT AGCGCCCGCT CCTTTCGCTT TCTTCCCTTC
4504 CTTTCTCGCC ACGTTCGCCG GCTTTCCCCG TCAAGCTCTA
4544 AATCGGGGGC TCCCTTTAGG GTTCCGATTT AGTGCTTTAC
4584 GGCACCTCGA CCCCAAAAAA CTTGATTTGG GTGATGGTTC
4624 ACGTAGTGGG CCATCGCCCT GATAGACGGT TTTTCGCCCT
4664 TTGACGTTGG AGTCCACGTT CTTTAATAGT GGACTCTTGT
4704 TCCAAACTTG AACAACACTC AACCCTATCT CGGGCTATTC
4744 TTTTGATTTA TAAGGGATTT TGCCGATTTC GGCCTATTGG
4784 TTAAAAAATG AGCTGATTTA ACAAAAATTT AACGCGAATT
4824 TTAACAAAAT ATTAACGTTT ACAATTTAAA AGGATCTAGG
4864 TGAAGATCCT TTTTGATAAT CTCATGACCA AAATCCCTTA
4904 ACGTGAGTTT TCGTTCCACT GAGCGTCAGA CCCCGTAGAA
4944 AAGATCAAAG GATCTTCTTG AGATCCTTTT TTTCTGCGCG
4984 TAATCTGCTG CTTGCAAACA AAAAAACCAC CGCTACCAGC
5024 GGTGGTTTGT TTGCCGGATC AAGAGCTACC AACTCTTTTT
```

Figure 7b (cont'd)

```
5064  CCGAAGGTAA CTGGCTTCAG CAGAGCGCAG ATACCAAATA
5104  CTGTCCTTCT AGTGTAGCCG TAGTTAGGCC ACCACTTCAA
5144  GAACTCTGTA GCACCGCCTA CATACCTCGC TCTGCTAATC
5184  CTGTTACCAG TGGCTGCTGC CAGTGGCGAT AAGTCGTGTC
5224  TTACCGGGTT GGACTCAAGA CGATAGTTAC CGGATAAGGC
5264  GCAGCGGTCG GGCTGAACGG GGGGTTCGTG CACACAGCCC
5304  AGCTTGGAGC GAACGACCTA CACCGAACTG AGATACCTAC
5344  AGCGTGAGCT ATGAGAAAGC GCCACGCTTC CCGAAGGGAG
5384  AAAGGCGGAC AGGTATCCGG TAAGCGGCAG GGTCGGAACA
5424  GGAGAGCGCA CGAGGGAGCT TCCAGGGGGA AACGCCTGGT
5464  ATCTTTATAG TCCTGTCGGG TTTCGCCACC TCTGACTTGA
5504  GCGTCGATTT TTGTGATGCT CGTCAGGGGG GCGGAGCCTA
5544  TGGAAAAACG CCAGCAACGC GGCCTTTTTA CGGTTCCTGG
5584  CCTTTTGCTG GCCTTTTGCT CACATGTTCT TTCCTGCGTT
5624  ATCCCCTGAT TCTGTGGATA ACCGTATTAC CGCCTTTGAG
5664  TGAGCTGATA CCGCTCGCCG CAGCCGAACG ACCGAGCGCA
5704  GCGAGTCAGT GAGCGAGGAA GCGGAAGAGC GCCTGATGCG
5744  GTATTTTCTC CTTACGCATC TGTGCGGTAT TTCACACCGC
5784  ATAGGGTCAT GGCTGCGCCC CGACACCCGC CAACACCCGC
5824  TGACGCGCCC TGACGGGCTT GTCTGCTCCC GGCATCCGCT
5864  TACAGACAAG CTGTGACCGT CTCCGGGAGC TGCATGTGTC
5904  AGAGGTTTTC ACCGTCATCA CCGAAACGCG CGAGGCAGCA
5944  AGGAGATGGC GCCCAACAGT CCCCCGGCCA CGGGGCCTGC
```

Figure 7b (cont'd)

```
5984  CACCATACCC  ACGCCGAAAC  AAGCGCTCAT  GAGCCCGAAG
6024  TGGCGAGCCC  GATCTTCCCC  ATCGGTGATG  TCGGCGATAT
6064  AGGCGCCAGC  AACCGCACCT  GTGGCGCCGG  TGATGCCGGC
6104  CACGATGCGT  CCGGCGTAGA  GGATCTGCTC  ATGTTTGACA
6144  GCTTATC
```

Figure 8:
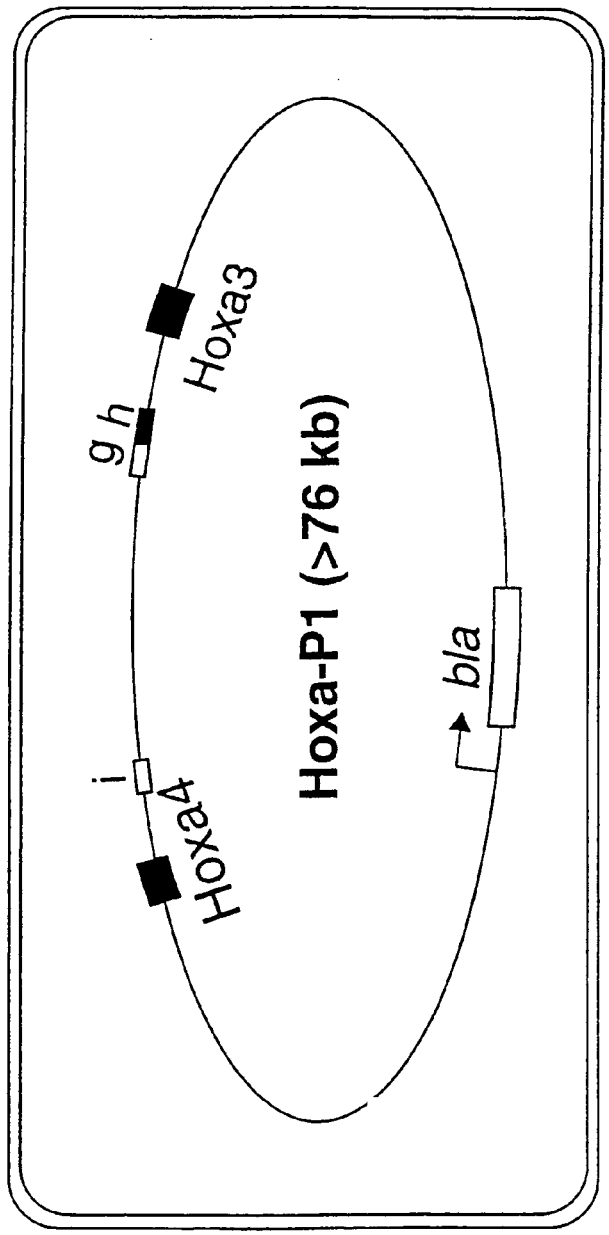
Figure 8:
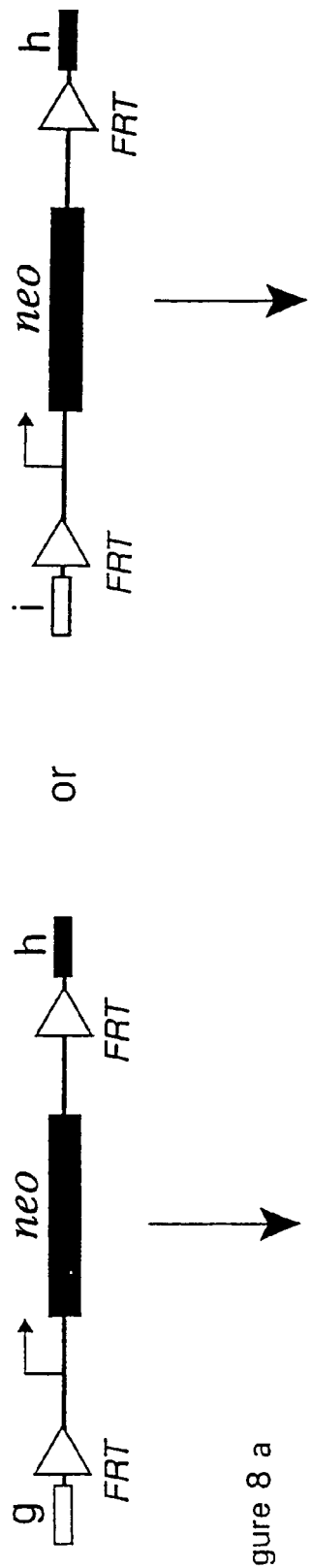
Figure 8:
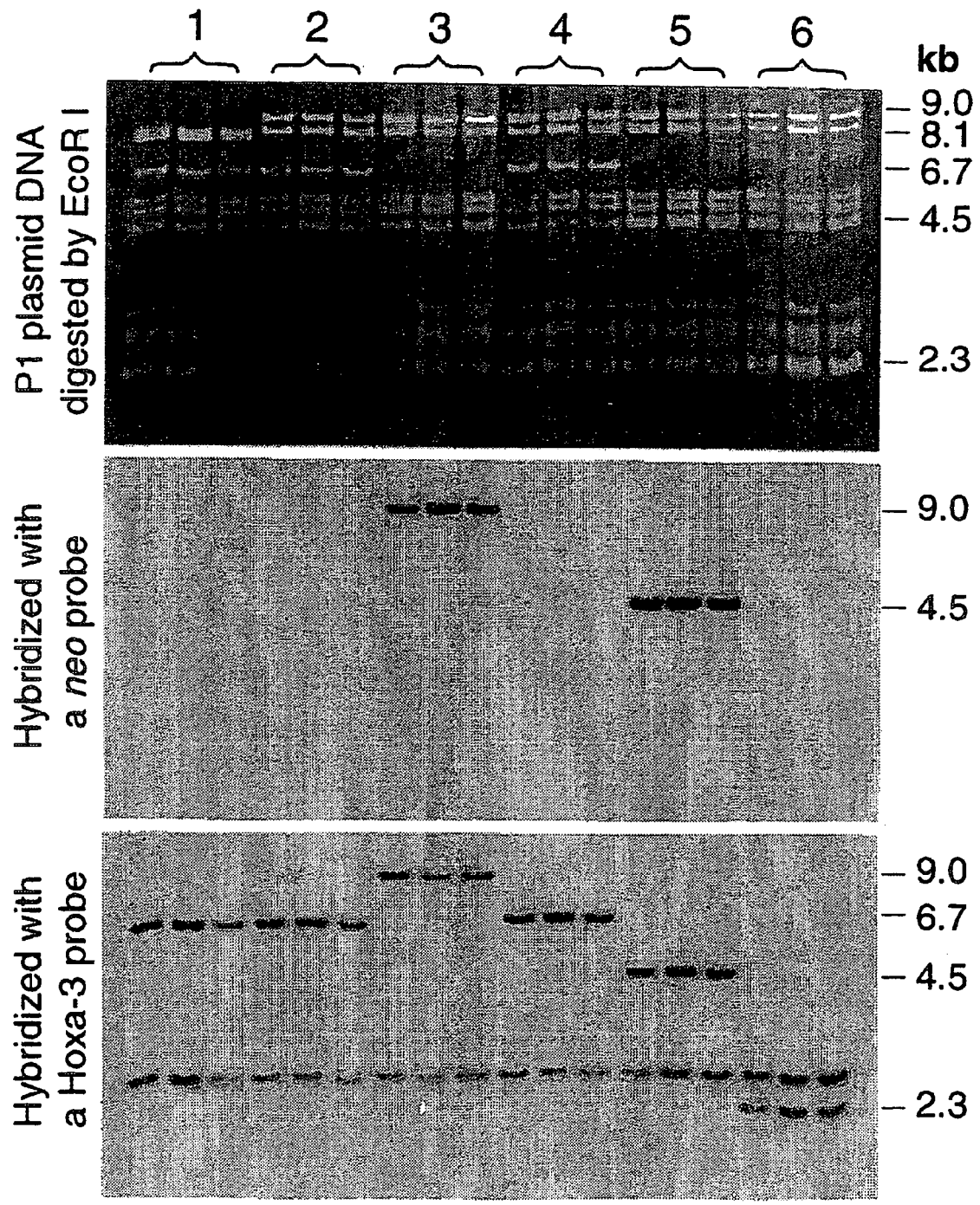

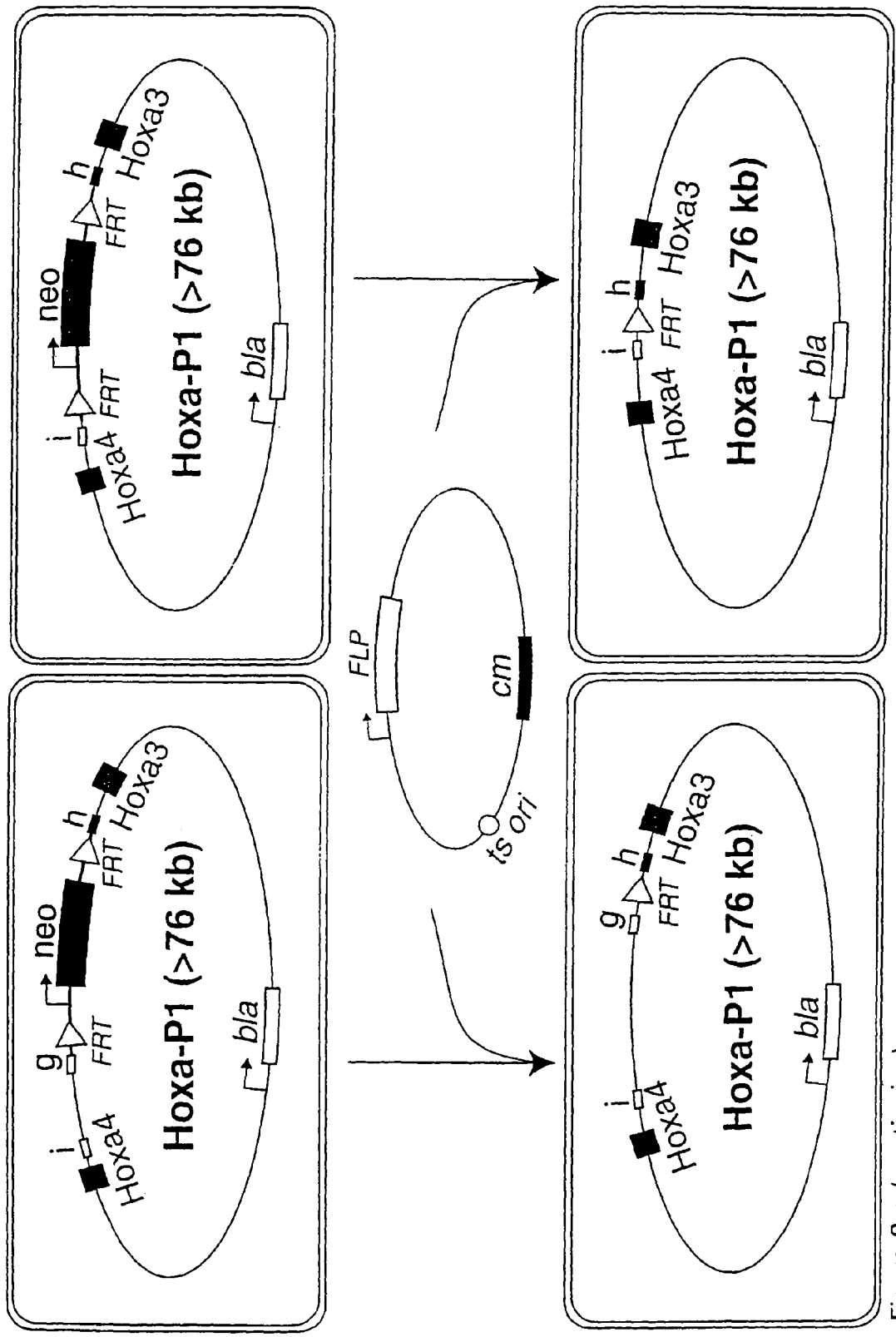
Figure 8 a (continuing)

Figure 13b

```
  1  ATCGATGCATAATGTGCCTGTCAAATGGACGAAGCAGGG
 40  ATTCTGCAAACCCTATGCTACTCCGTCAAGCCGTCAATT
 79  GTCTGATTCGTTACCAA TTA TGA CAA CTT GAC
                 293◄• • • Ser Leu Lys Val
111  GGC TAC ATC ATT CAC TTT TTC TTC ACA ACC
288◄Ala Val Asp Asn Val Lys Glu Glu Cys Gly
141  GGC ACG GAA CTC GCT CGG GCT GGC CCC GGT
278◄Ala Arg Phe Glu Ser Pro Ser Ala Gly Thr
171  GCA TTT TTT AAA TAC CCG CGA GAA ATA GAG
268◄Cys Lys Lys Phe Val Arg Ser Phe Tyr Leu
201  TTG ATC GTC AAA ACC AAC ATT GCG ACC GAC
258◄Gln Asp Asp Phe Gly Val Asn Arg Gly Val
231  GGT GGC GAT AGG CAT CCG GGT GGT GCT CAA
248◄Thr Ala Ile Pro Met Arg Thr Thr Ser Leu
261  AAG CAG CTT CGC CTG GCT GAT ACG TTG GTC
238◄Leu Leu Lys Ala Gln Ser Ile Arg Gln Asp
291  CTC GCG CCA GCT TAA GAC GCT AAT CCC TAA
228◄Glu Arg Trp Ser Leu Val Ser Ile Gly Leu
321  CTG CTG GCG GAA AAG ATG TGA CAG ACG CGA
218◄Gln Gln Arg Phe Leu His Ser Leu Arg Ser
351  CGG CGA CAA GCA AAC ATG CTG TGC GAC GCT
208◄Pro Ser Leu Cys Val His Gln Ala Val Ser
381  GGC GAT ATC AAA ATT GCT GTC TGC CAG GTC
198◄Ala Ile Asp Phe Asn Ser Asp Ala Leu His
411  ATC GCT GAT GTA CTG ACA AGC CTC GCG TAC
```

Figure 13b (cont'd)

```
188◄Asp  Ser  Ile  Tyr  Gln  Cys  Ala  Glu  Arg  Val
441  CCG  ATT  ATC  CAT  CGG  TGG  ATG  GAG  CGA  CTC
178◄Arg  Asn  Asp  Met  Pro  Pro  His  Leu  Ser  Glu
471  GTT  AAT  CGC  TTC  CAT  GCG  CCG  CAG  TAA  CAA
168◄Asn  Ile  Ala  Glu  Met  Arg  Arg  Leu  Leu  Leu
501  TTG  CTC  AAG  CAG  ATT  TAT  CGC  CAG  CAG  CTC
158◄Gln  Glu  Leu  Leu  Asn  Ile  Ala  Leu  Leu  Glu
531  CGA  ATA  GCG  CCC  TTC  CCC  TTG  CCC  GGC  GTT
148◄Ser  Tyr  Arg  Gly  Glu  Gly  Gln  Gly  Ala  Asn
561  AAT  GAT  TTG  CCC  AAA  CAG  GTC  GCT  GAA  ATG
138◄Ile  Ile  Gln  Gly  Phe  Leu  Asp  Ser  Phe  His
591  CGG  CTG  GTG  CGC  TTC  ATC  CGG  GCG  AAA  GAA
128◄Pro  Gln  His  Ala  Glu  Asp  Pro  Arg  Phe  Phe
621  CCC  CGT  ATT  GGC  AAA  TAT  TGA  CGG  CCA  GTT
118◄Gly  Thr  Asn  Ala  Phe  Ile  Ser  Pro  Trp  Asn
651  AAG  CCA  TTC  ATG  CCA  GTA  GGC  GCG  CGG  ACG
108◄Leu  Trp  Glu  His  Trp  Tyr  Ala  Arg  Pro  Arg
681  AAA  GTA  AAC  CCA  CTG  GTG  ATA  CCA  TTC  GCG
 98◄Phe  Tyr  Val  Trp  Gln  His  Tyr  Trp  Glu  Arg
711  AGC  CTC  CGG  ATG  ACG  ACC  GTA  GTG  ATG  AAT
 88◄Ala  Glu  Pro  His  Arg  Gly  Tyr  His  His  Ile
741  CTC  TCC  TGG  CGG  GAA  CAG  CAA  AAT  ATC  ACC
 78◄Glu  Gly  Pro  Pro  Phe  Leu  Leu  Ile  Asp  Gly
771  CGG  TCG  GCA  AAC  AAA  TTC  TCG  TCC  CTG  ATT
 68◄Pro  Arg  Cys  Val  Phe  Glu  Arg  Gly  Gln  Asn
```

Figure 13b (cont'd)

```
1255 TTTTTATCGCAACTCTCTACTGTTTCTCCATACCCGTTT
           NheI         EcoRI      NcoI    BamHI
1294 TTTTGGGCTAGCAGGAGGAAT TCACC ATG GAT CCC
                                    1▶Met Asp Pro

1329 GTA ATC GTA GAA GAC ATA GAG CCA GGT ATT
   4▶Val Ile Val Glu Asp Ile Glu Pro Gly Ile

1359 TAT TAC GGA ATT TCG AAT GAG AAT TAC CAC
  14▶Tyr Tyr Gly Ile Ser Asn Glu Asn Tyr His

1389 GCG GGT CCC GGT ATC AGT AAG TCT CAG CTC
  24▶Ala Gly Pro Gly Ile Ser Lys Ser Gln Leu

1419 GAT GAC ATT GCT GAT ACT CCG GCA CTA TAT
  34▶Asp Asp Ile Ala Asp Thr Pro Ala Leu Tyr

1449 TTG TGG CGT AAA AAT GCC CCC GTG GAC ACC
  44▶Leu Trp Arg Lys Asn Ala Pro Val Asp Thr

1479 ACA AAG ACA AAA ACG CTC GAT TTA GGA ACT
  54▶Thr Lys Thr Lys Thr Leu Asp Leu Gly Thr

1509 GCT TTC CAC TGC CGG GTA CTT GAA CCG GAA
  64▶Ala Phe His Cys Arg Val Leu Glu Pro Glu
           EcoRI
1539 GAA TTC AGT AAC CGC TTT ATC GTA GCA CCT
  74▶Glu Phe Ser Asn Arg Phe Ile Val Ala Pro

1569 GAA TTT AAC CGC CGT ACA AAC GCC GGA AAA
  84▶Glu Phe Asn Arg Arg Thr Asn Ala Gly Lys

1599 GAA GAA GAG AAA GCG TTT CTG ATG GAA TGC
  94▶Glu Glu Glu Lys Ala Phe Leu Met Glu Cys

1629 GCA AGC ACA GGA AAA ACG GTT ATC ACT GCG
 104▶Ala Ser Thr Gly Lys Thr Val Ile Thr Ala
```

Figure 13b (cont'd)

```
1659 GAA GAA GGC CGG AAA ATT GAA CTC ATG TAT
 114▶Glu Glu Gly Arg Lys Ile Glu Leu Met Tyr

1689 CAA AGC GTT ATG GCT TTG CCG CTG GGG CAA
 124▶Gln Ser Val Met Ala Leu Pro Leu Gly Gln

1719 TGG CTT GTT GAA AGC GCC GGA CAC GCT GAA
 134▶Trp Leu Val Glu Ser Ala Gly His Ala Glu

1749 TCA TCA ATT TAC TGG GAA GAT CCT GAA ACA
 144▶Ser Ser Ile Tyr Trp Glu Asp Pro Glu Thr

1779 GGA ATT TTG TGT CGG TGC CGT CCG GAC AAA
 154▶Gly Ile Leu Cys Arg Cys Arg Pro Asp Lys

1809 ATT ATC CCT GAA TTT CAC TGG ATC ATG GAC
 164▶Ile Ile Pro Glu Phe His Trp Ile Met Asp

1839 GTG AAA ACT ACG GCG GAT ATT CAA CGA TTC
 174▶Val Lys Thr Thr Ala Asp Ile Gln Arg Phe

1869 AAA ACC GCT TAT TAC GAC TAC CGC TAT CAC
 184▶Lys Thr Ala Tyr Tyr Asp Tyr Arg Tyr His

1899 GTT CAG GAT GCA TTC TAC AGT GAC GGT TAT
 194▶Val Gln Asp Ala Phe Tyr Ser Asp Gly Tyr

1929 GAA GCA CAG TTT GGA GTG CAG CCA ACT TTC
 204▶Glu Ala Gln Phe Gly Val Gln Pro Thr Phe

1959 GTT TTT CTG GTT GCC AGC ACA ACT ATT GAA
 214▶Val Phe Leu Val Ala Ser Thr Thr Ile Glu

1989 TGC GGA CGT TAT CCG GTT GAA ATT TTC ATG
 224▶Cys Gly Arg Tyr Pro Val Glu Ile Phe Met

2019 ATG GGC GAA GAA GCA AAA CTG GCA GGT CAA
 234▶Met Gly Glu Glu Ala Lys Leu Ala Gly Gln
```

Figure 13b (cont'd)

```
2049 CAG GAA TAT CAC CGC AAT CTG CGA ACC CTG
 244▶Gln Glu Tyr His Arg Asn Leu Arg Thr Leu

2079 TCT GAC TGC CTG AAT ACC GAT GAA TGG CCA
 254▶Ser Asp Cys Leu Asn Thr Asp Glu Trp Pro

2109 GCT ATT AAG ACA TTA TCA CTG CCC CGC TGG
 264▶Ala Ile Lys Thr Leu Ser Leu Pro Arg Trp
                                       XhoI  KpnI
2139 GCT AAG GAA TAT GCA AAT GAC TAGATCTCGAG
 274▶Ala Lys Glu Tyr Ala Asn Asp

2171 GTACCCGAGCACGTGTTGACAATTAATCATCGGCATAGT

2210 ATATCGGCATAGTATAATACGACAAGGTGAGGAACTAAA
      NcoI
2249 CC ATG GCT AAG CAA CCA CCA ATC GCA AAA
     1▶Met Ala Lys Gln Pro Pro Ile Ala Lys

2278 GCC GAT CTG CAA AAA ACT CAG GGA AAC CGT
  10▶Ala Asp Leu Gln Lys Thr Gln Gly Asn Arg

2308 GCA CCA GCA GCA GTT AAA AAT AGC GAC GTG
  20▶Ala Pro Ala Ala Val Lys Asn Ser Asp Val

2338 ATT AGT TTT ATT AAC CAG CCA TCA ATG AAA
  30▶Ile Ser Phe Ile Asn Gln Pro Ser Met Lys

2368 GAG CAA CTG GCA GCA GCT CTT CCA CGC CAT
  40▶Glu Gln Leu Ala Ala Ala Leu Pro Arg His

2398 ATG ACG GCT GAA CGT ATG ATC CGT ATC GCC
  50▶Met Thr Ala Glu Arg Met Ile Arg Ile Ala

2428 ACC ACA GAA ATT CGT AAA GTT CCG GCG TTA
  60▶Thr Thr Glu Ile Arg Lys Val Pro Ala Leu
```

Figure 13b (cont'd)

```
2458 GGA AAC TGT GAC ACT ATG AGT TTT GTC AGT
 70▶ Gly Asn Cys Asp Thr Met Ser Phe Val Ser
2488 GCG ATC GTA CAG TGT TCA CAG CTC GGA CTT
 80▶ Ala Ile Val Gln Cys Ser Gln Leu Gly Leu
2518 GAG CCA GGT AGC GCC CTC GGT CAT GCA TAT
 90▶ Glu Pro Gly Ser Ala Leu Gly His Ala Tyr
2548 TTA CTG CCT TTT GGT AAT AAA AAC GAA AAG
100▶ Leu Leu Pro Phe Gly Asn Lys Asn Glu Lys
2578 AGC GGT AAA AAG AAC GTT CAG CTA ATC ATT
110▶ Ser Gly Lys Lys Asn Val Gln Leu Ile Ile
2608 GGC TAT CGC GGC ATG ATT GAT CTG GCT CGC
120▶ Gly Tyr Arg Gly Met Ile Asp Leu Ala Arg
2638 CGT TCT GGT CAA ATC GCC AGC CTG TCA GCC
130▶ Arg Ser Gly Gln Ile Ala Ser Leu Ser Ala
2668 CGT GTT GTC CGT GAA GGT GAC GAG TTT AGC
140▶ Arg Val Val Arg Glu Gly Asp Glu Phe Ser
2698 TTC GAA TTT GGC CTT GAT GAA AAG TTA ATA
150▶ Phe Glu Phe Gly Leu Asp Glu Lys Leu Ile
2728 CAC CGC CCG GGA GAA AAC GAA GAT GCC CCG
160▶ His Arg Pro Gly Glu Asn Glu Asp Ala Pro
2758 GTT ACC CAC GTC TAT GCT GTC GCA AGA CTG
170▶ Val Thr His Val Tyr Ala Val Ala Arg Leu
2788 AAA GAC GGA GGT ACT CAG TTT GAA GTT ATG
180▶ Lys Asp Gly Gly Thr Gln Phe Glu Val Met
2818 ACG CGC AAA CAG ATT GAG CTG GTG CGC AGC
190▶ Thr Arg Lys Gln Ile Glu Leu Val Arg Ser
```

Figure 13b (cont'd)

```
2848 CTG AGT AAA GCT GGT AAT AAC GGG CCG TGG
200▶ Leu Ser Lys Ala Gly Asn Asn Gly Pro Trp

2878 GTA ACT CAC TGG GAA GAA ATG GCA AAG AAA
210▶ Val Thr His Trp Glu Glu Met Ala Lys Lys

2908 ACG GCT ATT CGT CGC CTG TTC AAA TAT TTG
220▶ Thr Ala Ile Arg Arg Leu Phe Lys Tyr Leu

2938 CCC GTA TCA ATT GAG ATC CAG CGT GCA GTA
230▶ Pro Val Ser Ile Glu Ile Gln Arg Ala Val

2968 TCA ATG GAT GAA AAG GAA CCA CTG ACA ATC
240▶ Ser Met Asp Glu Lys Glu Pro Leu Thr Ile

2998 GAT CCT GCA GAT TCC TCT GTA TTA ACC GGG
250▶ Asp Pro Ala Asp Ser Ser Val Leu Thr Gly

3028 GAA TAC AGT GTA ATC GAT AAT TCA GAG GAA
260▶ Glu Tyr Ser Val Ile Asp Asn Ser Glu Glu
           BglII      HindIII
3058 TAG ATCTAAGCTTCCTGCTGAACATCAAAGGCAAGAAA
270▶ •••

3096 ACATCTGTTGTCAAAGACAGCATCCTTGAACAAGGACAA

3135 TTAACAGTTAACAAATAAAAACGCAAAAGAAAATGCCGA

3174 TATCCTATTGGCATTTTCTTTTATTTCTTATCAACATAA
                         XhoI
3213 AGGTGAATCCCATACCTCGAGCTTCACGCTGCCGCAAGC

3252 ACTCAGGGCGCAAGGGCTGCTAAAAGGAAGCGGAACACG

3291 TAGAAAGCCAGTCCGCAGAAACGGTGCTGACCCCGGATG

3330 AATGTCAGCTACTGGGCTATCTGGACAAGGGAAAACGCA

3369 AGCGCAAAGAGAAAGCAGGTAGCTTGCAGTGGGCTTACA
```

Figure 13b (cont'd)

```
3408 TGGCGATAGCTAGACTGGGCGGTTTTATGGACAGCAAGC

3447 GAACCGGAATTGCCAGCTGGGGCGCCCTCTGGTAAGGTT

3486 GGGAAGCCCTGCAAAGTAAACTGGATGGCTTTCTTGCCG
                                          BglII
3525 CCAAGGATCTGATGGCGCAGGGGATCAAGATCTGATCAA

3564 GAGACAGGATGAGGATCGTTTCGC ATG GAT ATT
                                  1▶Met Asp Ile

3597 AAT ACT GAA ACT GAG ATC AAG CAA AAG CAT
   4▶Asn Thr Glu Thr Glu Ile Lys Gln Lys His

3627 TCA CTA ACC CCC TTT CCT GTT TTC CTA ATC
  14▶Ser Leu Thr Pro Phe Pro Val Phe Leu Ile

3657 AGC CCG GCA TTT CGC GGG CGA TAT TTT CAC
  24▶Ser Pro Ala Phe Arg Gly Arg Tyr Phe His

3687 AGC TAT TTC AGG AGT TCA GCC ATG AAC GCT
  34▶Ser Tyr Phe Arg Ser Ser Ala Met Asn Ala

3717 TAT TAC ATT CAG GAT CGT CTT GAG GCT CAG
  44▶Tyr Tyr Ile Gln Asp Arg Leu Glu Ala Gln

3747 AGC TGG GCG CGT CAC TAC CAG CAG CTC GCC
  54▶Ser Trp Ala Arg His Tyr Gln Gln Leu Ala

3777 CGT GAA GAG AAA GAG GCA GAA CTG GCA GAC
  64▶Arg Glu Glu Lys Glu Ala Glu Leu Ala Asp

3807 GAC ATG GAA AAA GGC CTG CCC CAG CAC CTG
  74▶Asp Met Glu Lys Gly Leu Pro Gln His Leu

3837 TTT GAA TCG CTA TGC ATC GAT CAT TTG CAA
  84▶Phe Glu Ser Leu Cys Ile Asp His Leu Gln

3867 CGC CAC GGG GCC AGC AAA AAA TCC ATT ACC
  94▶Arg His Gly Ala Ser Lys Lys Ser Ile Thr
```

Figure 13b (cont'd)

```
3897  CGT GCG TTT GAT GAC GAT GTT GAG TTT CAG
 104▶ Arg Ala Phe Asp Asp Asp Val Glu Phe Gln
3927  GAG CGC ATG GCA GAA CAC ATC CGG TAC ATG
 114▶ Glu Arg Met Ala Glu His Ile Arg Tyr Met
3957  GTT GAA ACC ATT GCT CAC CAC CAG GTT GAT
 124▶ Val Glu Thr Ile Ala His His Gln Val Asp
                                         HindIII
3987  ATT GAT TCA GAG GTA TAA AACGAGTAGA AGCT
 134▶ Ile Asp Ser Glu Val •••
4019  TGGCTGTTTTGGCGGATGAGAGAAGATTTTCAGCCTGAT
4058  ACAGATTAAATCAGAACGCAGAAGCGGTCTGATAAAACA
4097  GAATTTGCCTGGCGGCAGTAGCGCGGTGGTCCCACCTGA
4136  CCCCATGCCGAACTCAGAAGTGAAACGCCGTAGCGCCGA
4175  TGGTAGTGTGGGGTCTCCCCATGCGAGAGTAGGGAACTG
4214  CCAGGCATCAAATAAAACGAAAGGCTCAGTCGAAAGACT
4253  GGGCCTTTCGTTTTATCTGTTGTTTGTCGGTGAACGCTC
4292  TCCTGAGTAGGACAAATCCGCCGGGAGCGGATTTGAACG
4331  TTGCGAAGCAACGGCCCGGAGGGTGGCGGGCAGGACGCC
4370  CGCCATAAACTGCCAGGCATCAAATTAAGCAGAAGGCCA
4409  TCCTGACGGATGGCCTTTTTGCGTTTCTACAAACTCTTT
4448  TGTTTATTTTTCTAAATACATTCAAATATGTATCCGCTC
4487  ATGAGACAATAACCCTGATAAATGCTTCAATAATATTGA
4526  AAAAGGAAGAGT ATG AGT ATT CAA CAT TTC
              1▶ Met Ser Ile Gln His Phe
```

Figure 13b (cont'd)

```
4556  CGT  GTC  GCC  CTT  ATT  CCC  TTT  TTT  GCG  GCA
   7▶ Arg  Val  Ala  Leu  Ile  Pro  Phe  Phe  Ala  Ala

4586  TTT  TGC  CTT  CCT  GTT  TTT  GCT  CAC  CCA  GAA
  17▶ Phe  Cys  Leu  Pro  Val  Phe  Ala  His  Pro  Glu

4616  ACG  CTG  GTG  AAA  GTA  AAA  GAT  GCT  GAA  GAT
  27▶ Thr  Leu  Val  Lys  Val  Lys  Asp  Ala  Glu  Asp

4646  CAG  TTG  GGT  GCA  CGA  GTG  GGT  TAC  ATC  GAA
  37▶ Gln  Leu  Gly  Ala  Arg  Val  Gly  Tyr  Ile  Glu

4676  CTG  GAT  CTC  AAC  AGC  GGT  AAG  ATC  CTT  GAG
  47▶ Leu  Asp  Leu  Asn  Ser  Gly  Lys  Ile  Leu  Glu

4706  AGT  TTT  CGC  CCC  GAA  GAA  CGT  TTT  CCA  ATG
  57▶ Ser  Phe  Arg  Pro  Glu  Glu  Arg  Phe  Pro  Met

4736  ATG  AGC  ACT  TTT  AAA  GTT  CTG  CTA  TGT  GGC
  67▶ Met  Ser  Thr  Phe  Lys  Val  Leu  Leu  Cys  Gly

4766  GCG  GTA  TTA  TCC  CGT  GTT  GAC  GCC  GGG  CAA
  77▶ Ala  Val  Leu  Ser  Arg  Val  Asp  Ala  Gly  Gln

4796  GAG  CAA  CTC  GGT  CGC  CGC  ATA  CAC  TAT  TCT
  87▶ Glu  Gln  Leu  Gly  Arg  Arg  Ile  His  Tyr  Ser
                                    ScaI
4826  CAG  AAT  GAC  TTG  GTT  GAG  TAC  TCA  CCA  GTC
  97▶ Gln  Asn  Asp  Leu  Val  Glu  Tyr  Ser  Pro  Val

4856  ACA  GAA  AAG  CAT  CTT  ACG  GAT  GGC  ATG  ACA
 107▶ Thr  Glu  Lys  His  Leu  Thr  Asp  Gly  Met  Thr

4886  GTA  AGA  GAA  TTA  TGC  AGT  GCT  GCC  ATA  ACC
 117▶ Val  Arg  Glu  Leu  Cys  Ser  Ala  Ala  Ile  Thr

4916  ATG  AGT  GAT  AAC  ACT  GCG  GCC  AAC  TTA  CTT
 127▶ Met  Ser  Asp  Asn  Thr  Ala  Ala  Asn  Leu  Leu
```

Figure 13b (cont'd)

```
4946 CTG ACA ACG ATC GGA GGA CCG AAG GAG CTA
 137▶Leu Thr Thr Ile Gly Gly Pro Lys Glu Leu

4976 ACC GCT TTT TTG CAC AAC ATG GGG GAT CAT
 147▶Thr Ala Phe Leu His Asn Met Gly Asp His

5006 GTA ACT CGC CTT GAT CGT TGG GAA CCG GAG
 157▶Val Thr Arg Leu Asp Arg Trp Glu Pro Glu

5036 CTG AAT GAA GCC ATA CCA AAC GAC GAG CGT
 167▶Leu Asn Glu Ala Ile Pro Asn Asp Glu Arg

5066 GAC ACC ACG ATG CCT GTA GCA ATG GCA ACA
 177▶Asp Thr Thr Met Pro Val Ala Met Ala Thr

5096 ACG TTG CGC AAA CTA TTA ACT GGC GAA CTA
 187▶Thr Leu Arg Lys Leu Leu Thr Gly Glu Leu

5126 CTT ACT CTA GCT TCC CGG CAA CAA TTA ATA
 197▶Leu Thr Leu Ala Ser Arg Gln Gln Leu Ile

5156 GAC TGG ATG GAG GCG GAT AAA GTT GCA GGA
 207▶Asp Trp Met Glu Ala Asp Lys Val Ala Gly

5186 CCA CTT CTG CGC TCG GCC CTT CCG GCT GGC
 217▶Pro Leu Leu Arg Ser Ala Leu Pro Ala Gly

5216 TGG TTT ATT GCT GAT AAA TCT GGA GCC GGT
 227▶Trp Phe Ile Ala Asp Lys Ser Gly Ala Gly

5246 GAG CGT GGG TCT CGC GGT ATC ATT GCA GCA
 237▶Glu Arg Gly Ser Arg Gly Ile Ile Ala Ala

5276 CTG GGG CCA GAT GGT AAG CCC TCC CGT ATC
 247▶Leu Gly Pro Asp Gly Lys Pro Ser Arg Ile

5306 GTA GTT ATC TAC ACG ACG GGG AGT CAG GCA
 257▶Val Val Ile Tyr Thr Thr Gly Ser Gln Ala
```

Figure 13b (cont'd)

```
5336  ACT ATG GAT GAA CGA AAT AGA CAG ATC GCT
 267▶ Thr Met Asp Glu Arg Asn Arg Gln Ile Ala

5366  GAG ATA GGT GCC TCA CTG ATT AAG CAT TGG
 277▶ Glu Ile Gly Ala Ser Leu Ile Lys His Trp

5396  TAA CTGTCAGACCAAGTTTACTCATATATACTTTAGAT
 287▶ •••

5434  TGATTTACGCGCCTGTAGCGGCGCATTAAGCGCGGCGG
5473  GTGTGGTGGTTACGCGCAGCGTGACCGCTACACTTGCCA
5512  GCGCCCTAGCGCCCGCTCCTTTCGCTTTCTTCCCTTCCT
5551  TTCTCGCCACGTTCGCCGGCTTTCCCCGTCAAGCTCTAA
5590  ATCGGGGCTCCCTTTAGGGTTCCGATTTAGTGCTTTAC
5629  GGCACCTCGACCCCAAAAAACTTGATTTGGGTGATGGTT
5668  CACGTAGTGGGCCATCGCCCTGATAGACGGTTTTTCGCC
5707  CTTTGACGTTGGAGTCCACGTTCTTTAATAGTGGACTCT
5746  TGTTCCAAACTTGAACAACACTCAACCCTATCTCGGGCT
5785  ATTCTTTTGATTTATAAGGGATTTTGCCGATTTCGGCCT
5824  ATTGGTTAAAAAATGAGCTGATTTAACAAAAATTTAACG
5863  CGAATTTTAACAAAATATTAACGTTTACAATTTAAAAGG
5902  ATCTAGGTGAAGATCCTTTTTGATAATCTCATGACCAAA
5941  ATCCCTTAACGTGAGTTTTCGTTCCACTGAGCGTCAGAC
5980  CCCGTAGAAAAGATCAAAGGATCTTCTTGAGATCCTTTT
6019  TTTCTGCGCGTAATCTGCTGCTTGCAAACAAAAAAACCA
6058  CCGCTACCAGCGGTGGTTTGTTTGCCGGATCAAGAGCTA
6097  CCAACTCTTTTTCCGAAGGTAACTGGCTTCAGCAGAGCG
```

Figure 13b (cont'd)

```
6136  CAGATACCAAATACTGTCCTTCTAGTGTAGCCGTAGTTA
6175  GGCCACCACTTCAAGAACTCTGTAGCACCGCCTACATAC
6214  CTCGCTCTGCTAATCCTGTTACCAGTGGCTGCTGCCAGT
6253  GGCGATAAGTCGTGTCTTACCGGGTTGGACTCAAGACGA
6292  TAGTTACCGGATAAGGCGCAGCGGTCGGGCTGAACGGGG
6331  GGTTCGTGCACACAGCCCAGCTTGGAGCGAACGACCTAC
6370  ACCGAACTGAGATACCTACAGCGTGAGCTATGAGAAAGC
6409  GCCACGCTTCCCGAAGGGAGAAAGGCGGACAGGTATCCG
6448  GTAAGCGGCAGGGTCGGAACAGGAGAGCGCACGAGGGAG
6487  CTTCCAGGGGGAAACGCCTGGTATCTTTATAGTCCTGTC
6526  GGGTTTCGCCACCTCTGACTTGAGCGTCGATTTTTGTGA
6565  TGCTCGTCAGGGGGGCGGAGCCTATGGAAAAACGCCAGC
6604  AACGCGGCCTTTTTACGGTTCCTGGCCTTTTGCTGGCCT
6643  TTTGCTCACATGTTCTTTCCTGCGTTATCCCCTGATTCT
6682  GTGGATAACCGTATTACCGCCTTTGAGTGAGCTGATACC
6721  GCTCGCCGCAGCCGAACGACCGAGCGCAGCGAGTCAGTG
6760  AGCGAGGAAGCGGAAGAGCGCCTGATGCGGTATTTTCTC
6799  CTTACGCATCTGTGCGGTATTTCACACCGCATAGGGTCA
6838  TGGCTGCGCCCCGACACCCGCCAACACCCGCTGACGCGC
6877  CCTGACGGGCTTGTCTGCTCCCGGCATCCGCTTACAGAC
6916  AAGCTGTGACCGTCTCCGGAGCTGCATGTGTCAGAGGT
6955  TTTCACCGTCATCACCGAAACGCGCGAGGCAGCAAGGAG
```

Figure 13b (cont'd)

6994 ATGGCGCCCAACAGTCCCCCGGCCACGGGGCCTGCCACC

7033 ATACCCACGCCGAAACAAGCGCTCATGAGCCCGAAGTGG

7072 CGAGCCCGATCTTCCCCATCGGTGATGTCGGCGATATAG

7111 GCGCCAGCAACCGCACCTGTGGCGCCGGTGATGCCGGCC

7150 ACGATGCGTCCGGCGTAGAGGATCTGCTCATGTTTGACA

7189 GCTTATC

Figure 14b

```
         NsiI
  1  ATCGATGCATAATGTGCCTGTCAAATGGACGAAGCAGGG

40  ATTCTGCAAACCCTATGCTACTCCGTCAAGCCGTCAATT

79  GTCTGATTCGTTACCAA TTA TGA CAA CTT GAC
                   293◄• • • Ser Leu Lys Val

111  GGC TAC ATC ATT CAC TTT TTC TTC ACA ACC
288◄ Ala Val Asp Asn Val Lys Glu Glu Cys Gly

141  GGC ACG GAA CTC GCT CGG GCT GGC CCC GGT
278◄ Ala Arg Phe Glu Ser Pro Ser Ala Gly Thr

171  GCA TTT TTT AAA TAC CCG CGA GAA ATA GAG
268◄ Cys Lys Lys Phe Val Arg Ser Phe Tyr Leu

201  TTG ATC GTC AAA ACC AAC ATT GCG ACC GAC
258◄ Gln Asp Asp Phe Gly Val Asn Arg Gly Val

231  GGT GGC GAT AGG CAT CCG GGT GGT GCT CAA
248◄ Thr Ala Ile Pro Met Arg Thr Thr Ser Leu

261  AAG CAG CTT CGC CTG GCT GAT ACG TTG GTC
238◄ Leu Leu Lys Ala Gln Ser Ile Arg Gln Asp

291  CTC GCG CCA GCT TAA GAC GCT AAT CCC TAA
228◄ Glu Arg Trp Ser Leu Val Ser Ile Gly Leu

321  CTG CTG GCG GAA AAG ATG TGA CAG ACG CGA
218◄ Gln Gln Arg Phe Leu His Ser Leu Arg Ser

351  CGG CGA CAA GCA AAC ATG CTG TGC GAC GCT
208◄ Pro Ser Leu Cys Val His Gln Ala Val Ser
            EcoRV
381  GGC GAT ATC AAA ATT GCT GTC TGC CAG GTG
198◄ Ala Ile Asp Phe Asn Ser Asp Ala Leu His
```

Figure 14b (cont'd)

```
411  ATC  GCT  GAT  GTA  CTG  ACA  AGC  CTC  GCG  TAC
188◄Asp  Ser  Ile  Tyr  Gln  Cys  Ala  Glu  Arg  Val

441  CCG  ATT  ATC  CAT  CGG  TGG  ATG  GAG  CGA  CTC
178◄Arg  Asn  Asp  Met  Pro  Pro  His  Leu  Ser  Glu

471  GTT  AAT  CGC  TTC  CAT  GCG  CCG  CAG  TAA  CAA
168◄Asn  Ile  Ala  Glu  Met  Arg  Arg  Leu  Leu  Leu

501  TTG  CTC  AAG  CAG  ATT  TAT  CGC  CAG  CAG  CTC
158◄Gln  Glu  Leu  Leu  Asn  Ile  Ala  Leu  Leu  Glu

531  CGA  ATA  GCG  CCC  TTC  CCC  TTG  CCC  GGC  GTT
148◄Ser  Tyr  Arg  Gly  Glu  Gly  Gln  Gly  Ala  Asn

561  AAT  GAT  TTG  CCC  AAA  CAG  GTC  GCT  GAA  ATG
138◄Ile  Ile  Gln  Gly  Phe  Leu  Asp  Ser  Phe  His

591  CGG  CTG  GTG  CGC  TTC  ATC  CGG  GCG  AAA  GAA
128◄Pro  Gln  His  Ala  Glu  Asp  Pro  Arg  Phe  Phe

621  CCC  CGT  ATT  GGC  AAA  TAT  TGA  CGG  CCA  GTT
118◄Gly  Thr  Asn  Ala  Phe  Ile  Ser  Pro  Trp  Asn

651  AAG  CCA  TTC  ATG  CCA  GTA  GGC  GCG  CGG  ACG
108◄Leu  Trp  Glu  His  Trp  Tyr  Ala  Arg  Pro  Arg

681  AAA  GTA  AAC  CCA  CTG  GTG  ATA  CCA  TTC  GCG
 98◄Phe  Tyr  Val  Trp  Gln  His  Tyr  Trp  Glu  Arg

711  AGC  CTC  CGG  ATG  ACG  ACC  GTA  GTG  ATG  AAT
 88◄Ala  Glu  Pro  His  Arg  Gly  Tyr  His  His  Ile

741  CTC  TCC  TGG  CGG  GAA  CAG  CAA  AAT  ATC  ACC
 78◄Glu  Gly  Pro  Pro  Phe  Leu  Leu  Ile  Asp  Gly

771  CGG  TCG  GCA  AAC  AAA  TTC  TCG  TCC  CTG  ATT
 68◄Pro  Arg  Cys  Val  Phe  Glu  Arg  Gly  Gln  Asn
```

Figure 14b (cont'd)

```
 801 TTT CAC CAC CCC CTG ACC GCG AAT GGT GAG
  58◄Lys Val Val Gly Gln Gly Arg Ile Thr Leu
 831 ATT GAG AAT ATA ACC TTT CAT TCC CAG CGG
  48◄Asn Leu Ile Tyr Gly Lys Met Gly Leu Pro
 861 TCG GTC GAT AAA AAA ATC GAG ATA ACC GTT
  38◄Arg Asp Ile Phe Phe Asp Leu Tyr Gly Asn
 891 GGC CTC AAT CGG CGT TAA ACC CGC CAC CAG
  28◄Ala Glu Ile Pro Thr Leu Gly Ala Val Leu
 921 ATG GGC ATT AAA CGA GTA TCC CGG CAG CAG
  18◄His Ala Asn Phe Ser Tyr Gly Pro Leu Leu
 951 GGG ATC ATT TTG CGC TTC AGC CAT ACTTTC
   8◄Pro Asp Asn Gln Ala Glu Ala Met
 982 ATACTCCCGCCATTCAGAGAAGAAACCAATTGTCCATAT
1021 TGCATCAGACATTGCCGTCACTGCGTCTTTTACTGGCTC
1060 TTCTCGCTAACCAAACCGGTAACCCCGCTTATTAAAAGC
1099 ATTCTGTAACAAAGCGGGACCAAAGCCATGACAAAAACG
1138 CGTAACAAAAGTGTCTATAATCACGGCAGAAAAGTCCAC
1177 ATTGATTATTTGCACGGCGTCACACTTTGCTATGCCATA
                                    BamHI
1216 GCATTTTTATCCATAAGATTAGCGGATCCTACCTGACGC
1255 TTTTTATCGCAACTCTCTACTGTTTCTCCATACCCGTTT
             NheI            EcoRI
1294 TTTTGGGCTAGCAGGAGGAATTCACC ATG ACA CCG
                                 1►Met Thr Pro
          PstI
1329 GAC ATT ATC CTG CAG CGT ACC GGG ATC GAT
```

Figure 14b (cont'd)

```
       4▶ Asp  Ile  Ile  Leu  Gln  Arg  Thr  Gly  Ile  Asp
    1359 GTG  AGA  GCT  GTC  GAA  CAG  GGG  GAT  GAT  GCG
      14▶ Val  Arg  Ala  Val  Glu  Gln  Gly  Asp  Asp  Ala
    1389 TGG  CAC  AAA  TTA  CGG  CTC  GGC  GTC  ATC  ACC
      24▶ Trp  His  Lys  Leu  Arg  Leu  Gly  Val  Ile  Thr
    1419 GCT  TCA  GAA  GTT  CAC  AAC  GTG  ATA  GCA  AAA
      34▶ Ala  Ser  Glu  Val  His  Asn  Val  Ile  Ala  Lys
    1449 CCC  CGC  TCC  GGA  AAG  AAG  TGG  CCT  GAC  ATG
      44▶ Pro  Arg  Ser  Gly  Lys  Lys  Trp  Pro  Asp  Met
    1479 AAA  ATG  TCC  TAC  TTC  CAC  ACC  CTG  CTT  GCT
      54▶ Lys  Met  Ser  Tyr  Phe  His  Thr  Leu  Leu  Ala
    1509 GAG  GTT  TGC  ACC  GGT  GTG  GCT  CCG  GAA  GTT
      64▶ Glu  Val  Cys  Thr  Gly  Val  Ala  Pro  Glu  Val
    1539 AAC  GCT  AAA  GCA  CTG  GCC  TGG  GGA  AAA  CAG
      74▶ Asn  Ala  Lys  Ala  Leu  Ala  Trp  Gly  Lys  Gln
                                                     EcoRI
    1569 TAC  GAG  AAC  GAC  GCC  AGA  ACC  CTG  TTT  GAA
      84▶ Tyr  Glu  Asn  Asp  Ala  Arg  Thr  Leu  Phe  Glu
    1599 TTC  ACT  TCC  GGC  GTG  AAT  GTT  ACT  GAA  TCC
      94▶ Phe  Thr  Ser  Gly  Val  Asn  Val  Thr  Glu  Ser
    1629 CCG  ATC  ATC  TAT  CGC  GAC  GAA  AGT  ATG  CGT
     104▶ Pro  Ile  Ile  Tyr  Arg  Asp  Glu  Ser  Met  Arg
    1659 ACC  GCC  TGC  TCT  CCC  GAT  GGT  TTA  TGC  AGT
     114▶ Thr  Ala  Cys  Ser  Pro  Asp  Gly  Leu  Cys  Ser
    1689 GAC  GGC  AAC  GGC  CTT  GAA  CTG  AAA  TGC  CCG
     124▶ Asp  Gly  Asn  Gly  Leu  Glu  Leu  Lys  Cys  Pro
```

Figure 14b (cont'd)

```
1719  TTT  ACC  TCC  CGG  GAT  TTC  ATG  AAG  TTC  CGG
134▶  Phe  Thr  Ser  Arg  Asp  Phe  Met  Lys  Phe  Arg

1749  CTC  GGT  GGT  TTC  GAG  GCC  ATA  AAG  TCA  GCT
144▶  Leu  Gly  Gly  Phe  Glu  Ala  Ile  Lys  Ser  Ala

1779  TAC  ATG  GCC  CAG  GTG  CAG  TAC  AGC  ATG  TGG
154▶  Tyr  Met  Ala  Gln  Val  Gln  Tyr  Ser  Met  Trp

1809  GTG  ACG  CGA  AAA  AAT  GCC  TGG  TAC  TTT  GCC
164▶  Val  Thr  Arg  Lys  Asn  Ala  Trp  Tyr  Phe  Ala

1839  AAC  TAT  GAC  CCG  CGT  ATG  AAG  CGT  GAA  GGC
174▶  Asn  Tyr  Asp  Pro  Arg  Met  Lys  Arg  Glu  Gly

1869  CTG  CAT  TAT  GTC  GTG  ATT  GAG  CGG  GAT  GAA
184▶  Leu  His  Tyr  Val  Val  Ile  Glu  Arg  Asp  Glu

1899  AAG  TAC  ATG  GCG  AGT  TTT  GAC  GAG  ATC  GTG
194▶  Lys  Tyr  Met  Ala  Ser  Phe  Asp  Glu  Ile  Val

1929  CCG  GAG  TTC  ATC  GAA  AAA  ATG  GAC  GAG  GCA
204▶  Pro  Glu  Phe  Ile  Glu  Lys  Met  Asp  Glu  Ala

1959  CTG  GCT  GAA  ATT  GGT  TTT  GTA  TTT  GGG  GAG
214▶  Leu  Ala  Glu  Ile  Gly  Phe  Val  Phe  Gly  Glu
                                       KpnI
1989  CAA  TGG  CGA  TAGATCCGGTACCCGAGCACGTGTTGA
224▶  Gln  Trp  Arg  • • •

2025  CAATTAATCATCGGCATAGTATATCGGCATAGTATAATA

2064  CGACAAGGTGAGGAACTAAACC  ATG  AGT  ACT  GCA
                              1▶Met  Ser  Thr  Ala

2098  CTC  GCA  ACG  CTG  GCT  GGG  AAG  CTG  GCT  GAA
5▶    Leu  Ala  Thr  Leu  Ala  Gly  Lys  Leu  Ala  Glu
```

Figure 14b (cont'd)

```
                                         SalI
2128  CGT GTC GGC ATG GAT TCT GTC GAC CCA CAG
  15▶ Arg Val Gly Met Asp Ser Val Asp Pro Gln

2158  GAA CTG ATC ACC ACT CTT CGC CAG ACG GCA
  25▶ Glu Leu Ile Thr Thr Leu Arg Gln Thr Ala

2188  TTT AAA GGT GAT GCC AGC GAT GCG CAG TTC
  35▶ Phe Lys Gly Asp Ala Ser Asp Ala Gln Phe

2218  ATC GCA TTA CTG ATC GTT GCC AAC CAG TAC
  45▶ Ile Ala Leu Leu Ile Val Ala Asn Gln Tyr

2248  GGC CTT AAT CCG TGG ACG AAA GAA ATT TAC
  55▶ Gly Leu Asn Pro Trp Thr Lys Glu Ile Tyr

2278  GCC TTT CCT GAT AAG CAG AAT GGC ATC GTT
  65▶ Ala Phe Pro Asp Lys Gln Asn Gly Ile Val

2308  CCG GTG GTG GGC GTT GAT GGC TGG TCC CGC
  75▶ Pro Val Val Gly Val Asp Gly Trp Ser Arg

2338  ATC ATC AAT GAA AAC CAG CAG TTT GAT GGC
  85▶ Ile Ile Asn Glu Asn Gln Gln Phe Asp Gly

2368  ATG GAC TTT GAG CAG GAC AAT GAA TCC TGT
  95▶ Met Asp Phe Glu Gln Asp Asn Glu Ser Cys

2398  ACA TGC CGG ATT TAC CGC AAG GAC CGT AAT
 105▶ Thr Cys Arg Ile Tyr Arg Lys Asp Arg Asn

2428  CAT CCG ATC TGC GTT ACC GAA TGG ATG GAT
 115▶ His Pro Ile Cys Val Thr Glu Trp Met Asp

2458  GAA TGC CGC CGC GAA CCA TTC AAA ACT CGC
 125▶ Glu Cys Arg Arg Glu Pro Phe Lys Thr Arg

2488  GAA GGC AGA GAA ATC ACG GGG CCG TGG CAG
 135▶ Glu Gly Arg Glu Ile Thr Gly Pro Trp Gln
```

Figure 14b (cont'd)

```
2518  TCG  CAT  CCC  AAA  CGG  ATG  TTA  CGT  CAT  AAA
145 ► Ser  His  Pro  Lys  Arg  Met  Leu  Arg  His  Lys

2548  GCC  ATG  ATT  CAG  TGT  GCC  CGT  CTG  GCC  TTC
155 ► Ala  Met  Ile  Gln  Cys  Ala  Arg  Leu  Ala  Phe

2578  GGA  TTT  GCT  GGT  ATC  TAT  GAC  AAG  GAT  GAA
165 ► Gly  Phe  Ala  Gly  Ile  Tyr  Asp  Lys  Asp  Glu

2608  GCC  GAG  CGC  ATT  GTC  GAA  AAT  ACT  GCA  TAC
175 ► Ala  Glu  Arg  Ile  Val  Glu  Asn  Thr  Ala  Tyr
              PstI

2638  ACT  GCA  GAA  CGT  CAG  CCG  GAA  CGC  GAC  ATC
185 ► Thr  Ala  Glu  Arg  Gln  Pro  Glu  Arg  Asp  Ile

2668  ACT  CCG  GTT  AAC  GAT  GAA  ACC  ATG  CAG  GAG
195 ► Thr  Pro  Val  Asn  Asp  Glu  Thr  Met  Gln  Glu

2698  ATT  AAC  ACT  CTG  CTG  ATC  GCC  CTG  GAT  AAA
205 ► Ile  Asn  Thr  Leu  Leu  Ile  Ala  Leu  Asp  Lys

2728  ACA  TGG  GAT  GAC  GAC  TTA  TTG  CCG  CTC  TGT
215 ► Thr  Trp  Asp  Asp  Asp  Leu  Leu  Pro  Leu  Cys

2758  TCC  CAG  ATA  TTT  CGC  CGC  GAC  ATT  CGT  GCA
225 ► Ser  Gln  Ile  Phe  Arg  Arg  Asp  Ile  Arg  Ala

2788  TCG  TCA  GAA  CTG  ACA  CAG  GCC  GAA  GCA  GTA
235 ► Ser  Ser  Glu  Leu  Thr  Gln  Ala  Glu  Ala  Val

2818  AAA  GCT  CTT  GGA  TTC  CTG  AAA  CAG  AAA  GCC
245 ► Lys  Ala  Leu  Gly  Phe  Leu  Lys  Gln  Lys  Ala
                                          BglII Xhol 2848  GCA  GAG  CAG  AAG  GTG  GCA  GCA  TAGATCTCGAG
255 ► Ala  Glu  Gln  Lys  Val  Ala  Ala  • • •
```

Figure 14b (cont'd)

HindIII

2880 AAGCTTCCTGCTGAACATCAAAGGCAAGAAAACATCTGT

2919 TGTCAAAGACAGCATCCTTGAACAAGGACAATTAACAGT

2958 TAACAAATAAAAACGCAAAAGAAAATGCCGATATCCTAT

2997 TGGCATTTTCTTTTATTTCTTATCAACATAAAGGTGAAT

XhoI

3036 CCCATACCTCGAGCTTCACGCTGCCGCAAGCACTCAGGG

3075 CGCAAGGGCTGCTAAAAGGAAGCGGAACACGTAGAAAGC

3114 CAGTCCGCAGAAACGGTGCTGACCCCGGATGAATGTCAG

3153 CTACTGGGCTATCTGGACAAGGGAAAACGCAAGCGCAAA

3192 GAGAAAGCAGGTAGCTTGCAGTGGGCTTACATGGCGATA

3231 GCTAGACTGGGCGGTTTTATGGACAGCAAGCGAACCGGA

PvuII

3270 ATTGCCAGCTGGGGCGCCCTCTGGTAAGGTTGGGAAGCC

3309 CTGCAAAGTAAACTGGATGGCTTTCTTGCCGCCAAGGAT

BglII

3348 CTGATGGCGCAGGGGATCAAGATCTGATCAAGAGACAGG

3387 ATGAGGATCGTTTCGC ATG GAT ATT AAT ACT
                1▶Met Asp Ile Asn Thr

3418 GAA ACT GAG ATC AAG CAA AAG CAT TCA CTA
   6▶Glu Thr Glu Ile Lys Gln Lys His Ser Leu

3448 ACC CCC TTT CCT GTT TTC CTA ATC AGC CCG
  16▶Thr Pro Phe Pro Val Phe Leu Ile Ser Pro

3478 GCA TTT CGC GGG CGA TAT TTT CAC AGC TAT
  26▶Ala Phe Arg Gly Arg Tyr Phe His Ser Tyr

3508 TTC AGG AGT TCA GCC ATG AAC GCT TAT TAC
  36▶Phe Arg Ser Ser Ala Met Asn Ala Tyr Tyr

Figure 14b (cont'd)

```
3538 ATT CAG GAT CGT CTT GAG GCT CAG AGC TGG
  46▶Ile Gln Asp Arg Leu Glu Ala Gln Ser Trp

3568 GCG CGT CAC TAC CAG CAG CTC GCC CGT GAA
  56▶Ala Arg His Tyr Gln Gln Leu Ala Arg Glu

3598 GAG AAA GAG GCA GAA CTG GCA GAC GAC ATG
  66▶Glu Lys Glu Ala Glu Leu Ala Asp Asp Met

3628 GAA AAA GGC CTG CCC CAG CAC CTG TTT GAA
  76▶Glu Lys Gly Leu Pro Gln His Leu Phe Glu

3658 TCG CTA TGC ATC GAT CAT TTG CAA CGC CAC
  86▶Ser Leu Cys Ile Asp His Leu Gln Arg His

3688 GGG GCC AGC AAA AAA TCC ATT ACC CGT GCG
  96▶Gly Ala Ser Lys Lys Ser Ile Thr Arg Ala

3718 TTT GAT GAC GAT GTT GAG TTT CAG GAG CGC
 106▶Phe Asp Asp Asp Val Glu Phe Gln Glu Arg

3748 ATG GCA GAA CAC ATC CGG TAC ATG GTT GAA
 116▶Met Ala Glu His Ile Arg Tyr Met Val Glu

3778 ACC ATT GCT CAC CAC CAG GTT GAT ATT GAT
 126▶Thr Ile Ala His His Gln Val Asp Ile Asp
                                         HindIII
3808 TCA GAG GTA TAA AACGAGTAGA AGC TTG GCT
 136▶Ser Glu Val •••

3839 GTT TTG GCG GAT GAG AGA AGA TTT TCA GCC

3869 TGA TACAGATTAAATCAGAACGCAGAAGCGGTCTGATA

3907 AAACAGAATTTGCCTGGCGGCAGTAGCGCGGTGGTCCCA

3946 CCTGACCCCATGCCGAACTCAGAAGTGAAACGCCGTAGC

3985 GCCGATGGTAGTGTGGGTCTCCCCATGCGAGAGTAGGG
```

Figure 14b (cont'd)

```
4024 AACTGCCAGGCATCAAATAAAACGAAAGGCTCAGTCGAA
4063 AGACTGGGCCTTTCGTTTTATCTGTTGTTTGTCGGTGAA
4102 CGCTCTCCTGAGTAGGACAAATCCGCCGGGAGCGGATTT
4141 GAACGTTGCGAAGCAACGGCCCGGAGGGTGGCGGGCAGG
4180 ACGCCCGCCATAAACTGCCAGGCATCAAATTAAGCAGAA
4219 GGCCATCCTGACGGATGGCCTTTTTGCGTTTCTACAAAC
4258 TCTTTTGTTTATTTTTCTAAATACATTCAAATATGTATC
4297 CGCTCATGAGACAATAACCCTGATAAATGCTTCAATAAT
4336 ATTGAAAAGGAAGAGT ATG AGT ATT CAA CAT
                           1▶Met Ser Ile Gln His
4368 TTC CGT GTC GCC CTT ATT CCC TTT TTT GCG
    6▶Phe Arg Val Ala Leu Ile Pro Phe Phe Ala
4398 GCA TTT TGC CTT CCT GTT TTT GCT CAC CCA
   16▶Ala Phe Cys Leu Pro Val Phe Ala His Pro
4428 GAA ACG CTG GTG AAA GTA AAA GAT GCT GAA
   26▶Glu Thr Leu Val Lys Val Lys Asp Ala Glu
4458 GAT CAG TTG GGT GCA CGA GTG GGT TAC ATC
   36▶Asp Gln Leu Gly Ala Arg Val Gly Tyr Ile
4488 GAA CTG GAT CTC AAC AGC GGT AAG ATC CTT
   46▶Glu Leu Asp Leu Asn Ser Gly Lys Ile Leu
4518 GAG AGT TTT CGC CCC GAA GAA CGT TTT CCA
   56▶Glu Ser Phe Arg Pro Glu Glu Arg Phe Pro
4548 ATG ATG AGC ACT TTT AAA GTT CTG CTA TGT
   66▶Met Met Ser Thr Phe Lys Val Leu Leu Cys
```

Figure 14b (cont'd)

```
4578 GGC GCG GTA TTA TCC CGT GTT GAC GCC GGG
  76▶ Gly Ala Val Leu Ser Arg Val Asp Ala Gly
4608 CAA GAG CAA CTC GGT CGC CGC ATA CAC TAT
  86▶ Gln Glu Gln Leu Gly Arg Arg Ile His Tyr
                                        ScaI
4638 TCT CAG AAT GAC TTG GTT GAG TAC TCA CCA
  96▶ Ser Gln Asn Asp Leu Val Glu Tyr Ser Pro
4668 GTC ACA GAA AAG CAT CTT ACG GAT GGC ATG
 106▶ Val Thr Glu Lys His Leu Thr Asp Gly Met
4698 ACA GTA AGA GAA TTA TGC AGT GCT GCC ATA
 116▶ Thr Val Arg Glu Leu Cys Ser Ala Ala Ile
4728 ACC ATG AGT GAT AAC ACT GCG GCC AAC TTA
 126▶ Thr Met Ser Asp Asn Thr Ala Ala Asn Leu
4758 CTT CTG ACA ACG ATC GGA GGA CCG AAG GAG
 136▶ Leu Leu Thr Thr Ile Gly Gly Pro Lys Glu
4788 CTA ACC GCT TTT TTG CAC AAC ATG GGG GAT
 146▶ Leu Thr Ala Phe Leu His Asn Met Gly Asp
4818 CAT GTA ACT CGC CTT GAT CGT TGG GAA CCG
 156▶ His Val Thr Arg Leu Asp Arg Trp Glu Pro
4848 GAG CTG AAT GAA GCC ATA CCA AAC GAC GAG
 166▶ Glu Leu Asn Glu Ala Ile Pro Asn Asp Glu
4878 CGT GAC ACC ACG ATG CCT GTA GCA ATG GCA
 176▶ Arg Asp Thr Thr Met Pro Val Ala Met Ala
4908 ACA ACG TTG CGC AAA CTA TTA ACT GGC GAA
 186▶ Thr Thr Leu Arg Lys Leu Leu Thr Gly Glu
4938 CTA CTT ACT CTA GCT TCC CGG CAA CAA TTA
 196▶ Leu Leu Thr Leu Ala Ser Arg Gln Gln Leu
```

Figure 14b (cont'd)

```
4968  ATA GAC TGG ATG GAG GCG GAT AAA GTT GCA
206▶  Ile Asp Trp Met Glu Ala Asp Lys Val Ala

4998  GGA CCA CTT CTG CGC TCG GCC CTT CCG GCT
216▶  Gly Pro Leu Leu Arg Ser Ala Leu Pro Ala

5028  GGC TGG TTT ATT GCT GAT AAA TCT GGA GCC
226▶  Gly Trp Phe Ile Ala Asp Lys Ser Gly Ala

5058  GGT GAG CGT GGG TCT CGC GGT ATC ATT GCA
236▶  Gly Glu Arg Gly Ser Arg Gly Ile Ile Ala

5088  GCA CTG GGG CCA GAT GGT AAG CCC TCC CGT
246▶  Ala Leu Gly Pro Asp Gly Lys Pro Ser Arg

5118  ATC GTA GTT ATC TAC ACG ACG GGG AGT CAG
256▶  Ile Val Val Ile Tyr Thr Thr Gly Ser Gln

5148  GCA ACT ATG GAT GAA CGA AAT AGA CAG ATC
266▶  Ala Thr Met Asp Glu Arg Asn Arg Gln Ile

5178  GCT GAG ATA GGT GCC TCA CTG ATT AAG CAT
276▶  Ala Glu Ile Gly Ala Ser Leu Ile Lys His

5208  TGG TAA CTGTCAGACCAAGTTTACTCATATATACTTT
286▶  Trp ···

5245  AGATTGATTTACGCGCCCTGTAGCGGCGCATTAAGCGCG

5284  GCGGGTGTGGTGGTTACGCGCAGCGTGACCGCTACACTT

5323  GCCAGCGCCCTAGCGCCCGCTCCTTTCGCTTTCTTCCCT

5362  TCCTTTCTCGCCACGTTCGCCGGCTTTCCCCGTCAAGCT

5401  CTAAATCGGGGGCTCCCTTTAGGGTTCCGATTTAGTGCT

5440  TTACGGCACCTCGACCCCAAAAAACTTGATTTGGGTGAT

5479  GGTTCACGTAGTGGGCCATCGCCCTGATAGACGGTTTTT
```

Figure 14b (cont'd)

| | |
|---|---|
| 5518 | CGCCCTTTGACGTTGGAGTCCACGTTCTTTAATAGTGGA |
| 5557 | CTCTTGTTCCAAACTTGAACAACACTCAACCCTATCTCG |
| 5596 | GGCTATTCTTTTGATTTATAAGGGATTTTGCCGATTTCG |
| 5635 | GCCTATTGGTTAAAAAATGAGCTGATTTAACAAAAATTT |
| 5674 | AACGCGAATTTTAACAAAATATTAACGTTTACAATTTAA |
| 5713 | AAGGATCTAGGTGAAGATCCTTTTTGATAATCTCATGAC |
| 5752 | CAAAATCCCTTAACGTGAGTTTTCGTTCCACTGAGCGTC |
| 5791 | AGACCCCGTAGAAAAGATCAAAGGATCTTCTTGAGATCC |
| 5830 | TTTTTTTCTGCGCGTAATCTGCTGCTTGCAAACAAAAAA |
| 5869 | ACCACCGCTACCAGCGGTGGTTTGTTTGCCGGATCAAGA |
| 5908 | GCTACCAACTCTTTTTCCGAAGGTAACTGGCTTCAGCAG |
| 5947 | AGCGCAGATACCAAATACTGTCCTTCTAGTGTAGCCGTA |
| 5986 | GTTAGGCCACCACTTCAAGAACTCTGTAGCACCGCCTAC |
| 6025 | ATACCTCGCTCTGCTAATCCTGTTACCAGTGGCTGCTGC |
| 6064 | CAGTGGCGATAAGTCGTGTCTTACCGGGTTGGACTCAAG |
| 6103 | ACGATAGTTACCGGATAAGGCGCAGCGGTCGGGCTGAAC |
| 6142 | GGGGGGTTCGTGCACACAGCCCAGCTTGGAGCGAACGAC |
| 6181 | CTACACCGAACTGAGATACCTACAGCGTGAGCTATGAGA |
| 6220 | AAGCGCCACGCTTCCCGAAGGGAGAAAGGCGGACAGGTA |
| 6259 | TCCGGTAAGCGGCAGGGTCGGAACAGGAGAGCGCACGAG |
| 6298 | GGAGCTTCCAGGGGGAAACGCCTGGTATCTTTATAGTCC |
| 6337 | TGTCGGGTTTCGCCACCTCTGACTTGAGCGTCGATTTTT |

Figure 14b (cont'd)

```
6376 GTGATGCTCGTCAGGGGGGCGGAGCCTATGGAAAAACGC
6415 CAGCAACGCGGCCTTTTTACGGTTCCTGGCCTTTTGCTG
6454 GCCTTTTGCTCACATGTTCTTTCCTGCGTTATCCCCTGA
6493 TTCTGTGGATAACCGTATTACCGCCTTTGAGTGAGCTGA
6532 TACCGCTCGCCGCAGCCGAACGACCGAGCGCAGCGAGTC
6571 AGTGAGCGAGGAAGCGGAAGAGCGCCTGATGCGGTATTT
6610 TCTCCTTACGCATCTGTGCGGTATTTCACACCGCATAGG
6649 GTCATGGCTGCGCCCCGACACCCGCCAACACCCGCTGAC
6688 GCGCCCTGACGGGCTTGTCTGCTCCCGGCATCCGCTTAC
6727 AGACAAGCTGTGACCGTCTCCGGGAGCTGCATGTGTCAG
6766 AGGTTTTCACCGTCATCACCGAAACGCGCGAGGCAGCAA
6805 GGAGATGGCGCCCAACAGTCCCCCGGCCACGGGGCCTGC
6844 CACCATACCCACGCCGAAACAAGCGCTCATGAGCCCGAA
6883 GTGGCGAGCCCGATCTTCCCCATCGGTGATGTCGGCGAT
6922 ATAGGCGCCAGCAACCGCACCTGTGGCGCCGGTGATGCC
6961 GGCCACGATGCGTCCGGCGTAGAGGATCTGCTCATGTTT
7000 GACAGCTTATC
```

DNA CLONING METHOD

This application is a divisional of U.S. Ser. No. 10/231,013, filed Aug. 30, 2002, and issued as U.S. Pat. No. 6,787,316 on Sep. 7, 2004, which is a divisional application of U.S. Ser. No. 09/555,510, filed Jun. 5, 2000 and issued as U.S. Pat. No. 6,509,156 on Jan. 21, 2003, which is a 371 of PCT/EP98/07945 filed Dec. 7, 1998, which claims priority of EP 98 118 756.0 filed Oct. 5, 1998 and EP 97 121 462.2 filed Dec. 5, 1997. The disclosure of the prior application(s) is hereby incorporated by reference herein in their entirety.

DESCRIPTION

The invention refers to a novel method for cloning DNA molecules using a homologous recombination mechanism between at least two DNA molecules. Further, novel reagent kits suitable for DNA cloning are provided.

Current methods for cloning foreign DNA in bacterial cells usually comprise the steps of providing a suitable bacterial vector, cleaving said vector with a restriction enzyme and in vitro-inserting a foreign DNA fragment in said vector. The resulting recombinant vectors are then used to transform bacteria. Although such cloning methods have been used successfully for about 20 years they suffer from several drawbacks. These drawbacks are, in particular, that the in vitro steps required for inserting foreign DNA in a vector are often very complicated and time-consuming, if no suitable restriction sites are available on the foreign DNA or the vector.

Furthermore, current methods usually rely on the presence of suitable restriction enzyme cleavage sites in the vector into which the foreign DNA fragment is placed. This imposes two limitations on the final cloning product. First, the foreign DNA fragment can usually only be inserted into the vector at the position of such a restriction site or sites. Thus, the cloning product is limited by the disposition of suitable restriction sites and cloning into regions of the vector where there is no suitable restriction site, is difficult and often imprecise. Second, since restriction sites are typically 4 to 8 base pairs in length, they occur a multiple number of times as the size of the DNA molecules being used increases. This represents a practical limitation to the size of the DNA molecules that can be manipulated by most current cloning techniques. In particular, the larger sizes of DNA cloned into vectors such as cosmids, BACs, PACs and P1 s are such that it is usually impractical to manipulate them directly by restriction enzyme based techniques. Therefore, there is a need for providing a new cloning method, from which the drawbacks of the prior art have at least partly been eliminated.

According to the present invention it was found that an efficient homologous recombination mechanism between two DNA molecules occurs at usable frequencies in a bacterial host cell which is capable of expressing the products of the recE and recT genes or functionally related genes such as the redα and redβ genes, or the phage P22 recombination system (Kolodner et al., Mol. Microbiol. 11(1994) 23-30; Fenton, A. C. and Poteete, A. R., Virology 134 (1984)148-160; Poteete, A. R. and Fenton, A. C., Virology 134 (1984) 161-167). This novel method of cloning DNA fragments is termed "ET cloning".

The identification and characterization of the E. coli RecE and RecT proteins is described Gillen et al. (J. Bacteriol. 145 (1981), 521-532) and Hall et al. (J. Bacteriol. 175 (1993), 277-287). Hall and Kolodner (Proc. Natl. Acad. Sci. USA 91 (1994), 3205-3209) disclose in vitro homologous pairing and strand exchange of linear double-stranded DNA and homologous circular single-stranded DNA promoted by the RecT protein. Any references to the use of this method for the cloning of DNA molecules in cells cannot be found therein.

The recET pathway of genetic recombination in E. coli is known (Hall and Kolodner (1994), supra; Gillen et al. (1981), supra). This pathway requires the expression of two genes, recE and recT. The DNA sequence of these genes has been published (Hall et al., supra). The RecE protein is similar to bacteriophage proteins, such as λ exo or λ Redα (Gillen et al., J. Mol. Biol. 113 (1977), 27-41; Little, J. Biol. Chem. 242 (1967), 679-686; Radding and Carter, J. Biol. Chem. 246 (1971), 2513-2518; Joseph and Kolodner, J. Biol. Chem. 258 (1983), 10418-10424). The RecT protein is similar to bacteriophage proteins, such as λ β-protein or λ Redβ (Hall et al. (1993), supra; Muniyappa and Radding, J. Biol. Chem. 261 (1986), 7472-7478; Kmiec and Hollomon, J. Biol. Chem. 256 (1981), 12636-12639). The content of the above-cited documents is incorporated herein by reference.

Oliner et al. (Nucl. Acids Res. 21 (1993), 5192-5197) describe in vivo cloning of PCR products in E. coli by intermolecular homologous recombination between a linear PCR product and a linearized plasmid vector. Other previous attempts to develop new cloning methods based on homologous recombination in prokaryotes, too, relied on the use of restriction enzymes to linearise the vector (Bubeck et al., Nucleic Acids Res. 21 (1993), 3601-3602; Oliner et al., Nucleic Acids Res. 21 (1993), 5192-5197; Degryse, Gene 170 (1996), 45-50) or on the host-specific recA-dependent recombination system (Hamilton et al., J. Bacteriol. 171 (1989), 4617-4622; Yang et al., Nature Biotech. 15 (1997), 859-865; Dabert and Smith, Genetics 145 (1997), 877-889). These methods are of very limited applicability and are hardly used in practice.

The novel method of cloning DNA according to the present invention does not require in vitro treatments with restriction enzymes or DNA ligases and is therefore fundamentally distinct from the standard methodologies of DNA cloning. The method relies on a pathway of homologous recombination in E. coli involving the recE and recT gene products, or the redα and redβ gene products, or functionally equivalent gene products. The method covalently combines one preferably linear and preferably extrachromosomal DNA fragment, the DNA fragment to be cloned, with one second preferably circular DNA vector molecule, either an episome or the endogenous host chromosome or chromosomes. It is therefore distinct from previous descriptions of cloning in E. coli by homologous recombination which either rely on the use of two linear DNA fragments or different recombination pathways.

The present invention provides a flexible way to use homologous recombination to engineer large DNA molecules including an intact >76 kb plasmid and the E. coli chromosome. Thus, there is practically no limitation of target choice either according to size or site. Therefore, any recipient DNA in a host cell, from high copy plasmid to the genome, is amenable to precise alteration. In addition to engineering large DNA molecules, the invention outlines new, restriction enzyme-independent approaches to DNA design. For example, deletions between any two chosen base pairs in a target episome can be made by choice of oligonucleotide homology arms. Similarly, chosen DNA sequences can be inserted at a chosen base pair to create, for example, altered protein reading frames. Concerted combinations of insertions and deletions, as well as point mutations, are also possible. The application of these strategies is particularly relevant to complex or difficult DNA constructions, for example, those intended for homologous recombinations in eukaryotic cells, e.g. mouse embryonic stem cells. Further, the present invention provides a simple way to position site specific recombination target sites exactly where desired. This will simplify applications of site specific recombination in other living systems, such as plants and mice.

A subject matter of the present invention is a method for cloning DNA molecules in cells comprising the steps:
a) providing a host cell capable of performing homologous recombination,
b) contacting in said host cell a first DNA molecule which is capable of being replicated in said host cell with a second DNA molecule comprising at least two regions of sequence homology to regions on the first DNA molecule, under conditions which favour homologous recombination between said first and second DNA molecules and
c) selecting a host cell in which homologous recombination between said first and second DNA molecules has occurred.

In the method of the present invention the homologous recombination preferably occurs via the recET mechanism, i.e. the homologous recombination is mediated by the gene products of the recE and the recT genes which are preferably selected from the *E. coli* genes recE and recT or functionally related genes such as the phage λ redα and redβ genes.

The host cell suitable for the method of the present invention preferably is a bacterial cell, e.g. a gram-negative bacterial cell. More preferably, the host cell is an enterobacterial cell, such as Salmonella, Klebsiella or Escherichia. Most preferably the host cell is an *Escherichia coli* cell. It should be noted, however, that the cloning method of the present invention is also suitable for eukaryotic cells, such as fungi, plant or animal cells.

Preferably, the host cell used for homologous recombination and propagation of the cloned. DNA can be any cell, e.g. a bacterial strain in which the products of the recE and recT, or redα and redβ, genes are expressed. The host cell may comprise the recE and recT genes located on the host cell chromosome or on non-chromosomal DNA, preferably on a vector, e.g. a plasmid. In a preferred case, the RecE and RecT, or Redα and Redβ, gene products are expressed from two different regulatable promoters, such as the arabinose-inducible BAD promoter or the lac promoter or from non-regulatable promoters. Alternatively, the recE and recT, or redα and redβ, genes are expressed on a polycistronic mRNA from a single regulatable or non-regulatable promoter. Preferably the expression is controlled by regulatable promoters.

Especially preferred is also an embodiment, wherein the recE or redα gene is expressed by a regulatable promoter. Thus, the recombinogenic potential of the system is only elicited when required and, at other times, possible undesired recombination reactions are limited. The recT or redβ gene, on the other hand, is preferably overexpressed with respect to recE or redα. This may be accomplished by using a strong constitutive promoter, e.g. the
EM7 promoter and/or by using a higher copy number of recT, or redβ, versus recE, or redα, genes.

For the purpose of the present invention any recE and recT genes are suitable insofar as they allow a homologous recombination of first and second DNA molecules with sufficient efficiency to give rise to recombination products in more than 1 in $10^9$ cells transfected with DNA. The recE and recT genes may be derived from any bacterial strain or from bacteriophages or may be mutants and variants thereof. Preferred are recE and recT genes which are derived from *E. coli* or from *E. coli* bacteriophages, such as the redα and redβ genes from lambdoid phages, e.g. bacteriophage λ.

Figure 7A:
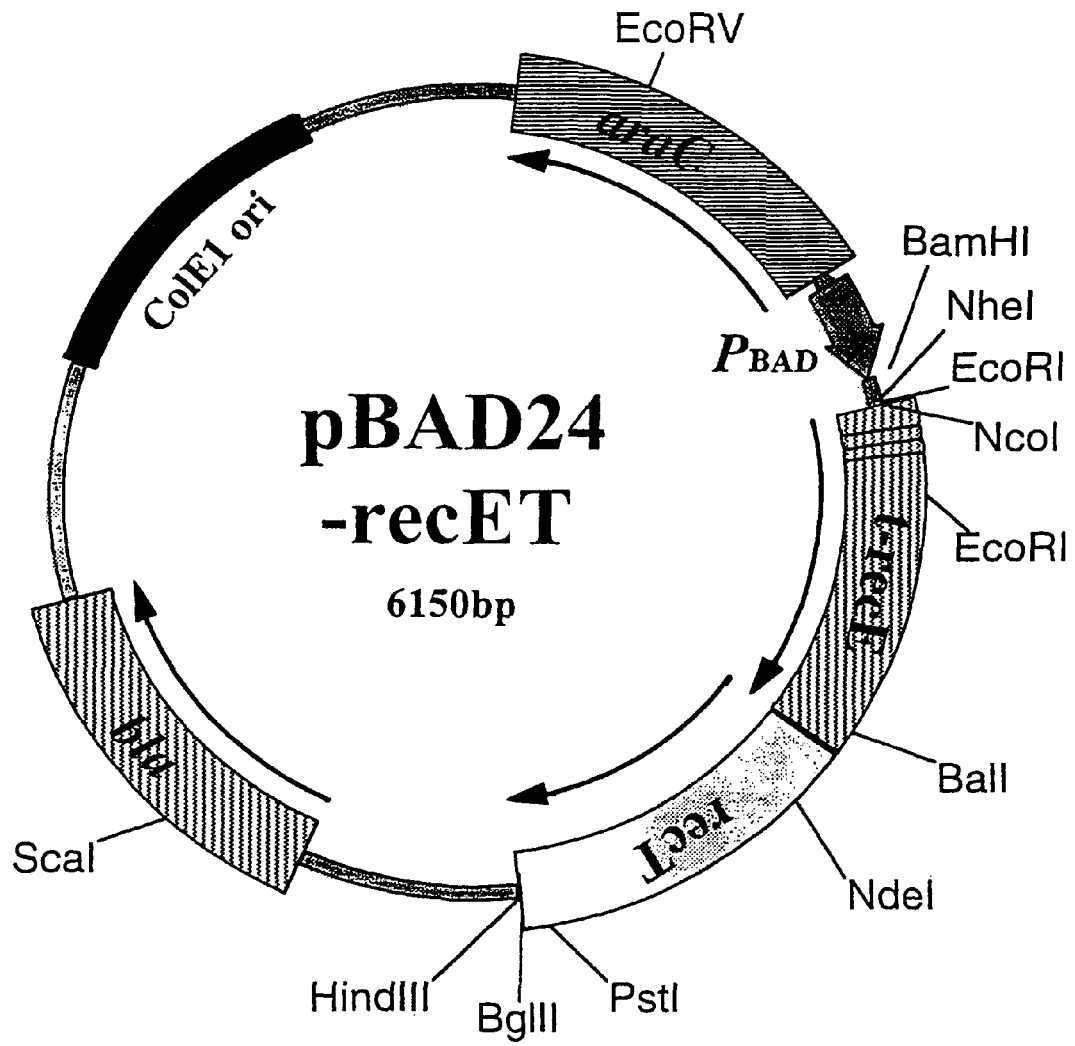

More preferably, the recE or redα gene is selected from a nucleic acid molecule comprising (a) the nucleic acid sequence from position 1320 (ATG) to 2159 (GAC) as depicted in FIG. 7B or SEQ ID No. 2,
(b) the nucleic acid sequence from position 1320 (ATG) to 1998 (CGA) as depicted in FIG. 14B or SEQ ID No. 11,
(c) a nucleic acid encoding the same polypeptide within the degeneracy of the genetic code and/or
(d) a nucleic acid sequence which hybridizes under stringent conditions with the nucleic acid sequence from (a), (b) and/or (c).

More preferably, the recT or redβ gene is selected from a nucleic acid molecule comprising
(a) the nucleic acid sequence from position 2155 (ATG) to 2961 (GAA) as depicted in FIG. 7B or SEQ ID No. 4,
(b) the nucleic acid sequence from position 2086 (ATG) to 2868 (GCA) as depicted in FIG. 14B or SEQ ID No. 11,
(c) a nucleic acid encoding the same polypeptide within the degeneracy of the genetic code and/or
(d) a nucleic acid sequence which hybridizes under stringent conditions with the nucleic acid sequences from (a), (b) and/or (c).

It should be noted that the present invention also encompasses mutants and variants of the given sequences, e.g. naturally occurring mutants and variants or mutants and variants obtained by genetic engineering. Further it should be noted that the recE gene depicted in FIG. 7B is an already truncated gene encoding amino acids 588-866 of the native protein. Mutants and variants preferably have a nucleotide sequence identity of at least 60%, preferably of at least 70% and more preferably of at least 80% of the recE and recT sequences depicted in FIGS. 7B and 13B, and of the redα and redβ sequences depicted in FIG. 14B.

According to the present invention hybridization under stringent conditions preferably is defined according to Sambrook et al. (1989), infra, and comprises a detectable hybridization signal after washing for 30 min in 0.1×SSC, 0.5% SDS at 55° C., preferably at 62° C. and more preferably at 68° C.

In a preferred case the recE and recT genes are derived from the corresponding endogenous genes present in the *E. coli* K12 strain and its derivatives or from bacteriophages. in particular, strains that carry the sbcA mutation are suitable. Examples of such strains are JC 8679 and JC 9604 (Gillen et al. (1981), supra). Alternatively, the corresponding genes may also be obtained from other coliphages such as lambdoid phages or phage P22.

The genotype of JC 8679 and JC 9604 is Sex (Hfr, F+, F−, or F''): F−.JC 8679 comprises the mutations: recBC 21, recC 22, sbcA 23, thr-1, ara-14, leu B 6, DE (gpt-proA) 62, lacY1, tsx-33, gluV44 (AS), galK2 (Oc), LAM-, his-60, relA 1, rps L31 (strR), xyl A5, mtl-1, argE3 (Oc) and thi-1. JC 9604 comprises the same mutations and further the mutation recA 56.

Further, it should be noted that the recE and recT, or redα and redβ, genes can be isolated from a first donor source, e.g. a donor bacterial cell and transformed into a second receptor source, e.g. a receptor bacterial or eukaryotic cell in which they are expressed by recombinant DNA means.

In one embodiment of the invention, the host cell used is a bacterial strain having an sbcA mutation, e.g. one of *E. coli* strains JC 8679 and JC 9604 mentioned above. However, the method of the invention is not limited to host cells having an sbcA mutation or analogous cells. Surprisingly, it has been found that the cloning method of the invention also works in cells without sbcA mutation, whether recBC+ or recBC−, e.g. also in prokaryotic recBC+ host cells, e.g. in *E. coli* recBC+ cells. In that case preferably those host cells are used in which the product of a recBC type exonuclease inhibitor gene is expressed. Preferably, the exonuclease inhibitor is capable of inhibiting the host recBC system or an equivalent thereof. A suitable example of such exonuclease inhibitor gene is the λ redγ gene (Murphy, J. Bacteriol. 173 (1991), 5808-5821) and functional equivalents thereof, respectively, which, for example, can be obtained from other coliphages such as from phage P22 (Murphy, J. Biol. Chem. 269 (1994), 22507-22516).

Figure 13:
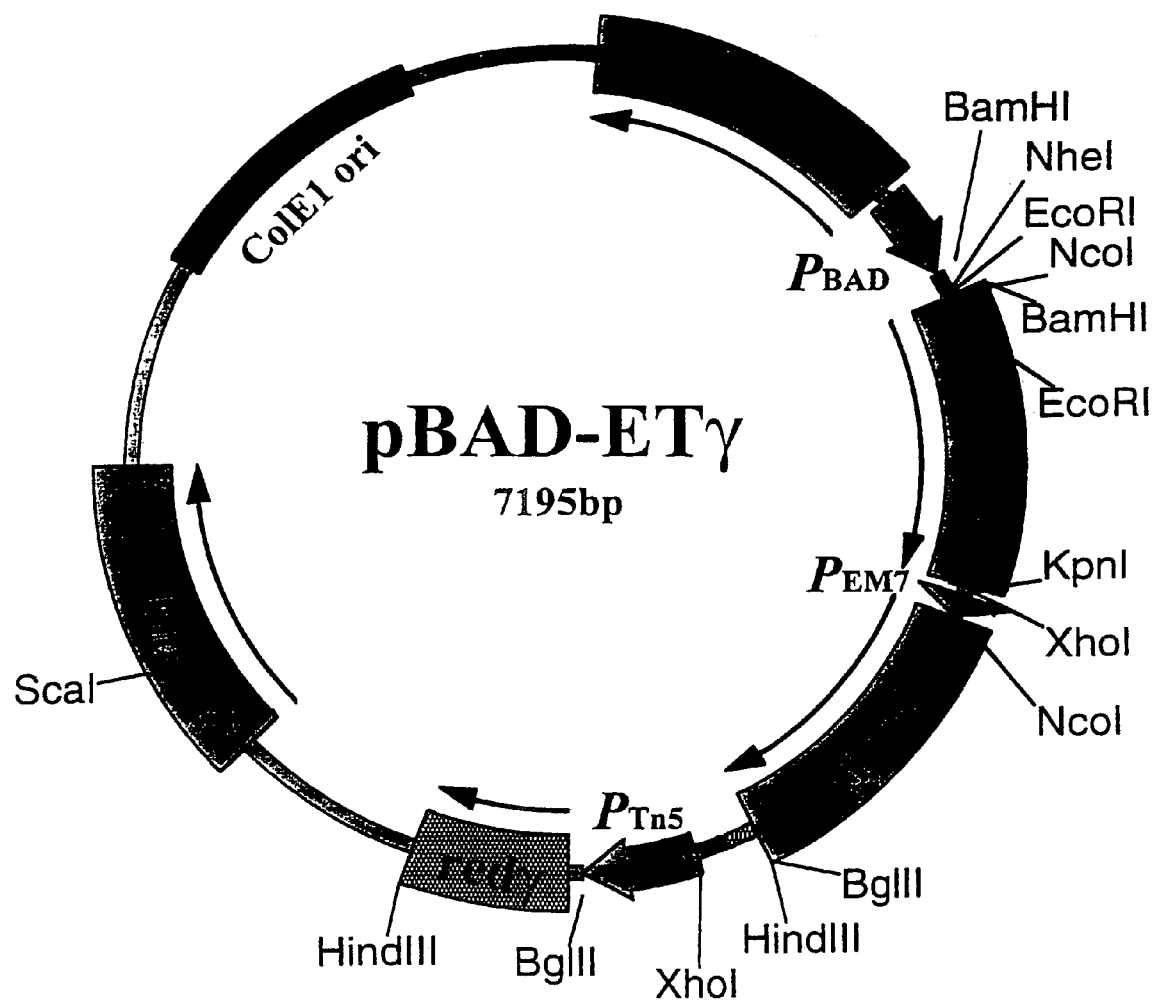
Figure 13B:

More preferably, the exonuclease inhibitor gene is selected from a nucleic acid molecule comprising
(a) the nucleic acid sequence from position 3588 (ATG) to 4002 (GTA) as depicted in FIG. 13B or SEQ ID No. 10 or 11,
(b) a nucleic acid encoding the same polypeptide within the degeneracy of the genetic code and/or
(c) a nucleic acid sequence which hybridizes under stringent conditions as defined above with the nucleic acid sequence from (a) and/or (b).

Surprisingly, it has been found that the expression of an exonuclease inhibitor gene in both recBC+ and recBC− strains leads to significant improvement of cloning efficiency.

The cloning method according to the present invention employs a homologous recombination between a first DNA molecule and a second DNA molecule. The first DNA molecule can be any DNA molecule that carries an origin of replication which is operative in the host cell, e.g. an E. coli replication origin. Further, the first DNA molecule is present in a form which is capable of being replicated in the host cell. The first DNA molecule, i.e. the vector, can be any extrachromosomal DNA molecule containing an origin of replication which is operative in said host cell, e.g. a plasmid including single, low, medium or high copy plasmids or other extrachromosomal circular DNA molecules based on cosmid, P1, BAC or PAC vector technology. Examples of such vectors are described, for example, by Sambrook et al. (Molecular Cloning, Laboratory Manual, 2nd Edition (1989), Cold Spring Harbor Laboratory Press) and loannou et al. (Nature Genet. 6 (1994), 84-89) or references cited therein. The first DNA molecule can also be a host cell chromosome, particularly the E. coli chromosome. Preferably, the first DNA molecule is a double-stranded DNA molecule.

The second DNA molecule is preferably a linear DNA molecule and comprises at least two regions of sequence homology, preferably of sequence identity to regions on the first DNA molecule. These homology or identity regions are preferably at least 15 nucleotides each, more preferably at least 20 nucleotides and, most preferably, at least 30 nucleotides each. Especially good results were obtained when using sequence homology regions having a length of about 40 or more nucleotides, e.g. 60 or more nucleotides. The two sequence homology regions can be located on the linear DNA fragment so that one is at one end and the other is at the other end, however they may also be located internally. Preferably, also the second DNA molecule is a double-stranded DNA molecule.

The two sequence homology regions are chosen according to the experimental design. There are no limitations on which regions of the first DNA molecule can be chosen for the two sequence homology regions located on the second DNA molecule, except that the homologous recombination event cannot delete the origin of replication of the first DNA molecule. The sequence homology regions can be interrupted by non-identical sequence regions as long as sufficient sequence homology is retained for the homologous recombination reaction. By using sequence homology arms having non-identical sequence regions compared to the target site mutations such as substitutions, e.g. point mutations, insertions and/or deletions may be introduced into the target site by ET cloning.

The second foreign DNA molecule which is to be cloned in the bacterial cell may be derived from any source. For example, the second DNA molecule may be synthesized by a nucleic acid amplification reaction such as a PCR where both of the DNA oligonucleotides used to prime the amplification contain in addition to sequences at the 3'-ends that serve as a primer for the amplification, one or the other of the two homology regions. Using oligonucleotides of this design, the DNA product of the amplification can be any DNA sequence suitable for amplification and will additionally have a sequence homology region at each end.

A specific example of the generation of the second DNA molecule is the amplification of a gene that serves to convey a phenotypic difference to the bacterial host cells, in particular, antibiotic resistance. A simple variation of this procedure involves the use of oligonucleotides that include other sequences in addition to the PCR primer sequence and the sequence homology region. A further simple variation is the use of more than two amplification primers to generate the amplification product. A further simple variation is the use of more than one amplification reaction to generate the amplification product. A further variation is the use of DNA fragments obtained by methods other than PCR, for example, by endonuclease or restriction enzyme cleavage to linearize fragments from any source of DNA.

It should be noted that the second DNA molecule is not necessarily a single species of DNA molecule. It is of course possible to use a heterogenous population of second DNA molecules, e.g. to generate a DNA library, such as a genomic or cDNA library.

The method of the present invention may comprise the contacting of the first and second DNA molecules in vivo. In one embodiment of the present invention the second DNA fragment is transformed into a bacterial strain that already harbors the first vector DNA molecule. In a different embodiment, the second DNA molecule and the first DNA molecule are mixed together in vitro before co-transformation in the bacterial host cell. These two embodiments of the present invention are schematically depicted in FIG. 1. The method of transformation can be any method known in the art (e.g. Sambrook et al. supra). The preferred method of transformation or co-transformation, however, is electroporation.

Figure 2:
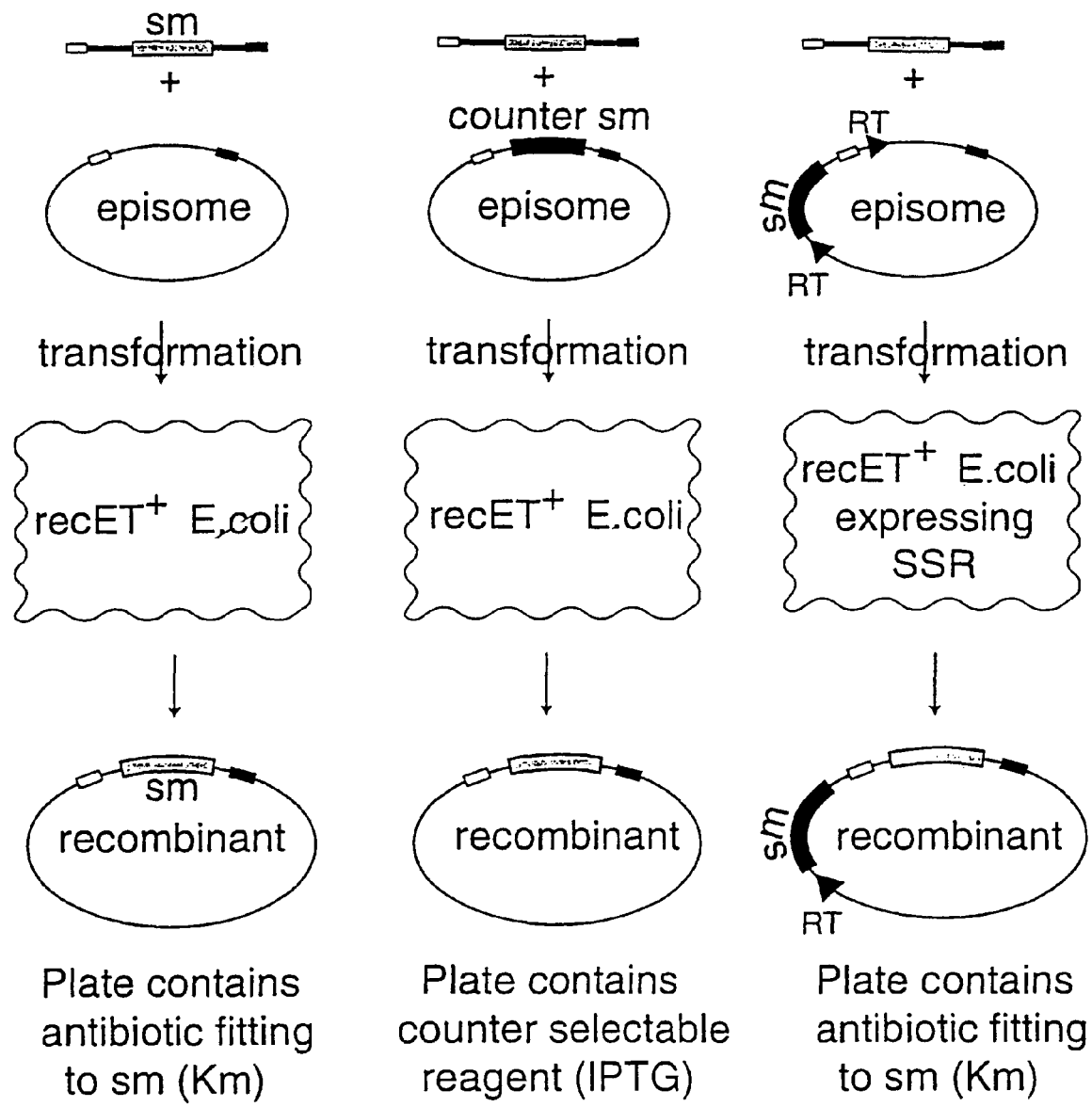

After contacting the first and second DNA molecules under conditions which favour homologous recombination between first and second DNA molecules via the ET cloning mechanism a host cell is selected, in which homologous recombination between said first and second DNA molecules has occurred. This selection procedure can be carried out by several different methods. In the following three preferred selection methods are depicted in FIG. 2 and described in detail below.

In a first selection method a second DNA fragment is employed which carries a gene for a marker placed between the two regions of sequence homology wherein homologous recombination is detectable by expression of the marker gene. The marker gene may be a gene for a phenotypic marker which is not expressed in the host or from the first DNA molecule. Upon recombination by ET cloning, the change in phenotype of the host strain conveyed by the stable acquisition of the second DNA fragment identifies the ET cloning product.

In a preferred case, the phenotypic marker is a gene that conveys resistance to an antibiotic, in particular, genes that convey resistance to kanamycin, ampillicin, chloramphenicol, tetracyclin or any other substance that shows bacteriocidal or bacteriostatic effects on the bacterial strain employed.

A simple variation is the use of a gene that complements a deficiency present within the bacterial host strain employed. For example, the host strain may be mutated so that it is incapable of growth without a metabolic supplement. In the absence of this supplement, a gene on the second DNA fragment can complement the mutational defect thus permitting growth. Only those cells which contain the episome carrying the intended DNA rearrangement caused by the ET cloning step will grow.

In another example, the host strain carries a phenotypic marker gene which is mutated so that one of its codons is a stop codon that truncates the open reading frame. Expression of the full length protein from this phenotypic marker gene requires the introduction of a suppressor tRNA gene which, once expressed, recognizes the stop codon and permits translation of the full open reading frame. The suppressor tRNA gene is introduced by the ET cloning step and successful recombinants identified by selection for, or identification of, the expression of the phenotypic marker gene. In these cases, only those cells which contain the intended DNA rearrangement caused by the ET cloning step will grow.

A further simple variation is the use of a reporter gene that conveys a readily detectable change in colony colour or morphology. In a preferred case, the green fluorescence protein (GFP) can be used and colonies carrying the ET cloning product identified by the fluorescence emissions of GFP. In another preferred case, the lacZ gene can be used and colonies carrying the ET cloning product identified by a blue colony colour when X-gal is added to the culture medium.

In a second selection method the insertion of the second DNA fragment into the first DNA molecule by ET cloning alters the expression of a marker present on the first DNA molecule. In this embodiment the first DNA molecule contains at least one marker gene between the two regions of sequence homology and homologous recombination may be detected by an altered expression, e.g. lack of expression of the marker gene.

In a preferred application, the marker present on the first DNA molecule is a counter-selectable gene product, such as the sacB, ccdB or tetracycline-resistance genes. In these cases, bacterial cells that carry the first DNA molecule unmodified by the ET cloning step after transformation with the second DNA fragment, or co-transformation with the second DNA fragment and the first DNA molecule, are plated onto a medium so the expression of the counter-selectable marker conveys a toxic or bacteriostatic effect on the host. Only those bacterial cells which contain the first DNA molecule carrying the intended DNA rearrangement caused by the ET cloning step will grow.

In another preferred application, the first DNA molecule carries a reporter gene that conveys a readily detectable change in colony colour or morphology. In a preferred case, the green fluorescence protein (GFP) can be present on the first DNA molecule and colonies carrying the first DNA molecule with or without the ET cloning product can be distinguished by differences in the fluorescence emissions of GFP. In another preferred case, the lacZ gene can be present on the first DNA molecule and colonies carrying the first DNA molecule with or without the ET cloning product identified by a blue or white colony colour when X-gal is added to the culture medium.

In a third selection method the integration of the second DNA fragment into the first DNA molecule by ET cloning removes a target site for a site specific recombinase, termed here an RT (for recombinase target) present on the first DNA molecule between the two regions of sequence homology. A homologous recombination event may be detected by removal of the target site.

In the absence of the ET cloning product, the RT is available for use by the corresponding site specific recombinase. The difference between the presence or not of this RT is the basis for selection of the ET cloning product. In the presence of this RT and the corresponding. site specific recombinase, the site specific recombinase mediates recombination at this RT and changes the phenotype of the host so that it is either not able to grow or presents a readily observable phenotype. In the absence of this RT, the corresponding site specific recombinase is not able to mediate recombination.

In a preferred case, the first DNA molecule to which the second DNA fragment is directed, contains two RTs, one of which is adjacent to, but not part of, an antibiotic resistance gene. The second DNA fragment is directed, by design, to remove this RT. Upon exposure to the corresponding site specific recombinase, those first DNA molecules that do not carry the ET cloning product will be subject to a site specific recombination reaction between the RTs that remove the antibiotic resistance gene and therefore the first DNA molecule fails to convey resistance to the corresponding antibiotic. Only those first DNA molecules that contain the ET cloning product, or have failed to be site specifically recombined for some other reason, will convey resistance to the antibiotic.

In another preferred case, the RT to be removed by ET cloning of the second DNA fragment is adjacent to a gene that complements a deficiency present within the host strain employed. In another preferred case, the RT to be removed by ET cloning of the second DNA fragment is adjacent to a reporter gene that conveys a readily detectable change in colony colour or morphology.

In another preferred case, the RT to be removed by ET cloning of the second DNA fragment is anywhere on a first episomal DNA molecule and the episome carries an origin of replication incompatible with survival of the bacterial host cell if it is integrated into the host genome. In this case the host genome carries a second RT, which may or may not be a mutated RT so that the corresponding site specific recombinase can integrate the episome, via its RT, into the RT sited in the host genome. Other preferred. RTs include RTs for site specific recombinases of the resolvase/transposase class. RTs include those described from existing examples of site specific recombination as well as natural or mutated variations thereof.

The preferred site specific recombinases include Cre, FLP, Kw or any site specific recombinase of the integrase class. Other preferred site specific recombinases include site specific recombinases of the resolvase/transposase class.

There are no limitations on the method of expression of the site specific recombinase in the host cell. In a preferred method, the expression of the site specific recombinase is regulated so that expression can be induced and quenched according to the optimisation of the ET cloning efficiency. In this case, the site specific recombinase gene can be either integrated into the host genome or carried on an episome. In another preferred case, the site specific recombinase is expressed from an episome that carries a conditional origin of replication so that it can be eliminated from the host cell.

In another preferred case, at least two of the above three selection methods are combined. A particularly preferred case involves a two-step use of the first selection method above, followed by use of the second selection method. This combined use requires, most simply, that the DNA fragment to be cloned includes a gene, or genes that permits the identification, in the first step, of correct ET cloning products by the acquisition of a phenotypic change. In a second step, expression of the gene or genes introduced in the first step is altered so that a second round of ET cloning products can be identified. In a preferred example, the gene employed is the tetracycline resistance gene and the first step ET cloning products are identified by the acquisition of tetracycline resistance. In the second step, loss of expression of the tetracycline gene is identified by loss of sensitivity to nickel chloride, fusaric acid or any other agent that is toxic to the host cell when the tetracycline gene is expressed. This two-step procedure permits the identification of ET cloning products by first the integration of a gene that conveys a phenotypic change on the host, and second by the loss of a related phenotypic change, most simply by removal of some of the DNA sequences integrated in the first step. Thereby the genes used to identify ET cloning products can be inserted and then removed to leave ET cloning products that are free of these genes.

In a further embodiment of the present invention the ET cloning may also be used for a recombination method comprising the steps of a) providing a source of RecE and RecT, or Redα and Redβ, proteins, b) contacting a first DNA molecule which is capable of being replicated in a suitable host cell with a second DNA molecule comprising at least two regions of sequence homology to regions on the first DNA molecule, under conditions which favour homologous recombination between said first and second DNA molecules and c) selecting DNA molecules in which a homologous recombination between said first and second DNA molecules has occurred.

The source of RecE and RecT, or Redα and Redβ, proteins may be either purified or partially purified RecE and RecT, or Redα and Redβ, proteins or cell extracts comprising RecE and RecT, or Redα and Redβ, proteins.

The homologous recombination event in this embodiment may occur in vitro, e.g. when providing a cell extract containing further components required for homologous recombination. The homologous recombination event, however, may also occur in vivo, e.g. by introducing RecE and RecT, or Redα and Redβ, proteins or the extract in a host cell (which may be recET positive or not, or redαβ positive or not) and contacting the DNA molecules in the host cell. When the recombination occurs in vitro the selection of DNA molecules may be accomplished by transforming the recombination mixture in a suitable host cell and selecting for positive clones as described above. When the recombination occurs in vivo the selection methods as described above may directly be applied.

A further subject matter of the invention is the use of cells, preferably bacterial cells, most preferably, *E. coli* cells capable of expressing the recE and recT, or redα and redβ, genes as a host cell for a cloning method involving homologous recombination.

Still a further subject matter of the invention is a vector system capable of expressing recE and recT, or redα and redβ, genes in a host cell and its use for a cloning method involving homologous recombination. Preferably, the vector system is also capable of expressing an exonuclease inhibitor gene as defined above, e.g. the λ redγ gene. The vector system may comprise at least one vector. The recE and recT, or redα and redβ, genes are preferably located on a single vector and more preferably under control of a regulatable promoter which may be the same for both genes or a single promoter for each gene.

Especially preferred is a vector system which is capable of overexpressing the recT, or redβ, gene versus the recE, or redβ, gene.

Still a further subject matter of the invention is the use of a source of RecE and RecT, or Redα and Redβ, proteins for a cloning method involving homologous recombination.

A still further subject matter of the invention is a reagent kit for cloning comprising (a) a host cell, preferably a bacterial host cell, (b) means of expressing recE and recT, or redα and redβ, genes in said host cell, e.g. comprising a vector system, and (c) a recipient cloning vehicle, e.g. a vector, capable of being replicated in said cell.

On the one hand, the recipient cloning vehicle which corresponds to the first DNA molecule of the process of the invention can already be present in the bacterial cell. On the other hand, it can be present separated from the bacterial cell.

In a further embodiment the reagent kit comprises (a) a source for RecE and RecT, or Redα and Redβ, proteins and (b) a recipient cloning vehicle capable of being propagated in a host cell and (c) optionally a host cell suitable for propagating said recipient cloning vehicle.

The reagent kit furthermore contains, preferably, means for expressing a site specific recombinase in said host cell, in particular, when the recipient ET cloning product contains at least one site specific recombinase target site. Moreover, the reagent kit can also contain DNA molecules suitable for use as a source of linear DNA fragments used for ET cloning, preferably by serving as templates for PCR generation of the linear fragment, also as specifically designed DNA vectors from which the linear DNA fragment is released by restriction enzyme cleavage, or as prepared linear fragments included in the kit for use as positive controls. or other tasks. Moreover, the reagent kit can also contain nucleic acid amplification primers comprising a region of homology to said vector. Preferably, this region of homology is located at the 5'-end of the nucleic acid amplification primer.

The invention is further illustrated by the following Sequence listings, Figures and Examples.

SEQ ID NO. 1: shows the nucleic acid sequence of the plasmid pBAD24-rec ET (FIG. 7).

SEQ ID NOs 2/3: show the nucleic acid and amino acid sequences of the truncated recE gene (t-recE) present on pBAD24-recET at positions 1320-2162.

SEQ ID NOs 4/5: show the nucleic acid and amino acid sequences of the recT gene present on pBAD24-recET at position 2155-2972.

SEQ ID NOs 6/7: show the nucleic acid and amino acid sequences of the araC gene present on the complementary stand to the one shown of pBAD24-recET at positions 974-996.

SEQ ID NOs 8/9: show the nucleic acid an amino acid sequences of the bla gene present on pBAD24-recET at positions 3493-4353.

SEQ ID NO 10: shows the nucleic acid sequence of the plasmid pBAD-ETγ (FIG. 13).

SEQ ID No 11: shows the nucleic acid sequence of the plasmid pBAD-αβγ (FIG. 14) as well as the coding regions for the genes redα (1320-200), redβ (2086-2871) and redγ (3403-3819).

Figure 14:
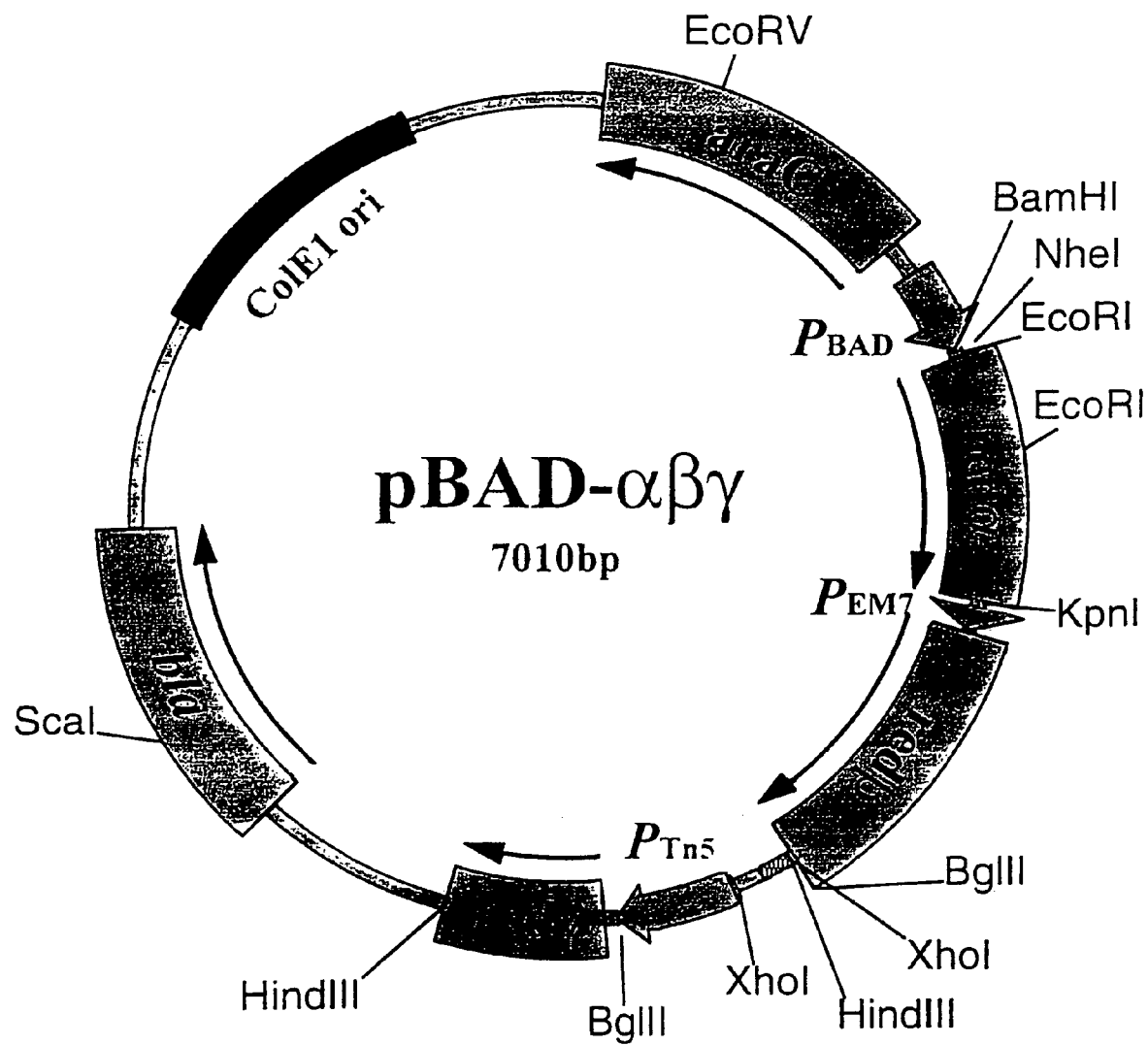

SEQ ID NOs 12-14: show the amino acid sequences of the Redα, Redβ and Redγ proteins, respectively. The redy sequence is present on each of pBAD-ETγ (FIG. 13) and pBAD-αβγ (FIG. 14).

FIG. 1

A preferred method for ET cloning is shown by diagram. The linear DNA fragment to be cloned is synthesized by PCR using oligonucleotide primers that contain a left homology arm chosen to match sequences in the recipient episome and a sequence. for priming in the PCR reaction, and a right homology arm chosen to match another sequence in the recipient episome and a sequence for priming in the PCR reaction. The product of the PCR reaction, here a selectable marker gene (sm1), is consequently flanked by the left and right homology arms and can be mixed together in vitro with the episome before co-transformation, or transformed into a host cell harboring the target episome. The host cell contains the products of the recE and recT genes. ET cloning products are identified by the combination of two selectable markers, sm1 and sm2 on the recipient episome.

FIG. 2

Three ways to identify ET cloning products are depicted. The first, (on the left of the figure), shows the acquisition, by ET cloning, of a gene that conveys a phenotypic difference to the host, here a selectable marker gene (sm). The second (in the centre of the figure) shows the loss, by ET cloning, of a gene that conveys a phenotypic difference to the host, here a counter selectable marker gene (counter-sm). The third shows the loss of a target site (RT, shown as triangles on the circular episome) for a site specific recombinase (SSR), by ET cloning. In this case, the correct ET cloning product deletes one of the target sites required by the SSR to delete a selectable marker gene (sm). The failure of the SSR to delete the sm gene identifies the correct ET cloning product.

FIG. 3

A simple example of ET cloning is presented. (a) Top panel-PCR products (left lane) synthesized from oligonucleotides designed as described in FIG. 1 to amplify by PCR a kanamycin resistance gene and to be flanked by homology arms present in the recipient vector, were mixed in vitro with the recipient vector (2nd lane) and cotransformed into a recET+$E. coli$ host. The recipient vector carried an ampillicin resistance gene. (b) Transformation of the sbcA $E. coli$ strain JC9604 with either the PCR product alone (0.2 µg) or the vector alone (0.3 µg) did not convey resistance to double selection with ampicillin and kanamycin (amp+kan), however cotransformation of both the PCR product and the vector produced double resistant colonies. More than 95% of these colonies contained the correct ET cloning product where the kanamycin gene had precisely integrated into the recipient vector according to the choice of homology arms. The two lanes on the right of (a) show Pvu II restriction enzyme digestion of the recipient vector before and after ET cloning. (c) As for b, except that six PCR products (0.2 µg each) were cotransformed with pSVpaZ11 (0.3 µg each) into JC9604 and plated onto Amp+Kan plates or Amp plates. Results are plotted as Amp+Kan-resistant colonies, representing recombination products, divided by Amp-resistant colonies, representing the plasmid transformation efficiency of the competent cell preparation, $\times 10^6$. The PCR products were equivalent to the a-b PCR product except that homology arm lengths were varied. Results are from five experiments that used the same batches of competent cells and DNAs. Error bars represent standard deviation. (d) Eight products flanked by 50 bp homology arms were cotransformed with pSVpaZ 11 into JC9604. All eight PCR products contained the same left homology arm and amplified neo gene. The right homology arms were chosen from the pSVpaZ11 sequence to be adjacent to (0), or at increasing distances (7-3100 bp), from the left. Results are from four experiments.

Figure 4A:
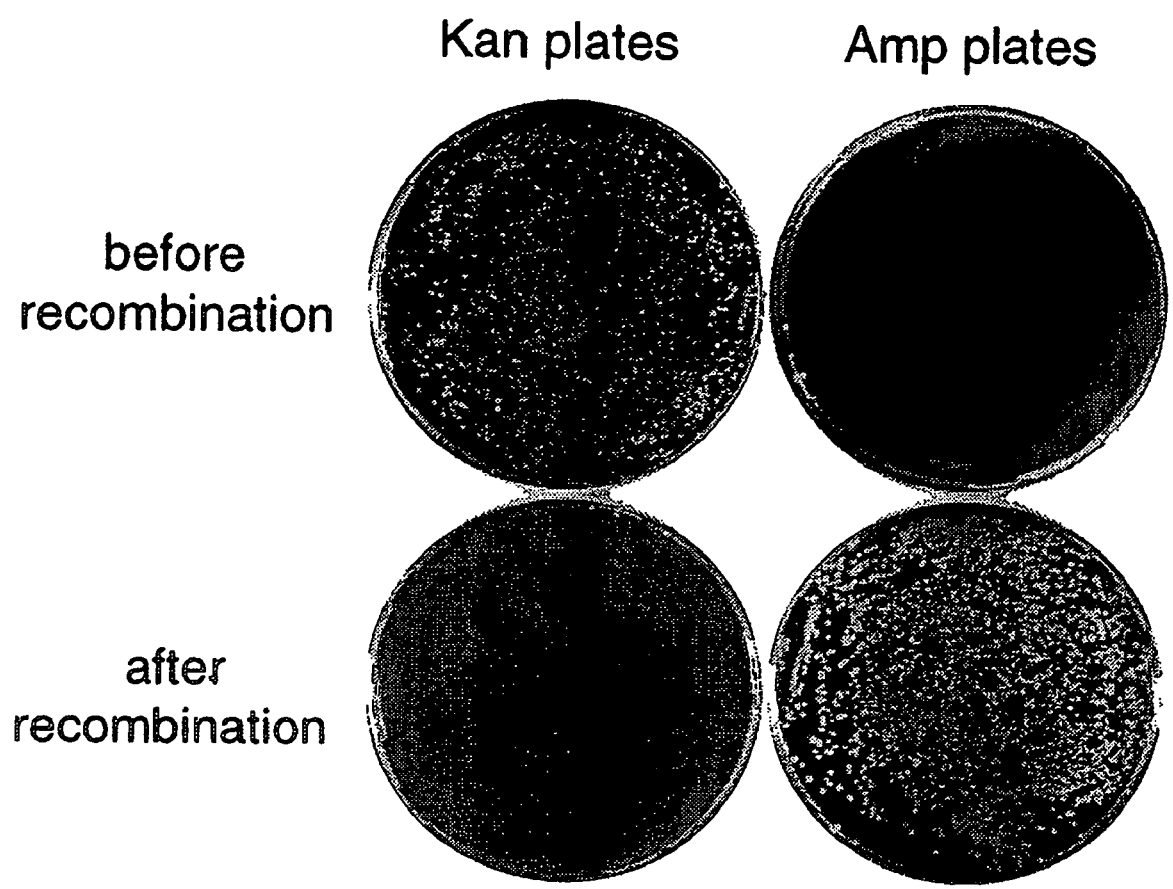

FIGS. 4(a) and (b)

ET cloning in an approximately 100 kb P1 vector to exchange the selectable marker.

A P1 clone which uses a kanamycin resistance gene as selectable marker and which contains at least 70 kb of the mouse Hox a gene cluster was used. Before ET cloning, this episome conveys kanamycin resistance (top panel, upper left) to its host $E. coli$ which are ampillicin sensitive (top panel, upper right). A linear DNA fragment designed to replace the kanamycin resistance gene with an ampillicin resistance gene was made by PCR as outlined in FIG. 1 and transformed into $E. coli$ host cells in which the recipient Hox a/P1 vector was resident. ET cloning resulted in the deletion of the kanamycin resistance gene, and restoration of kanamycin sensitivity (top panel, lower left) and the acquisition of ampillicin resistance (top panel, lower right). Precise DNA recombination was verified by restriction digestion and Southern blotting analyses of isolated DNA before and after ET cloning (lower panel).

Figure 5:
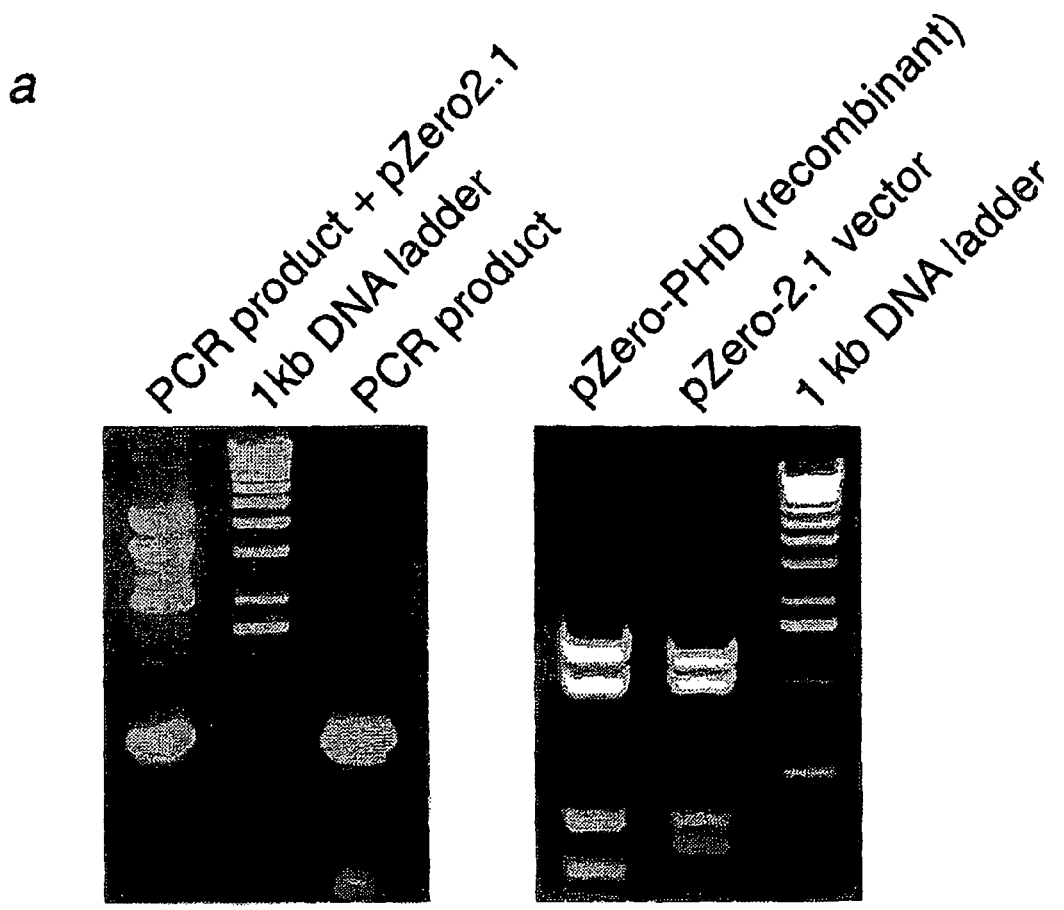
Figure 5:
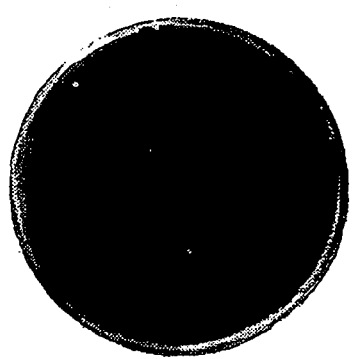
Figure 5:
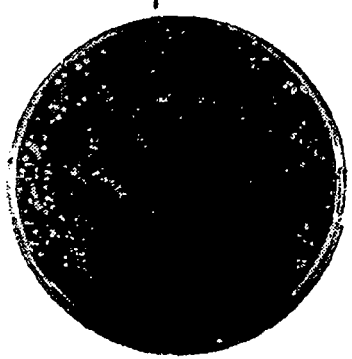

FIGS. 5(a) and (b)

ET cloning to remove a counter selectable marker A PCR fragment (upper panel, left, third lane) made as outlined in FIGS. 1 and 2 to contain the kanamycin resistance gene was directed by its chosen homology arms to delete the counter selectable ccdB gene present in the vector, pZero-2.1. The PCR product and the pZero vector were mixed in vitro (upper panel, left, 1 st lane) before cotransformation into a recE/recT+$E. coli$ host. Transformation of pZero-2.1 alone and plating onto kanamycin selection medium resulted in little colony growth (lower panel, left). Cotransformation of pZero-2.1 and the PCR product presented ET cloning products (lower panel, right) which showed the intended molecular event as visualized by Pvu II digestion (upper panel, right).

FIG. 6

ET cloning mediated by inducible expression of recE and recT from an episome.

RecE/RecT mediate homologous recombination between linear and circular DNA molecules. (a) The plasmid pBAD24-recET was transformed into $E. coli$ JC5547, and then batches of competent cells were prepared after induction of RecE/RecT expression by addition of L-arabinose for the times indicated before harvesting. A PCR product, made using oligonucleotides e and f to contain the chloramphenicol resistance gene (cm) of pMAK705 and 50 bp homology arms chosen to flank the ampicililin resistance gene (bla) of pBAD24-recET, was then transformed and recombinants identified on chloramphenicol plates. (b) Arabinose was added to cultures of pBAD24-recET transformed JC5547 for different times immediately before harvesting for competent cell preparation. Total protein expression was analyzed by SDS-PAGE and Coomassie blue staining. (c) The number of chloramphenicol resistant colonies per µg of PCR product was normalized against a control for transformation efficiency, determined by including 5 pg pZero2.1, conveying kanamycin resistance, in the transformation and plating an aliquot onto Kan plates.

FIG. 7A

The plasmid pBAD24-recET is shown by diagram. The plasmid contains the genes recE (in a truncated form) and recT under control of the inducible BAD promoter ($P_{BAD}$) The plasmid further contains an ampillicin resistance gene (Amp') and an araC gene.

FIG. 7B

The nucleic acid sequence and the protein coding portions of pBAD24-recET are depicted.

FIG. 8

Manipulation of a large E. coli episome by multiple recombination steps. FIG. 8a depicts the scheme of the recombination reactions. A P1 clone of the Mouse Hoxa complex, resident in JC9604, was modified by recombination with PCR products that contained the neo gene and two Flp recombination targets (FRTs). The two PCR products were identical except that one was flanked by g and h homology arms (insertion), and the other was flanked by i and h homology arms (deletion). In a second step, the neo gene was removed by Flp recombination between the FRTs by transient transformation of a Flp expression plasmid based on the pSC101 temperature-sensitive origin (ts ori). FIG. 8b (upper panel): ethidium bromide stained agarose gel showing EcoR1 digestions of P1 DNA preparations from three independent colonies for each step. FIG. 8b (middle panel): a Southern blot of the upper panel hybridized with a neo gene probe. FIG. 8b (lower panel): a Southern blot of the upper panel hybridized with a Hoxa3 probe to visualize the site of recombination. Lane 1 in each of the panels shows the original Hoxa3 P1 clone grown in E. coli strain NS3145. Lane 2 in each of the panels shows that replacement of the Tn903 kanamycin resistance gene in the P1 vector with an ampicillin resistance gene, increased the 8.1 kb band (lane 1) to 9.0 kb. Lane 3 in each of the panels shows that insertion of the Tn5-neo gene with g-h homology arms upstream of Hoxa3, increased the 6.7 kb band (lanes 1,2) to 9.0 kb. Lane 4 in each of the panels shows that Flp recombinase deleted the g-h neo gene reducing the 9.0 kb band (lane 3) back to 6.7 kb. Lane 5 in each of the panels shows that deletion of 6 kb of Hoxa3-4 intergenic DNA by replacement with the i-h neo gene, decreased the 6.7 kb band (lane 2) to 4.5 kb. Lane 6 in each of the panels shows that Flp recombinase deleted the i-h neo gene reducing the 4.5 kb band to 2.3 kb.

FIG. 9

Figure 9A:
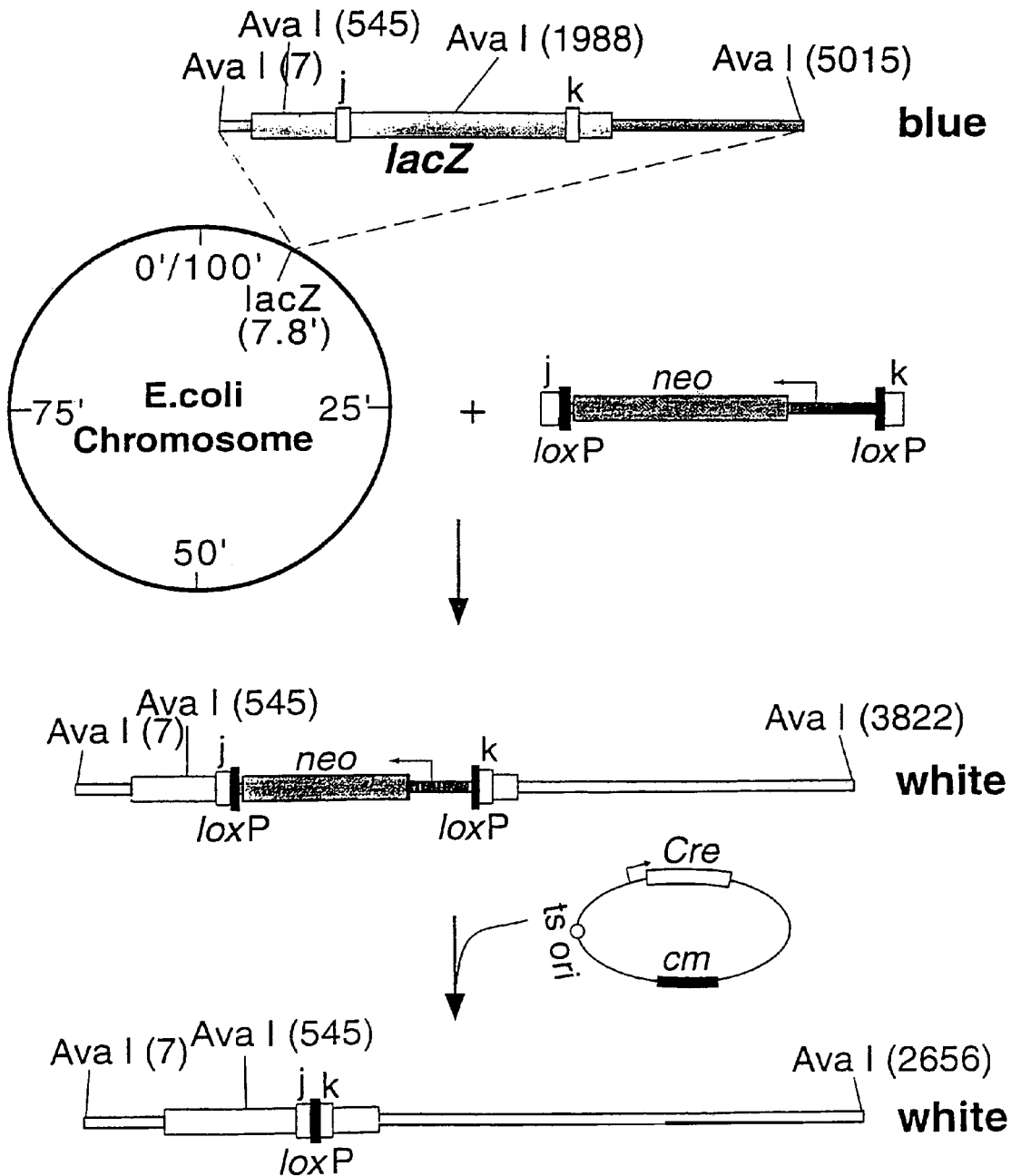

Manipulation of the E. coli chromosome. FIG. 9a depicts the scheme of the recombination reactions. The endogenous lacZ gene of JC9604 at 7.8' of the E. coli chromosome, shown in expanded form with relevant Ava I sites and coordinates, was targeted by a PCR fragment that contained the neo gene flanked by homology arms j and k, and loxP sites, as depicted. Integration of the neo gene removed most of the lacZ gene including an Ava I site to alter the 1443 and 3027 bp bands into a 3277 bp band. In a second step, the neo gene was removed by Cre recombination between the loxPs by transient transformation of a Cre expression plasmid based on the pSC101 temperature-sensitive origin (ts ori). Removal of the neo gene by Cre recombinase reduces the 3277 band to 2111 bp. FIG. 9b shows β-galactosidase expression evaluated by streaking colonies on X-Gal plates. The top row of three streaks show β-galactosidase expression in the host JC9604 strain (w.t.), the lower three rows (Km) show 24 independent primary colonies, 20 of which display a loss of β-galactosidase expression indicative of the intended recombination event. FIG. 9c shows the results from Southern analysis of E. coli chromosomal DNA digested with Ava I using a random primed probe made from the entire lacZ coding region; lanes 1,2, w.t.; lanes 3-6, four independent white colonies after integration of the j-k neo gene; lanes 7-10; the same four colonies after transient transformation with the Cre expression plasmid.

FIG. 10

Figure 9:
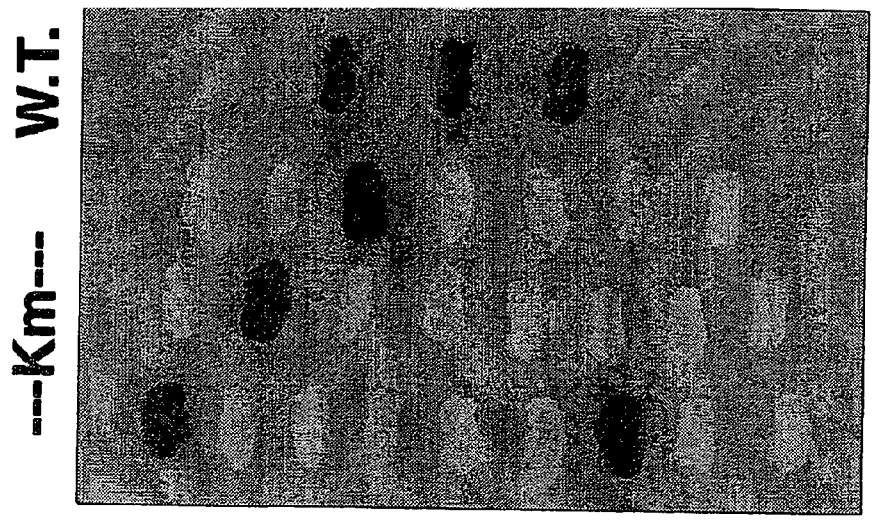
Figure 9:
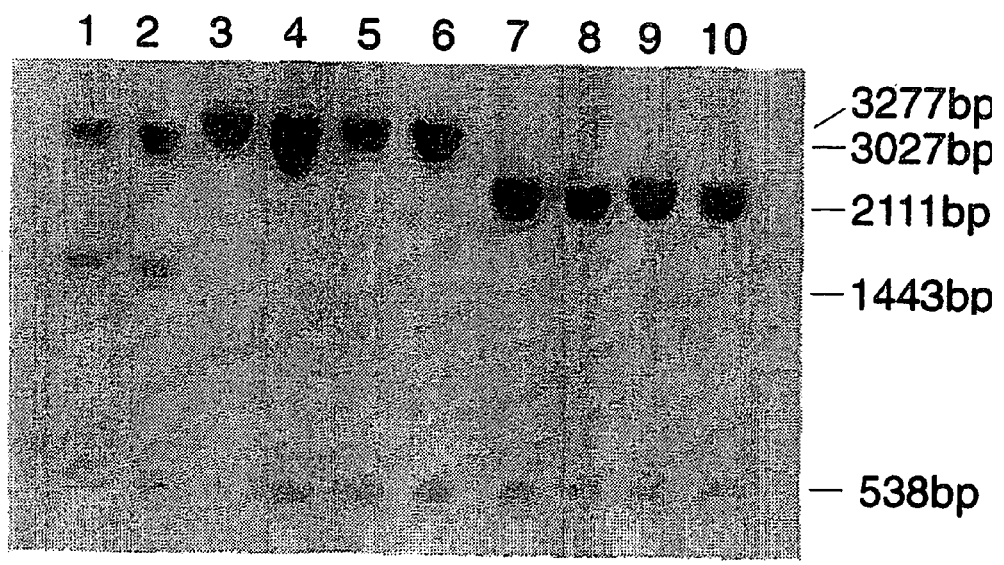
Figure 10A:
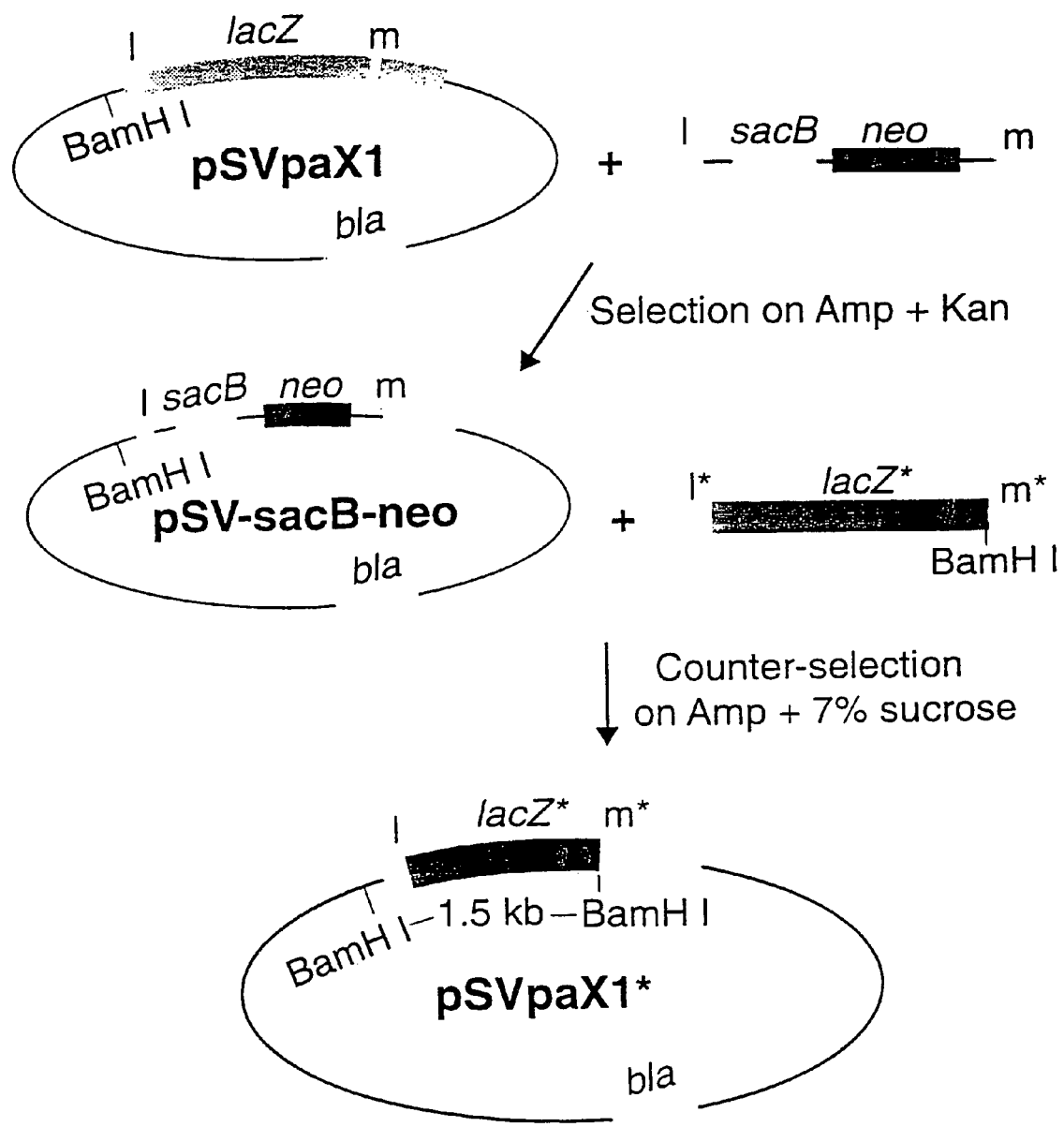
Figure 10:
Figure 10:
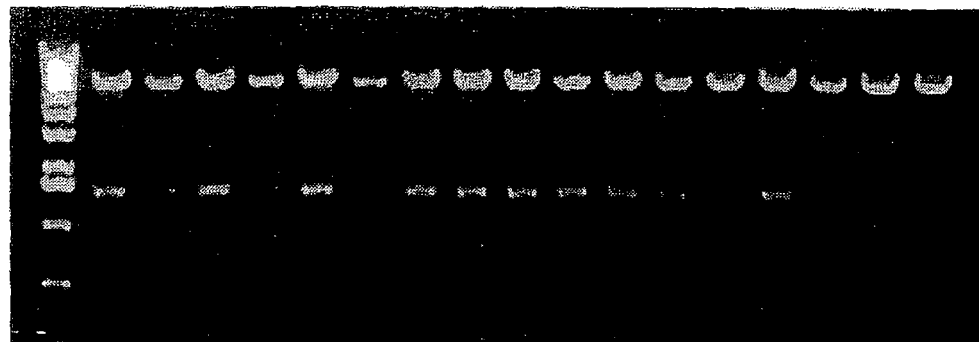
Figure 10:

Two rounds of ET cloning to introduce a point mutation. FIG. 10a depicts the scheme of the recombination reactions. The lacZ gene of pSVpaX1 was disrupted in JC9604lacZ, a strain made by the experiment of FIG. 9 to ablate endogenous lacZ expression and remove competitive sequences, by a sacB-neo gene cassette, synthesized by PCR to pIB279 and flanked by l and m homology arms. The recombinants, termed pSV-sacB-neo, were selected on Amp+Kan plates. The lacZ gene of pSV-sacB-neo was then repaired by a PCR fragment made from the intact lacZ gene using l* and m* homology arms. The m* homology arm included a silent C to G change that created a BamH1 site. The recombinants, termed pSV-paX1*, were identified by counter selection against the sacB gene using 7% sucrose. FIG. 10b shows that β-galactosidase expression from pSVpaX1 was disrupted in pSV-sacB-neo and restored in pSVpaX1*. Expression was analyzed on X-gal plates. Three independent colonies of each pSV-sacB-neo and pSVpaX1* are shown. FIG. 10c shows Ethidium bromide stained agarose gels of BamH1 digested DNA prepared from independent colonies taken after counter selection with sucrose. All β-galactosidase expressing colonies (blue) contained the introduced BamH1 restriction site (upper panel). All white colonies displayed large rearrangements and no product carried the diagnostic 1.5 kb BamH1 restriction fragment (lower panel).

FIG. 11

Figure 11A:
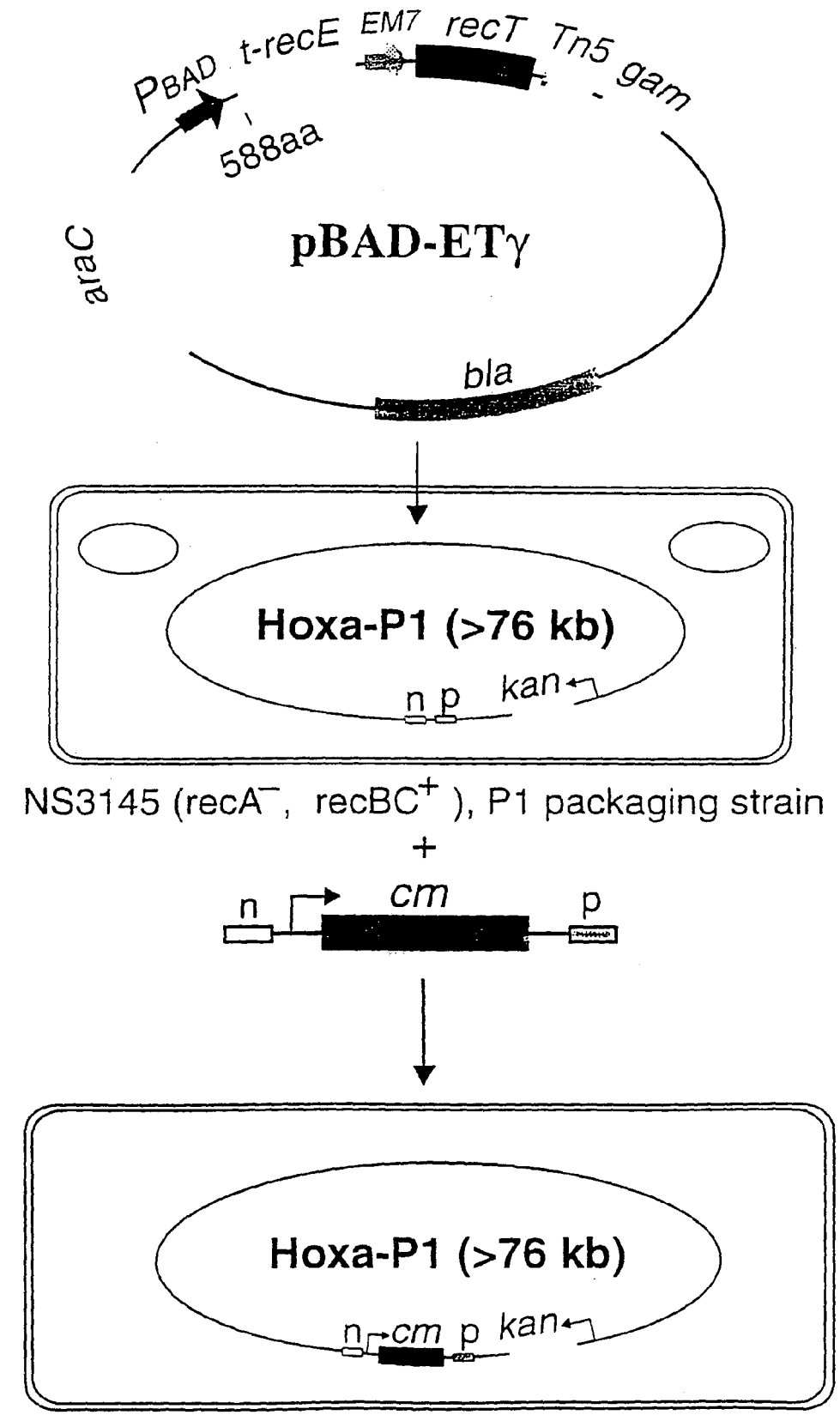

Transferance of ET cloning into a recBC+ host to modify a large episome. FIG. 11a depicts the plasmid, pBAD-ETγ, which carries the mobile ET system, and the strategy employed to target the Hoxa P1 episome. pBAD-ETγ is based on pBAD24 and includes (i) the truncated recE gene (t-recE) under the arabinose-inducible $P_{BAD}$ promoter; (ii) the recT gene under the EM7 promoter; and (iii) the redγ gene under the Tn5 promoter. It was transformed into NS3145, a recA E. coli strain which contained the Hoxa P1 episome. After arabinose induction, competent cells were prepared and transformed with a PCR product carrying the chloramphenicol resistance gene (cm) flanked by n and p homology arms. n and p were chosen to recombine with a segment of the P1 vector. FIG. 11b shows the results from Southern blots of Pvu II digested DNAs hybridized with a probe made from the P1 vector to visualize the recombination target site (upper panel) and a probe made from the chloramphenicol resistance gene (lower panel). Lane 1, DNA prepared from cells harboring the Hoxa P1 episome before ET cloning. Lanes 2-17, DNA prepared from 16 independent chloramphenicol resistant colonies.

FIG. 12

Comparison of ET cloning using the recE/recT genes in pBAD-ETγ with redα/redβ genes in pBAD-αβγ.

Figure 6:
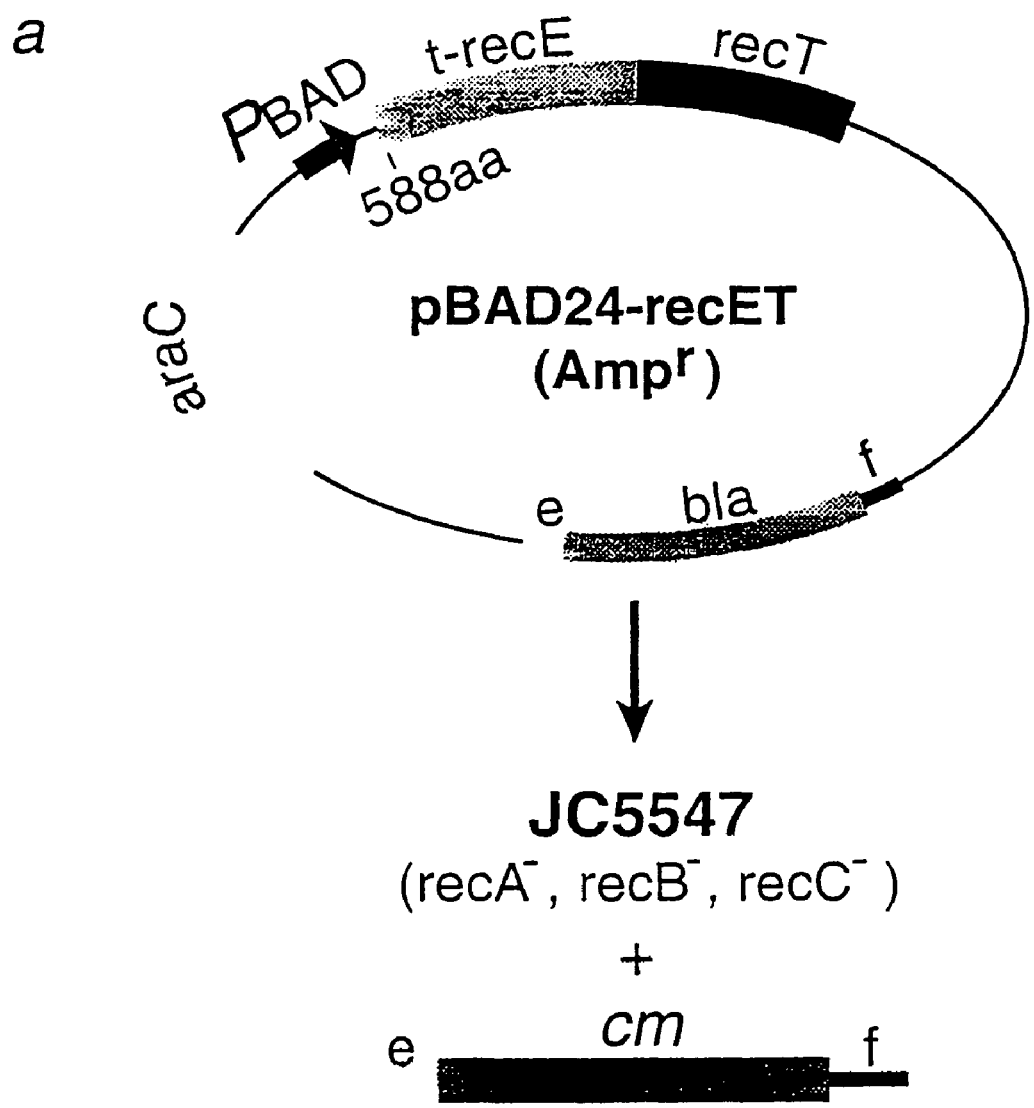
Figure 6:
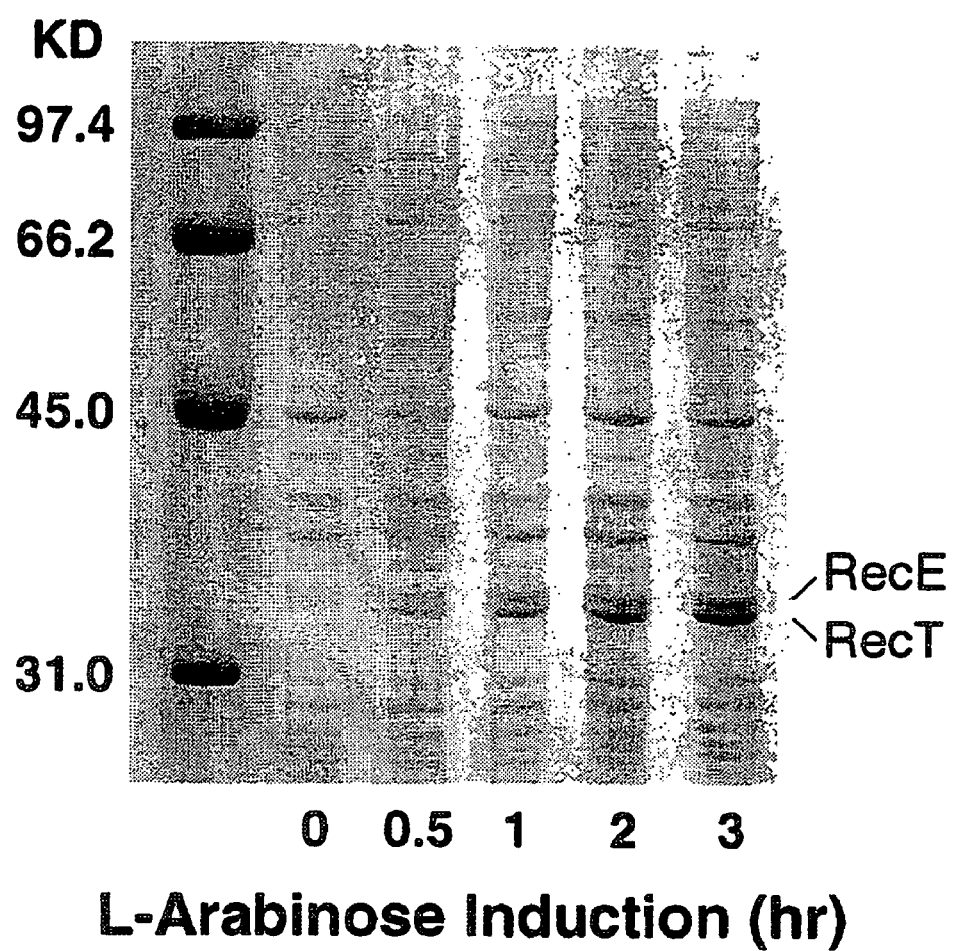
Figure 6:
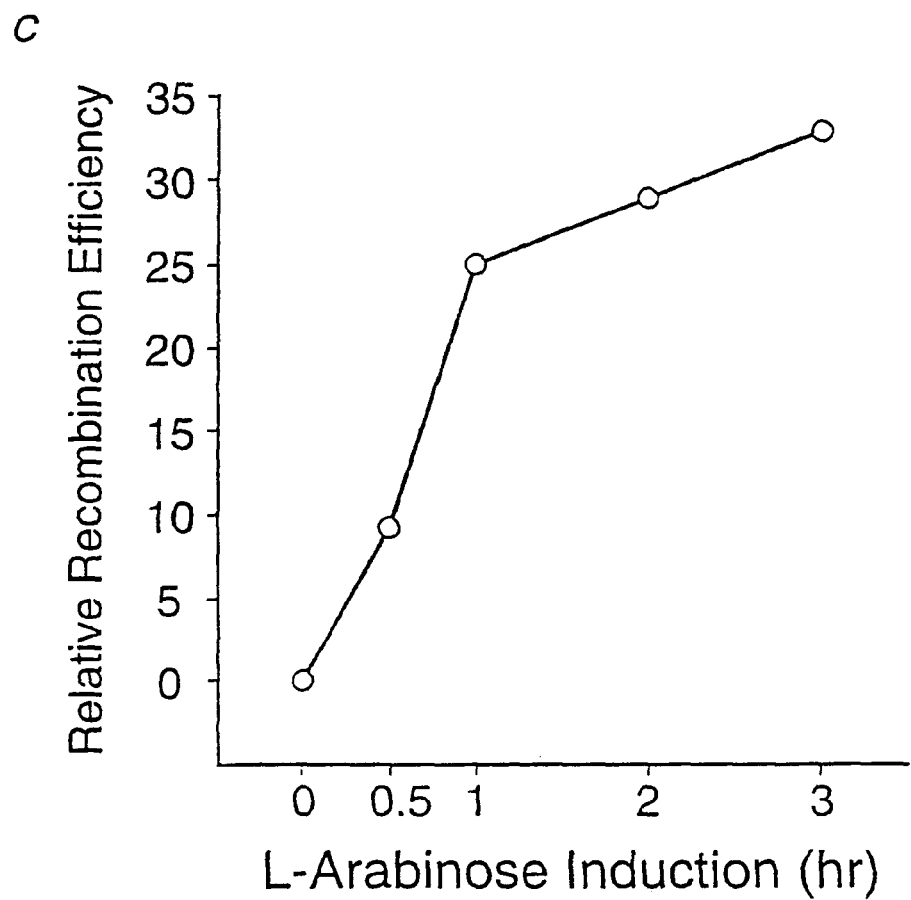

The plasmids pBAD-ETγ or pBAD-αβγ, depicted, were transformed into the E. coli recA−, recBC+ strain, DK1 and targeted by a chloramphenicol gene as described in FIG. 6 to evaluate ET cloning efficiencies. Arabinose induction of protein expression was for 1 hour.

FIG. 13A

The plasmid pBAD-ETγ is shown by diagram.

FIG. 13B

The nucleic acid sequence and the protein coding portions of pBAD-ETγ are depicted.

FIG. 14A

The plasmid pBAD-αβγ is shown by diagram. This plasmid substantially corresponds to the plasmid shown in FIG.

13 except that the recE and recT genes are substituted by the redα and redβ genes.

FIG. 14B

The nucleic acid sequence and the protein coding portions of pBAD-αβγ are depicted.

1. Methods 1.1 Preparation of Linear Fragments

Standard PCR reaction condition were used to amplify linear DNA fragments.

Table 1

The Tn5-neo gene from pJP5603 (Penfold and Pemberton, Gene 118 (1992), 145-146) was amplified by using oligo pairs a/b and c/d. The chloramphenicol (cm) resistant gene from pMAK705 (Hashimoto-Gotoh and Sekiguchi, J. Bacteriol. 131 (1977), 405-412) was amplified by using primer pairs e/f and n/p. The Tn5-neo gene flanked by FRT or loxP sites was amplified from pKaZ or pKaX (http://www.embl-heidelberg.de/ExternalInfo/stewart) using oligo pairs i/h, g/h and j/k. The sacB-neo cassette from plB279 (Blomfield et al., Mol. Microbiol. 5 (1991), 1447-1457) was amplified by using oligo pair l/m. The lacZ gene fragment from pSVpaZ11 (Buchholz et al., Nucleic Acids Res. 24 (1996), 4256-4262) was amplified using oligo pair 1*/m*. PCR products were purified using the QIAGEN PCR Purification Kit and eluted with $H_2O_2$, followed by digestion of any residual template DNA with Dpn I. After digestion, PCR products were extracted once with Phenol:$CHCl_3$, ethanol precipitated and resuspended in $H_2O$ at approximately 0.5 μg/μl.

1.2 Preparation of Competent Cells and Electroporation

Saturated overnight cultures were diluted 50 fold into LB medium, grown to an OD600 of 0.5, following by chilling on ice for 15 min. Bacterial cells were centrifuged at 7,000 rpm for 10 min at 0° C. The pellet was resuspended in ice-cold 10% glycerol and centrifuged again (7,000 rpm, −5° C., 10 min). This was repeated twice more and the cell pellet was suspended in an equal volume of ice-cold 10% glycerol. Aliquots of 50 μl were frozen in liquid nitrogen and stored at −80° C. Cells were thawed on ice and 1 μl DNA solution (containing, for co-transformation, 0.3 μg plasmid and 0.2 μg PCR products; or, for transformation, 0.2 μg PCR products) was added. Electroporation was performed using ice-cold cuvettes and a Bio-Rad Gene Pulser set to 25 μFD, 2.3 kV with Pulse Controller set at 200 ohms. LB medium (1 ml) was added after electroporation. The cells were incubated at 37° C. for 1 hour with shaking and then spread on antibiotic plates.

1.3 Induction of RecE and RecT Expression E. coli JC5547 carrying pBAD24-recET was cultured overnight in LB medium plus 0.2% glucose, 100 μg/ml ampicillin. Five parallel LB cultures, one of which (0) included 0.2% glucose, were started by a 1/100 inoculation. The cultures were incubated at 37° C. with shaking for 4 hours and 0.1% L-arabinose was added 3, 2, 1 or 1/2 hour before harvesting and processing as above. Immediately before harvesting, 100 μl was removed for analysis on a 10% SDS-polyacrylamide gel. E. coli NS3145 carrying Hoxa-P1 and pBAD-ETγ was induced by 0.1% L-arabinose for 90 min before harvesting.

1.4 Transient Transformation of FLP and Cre Expression Plasmids

The FLP and Cre expression plasmids, 705-Cre and 705-FLP (Buchholz et al, Nucleic Acids Res. 24 (1996), 3118-3119), based on the pSC101 temperature sensitive origin, were transformed into rubidium chloride competent bacterial cells. Cells were spread on 25 μg/ml chloramphenicol plates, and grown for 2 days at 30° C., whereupon colonies were picked, replated on L-agar plates without any antibiotics and incubated at 40° C. overnight. Single colonies were analyzed on various antibiotic plates and all showed the expected loss of chloramphenicol and kanamycin resistance.

1.5 Sucrose Counter Selection of SacB Expression

Figure 11:
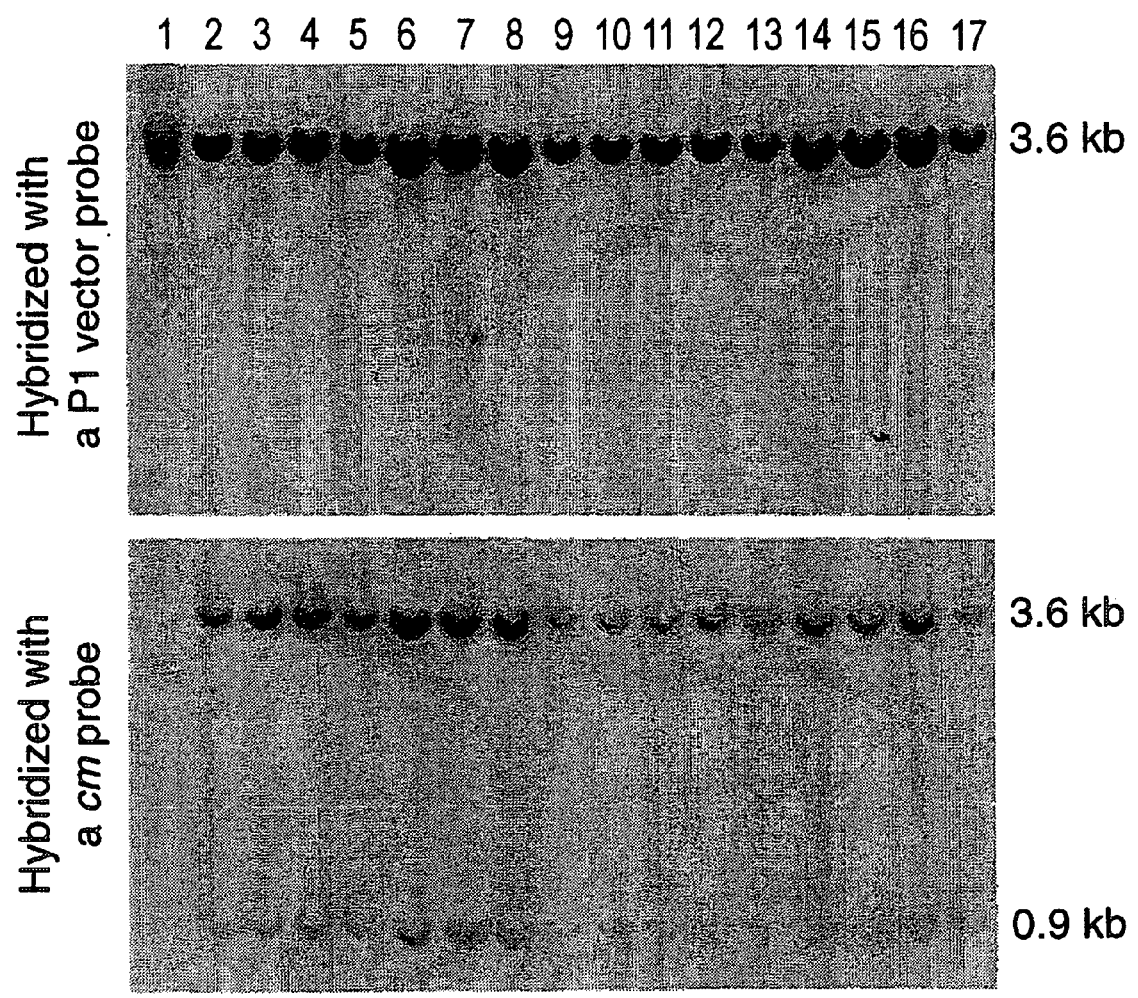

The E. coli JC9604lacZ strain, generated as described in FIG. 11, was cotransformed with a sacB-neo PCR fragment and pSVpaX1 (Buchholz et al, Nucleic Acids Res. 24 (1996), 4256-4262). After selection on 100 μg/ml ampicillin, 50 μg/ml kanamycin plates, pSVpaX-sacB-neo plasmids were isolated and cotransformed into fresh JC9604lacZ cells with a PCR fragment amplified from pSVpaX1 using primers 1*/m*. Oligo m* carried a silent point mutation which generated a BamHl site. Cells were plated on 7% sucrose, 100 μg/ml ampicillin, 40 μg/ml X-gal plates and incubated at 28° C. for 2 days. The blue and white colonies grown on sucrose plates were counted and further checked by restriction analysis.

1.6 Other Methods

DNA preparation and Southern analysis were performed according to standard procedures. Hybridization probes were generated by random priming of fragments isolated from the Tn5 neo gene (PvuII), Hoxa3 gene (both HindIII fragments), lacZ genes (EcoR1 and BamH1 fragments from pSVpaX1), cm gene (BstB1 fragments from pMAK705) and P1 vector fragments (2.2 kb EcoR1 fragments from P1 vector).

2. Results 2.1 Identification of Recombination Events in E. coli

Figure 3:
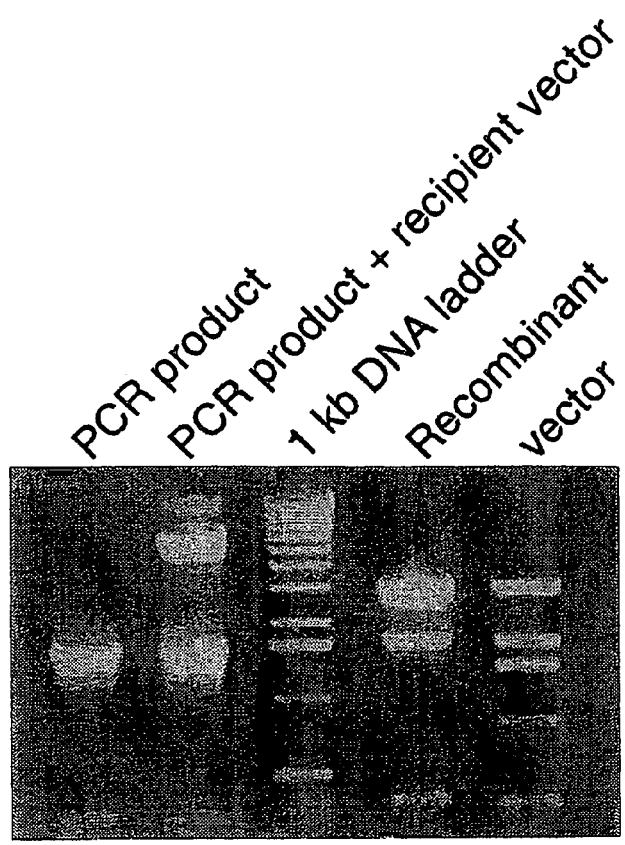
Figure 3:
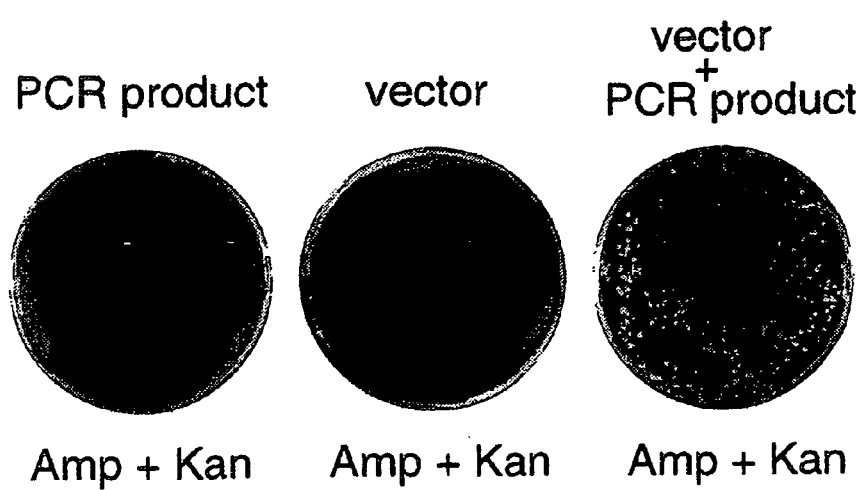
Figure 3:
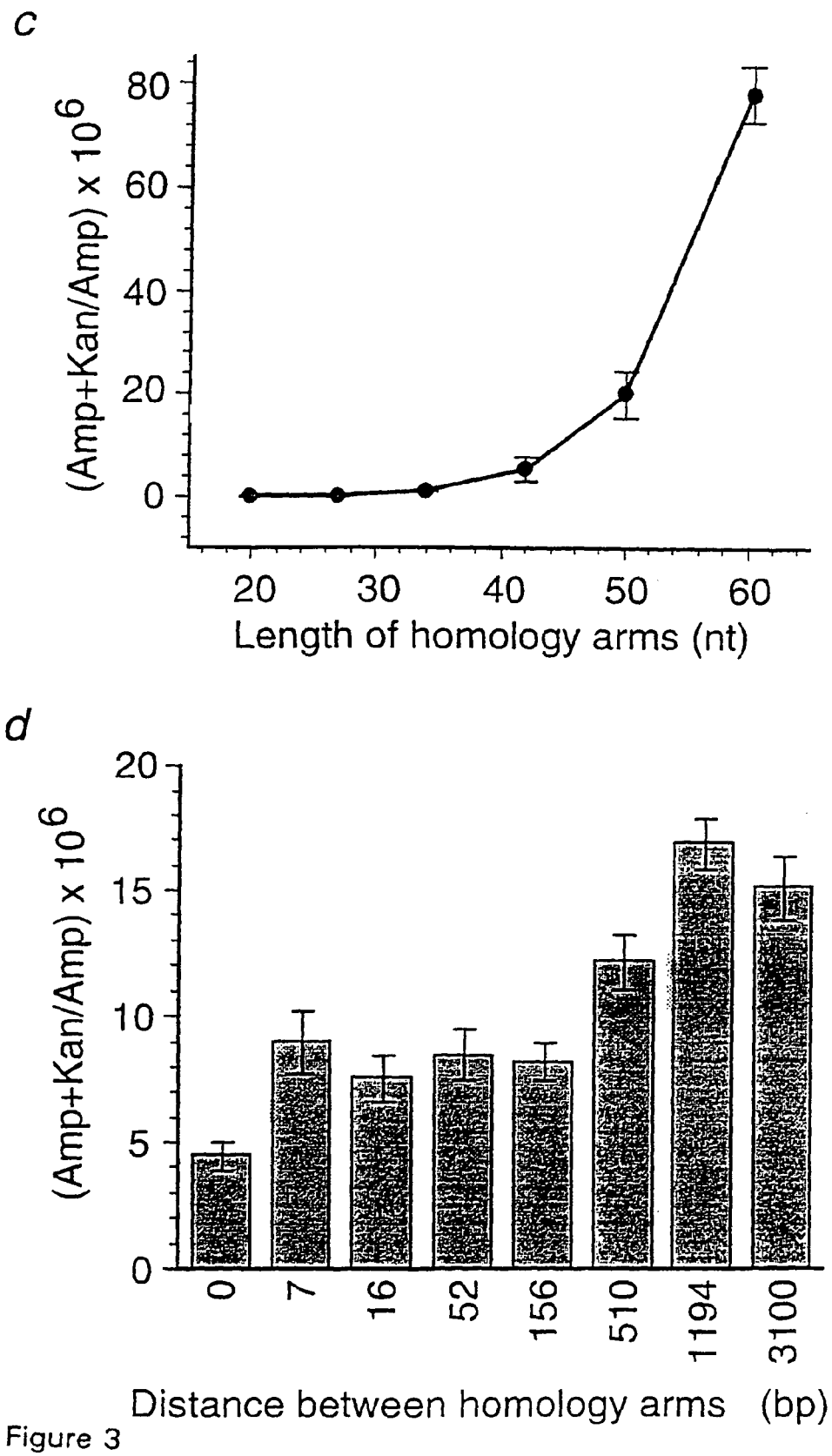

To identify a flexible homologous recombination reaction in E. coli, an assay based on recombination between linear and circular DNAs was designed (FIG. 1, FIG. 3). Linear DNA carrying the Tn5 kanamycin resistance gene (neo) was made by PCR (FIG. 3a). Initially, the oligonucleotides used for PCR amplification of neo were 60 mers consisting of 42 nucleotides at their 5' ends identical to chosen regions in the plasmid and, at the 3' ends, 18 nucleotides to serve as PCR primers. Linear and circular DNAs were mixed in equimolar proportions and co-transformed into a variety of E. coli hosts. Homologous recombination was only detected in sbcA E. coli hosts. More than 95% of double ampicillin/kanamycin resistant colonies (FIG. 3b) contained the expected homologously recombined plasmid as determined by restriction digestion and sequencing. Only a low background of kanamycin resistance, due to genomic integration of the neo gene, was apparent (not shown).

The linear plus circular recombination reaction was characterized in two ways. The relationship betweeen homology arm length and recombination efficiency was simple, with longer arms recombining more efficiently (FIG. 3c). Efficiency increased within the range tested, up to 60 bp. The effect of distance between the two chosen homology sites in the recipient plasmid was examined (FIG. 3d). A set of eight PCR fragments was generated by use of a constant left homology arm with differing right homology arms. The right homology arms were chosen from the plasmid sequence to be 0-3100 bp from the left. Correct products were readily obtained from all, with less than 4 fold difference between them, although the insertional product (0) was least efficient. Correct products also depended on the presence of both homology arms, since PCR fragments containing only one arm failed to work.

2.2 Involvement of RecE and RecT

The relationship between host genotype and this homologous recombination reaction was more systemically examined using a panel of E. coli strains deficient in various recombination components (Table 1)

Only the two sbcA strains, JC8679 and JC9604 presented the intended recombination products and RecA was not required. In sbcA strains, expression of RecE and RecT is activated. Dependence on recE can be inferred from comparison of JC8679 with JC8691. Notably no recombination products were observed in JC9387 suggesting that the sbcBC background is not capable of supporting homologous recombination based on 50 nucleotide homology arms.

To demonstrate that RecE and RecT are involved, part of the recET operon was cloned into an inducible expression vector to create pBAD24-recET (FIG. 6a). the recE gene was truncated at its N-terminal end, as the first 588 a.a.s of RecE are dispensable. The recBC strain, JC5547, was transformed with pBAD24-recET and a time course of RecE/RecT induction performed by adding arabinose to the culture media at various times before harvesting for competent cells. The batches of harvested competent cells were evaluated for protein expression by gel electrophoresis (FIG. 6b) and for recombination between a linear DNA fragment and the endogenous pBAD24-recET plasmid (FIG. 6c). Without induction of RecE/RecT, no recombinant products were found, whereas recombination increased in approximate concordance with increased RecE/RecT expression. This experiment also shows that co-transformation of linear and circular DNAs is not essential and the circular recipient can be endogenous in the host. From the results shown in FIGS. 3, 6 and Table 2, we conclude that RecE and RecT mediate a very useful homologous recombination reaction in recBC E. coli at workable frequencies. Since RecE and RecT are involved, we refer to this way of recombining linear and circular DNA fragments as "ET cloning".

2.3 Application of ET Cloning to Large Target DNAs

Figure 4B:
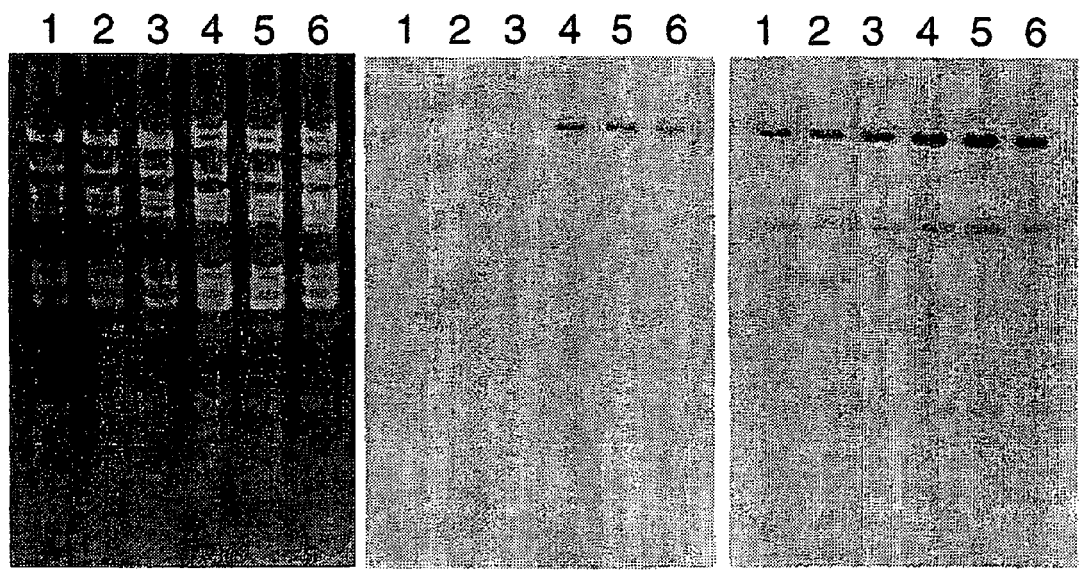

To show that large DNA episomes could be manipulated in E. coli, a >76 kb P1 clone that contains at least 59 kb of the intact mouse Hoxa complex, (confirmed by DNA sequencing and Southern blotting), was transferred to an E. coli strain having an sbcA background (JC9604) and subjected to two rounds of ET cloning. In the first round, the Tn903 kanamycin resistance gene resident in the P1 vector was replaced by an ampicillin resistance gene (FIG. 4). In the second round, the interval between the Hoxa3 and a4 genes was targeted either by inserting the neo gene between two base pairs upstream of the Hoxa3 proximal promoter, or by deleting 6203 bp between the Hoxa3 and a4 genes (FIG. 8a). Both insertional and deletional ET cloning products were readily obtained (FIG. 8b, lanes 2, 3 and 5) showing that the two rounds of ET cloning took place in this large E. coli episome with precision and no apparent unintended recombination.

The general applicability of ET cloning was further examined by targeting a gene in the E. coli chromosome (FIG. 9a). The β-galactosidase (lacZ) gene of JC9604 was chosen so that the ratio between correct and incorrect recombinants could be determined by evaluating β-galactosidase expression. Standard conditions (0.2 μg PCR fragment; 50 μl competent cells), produced 24 primary colonies, 20 of which were correct as determined by β-galactosidase expression (FIG. 9b), and DNA analysis (FIG. 9c, lanes 3-6).

2.4 Secondary Recombination Reactions to Remove Operational Sequences

The products of ET cloning as described above are limited by the necessary inclusion of selectable marker genes. Two different ways to use a further recombination step to remove this limitation were developed. In the first way, site specific recombination mediated by either Flp or Cre recombinase was employed. In the experiments of FIGS. 8 and 9, either Flp recombination target sites (FRTs) or Cre recombination target sites (loxPs) were included to flank the neo gene in the linear substrates. Recombination between the FRTs or loxPs was accomplished by Flp or Cre, respectively, expressed from plasmids with the pSC101 temperature sensitive replication origin (Hashimoto-Gotoh and Sekiguchi, J. Bacteriol. 131 (1977), 405-412) to permit simple elimination of these plasmids after site specific recombination by temperature shift. The precisely recombined Hoxa P1 vector was recovered after both ET and Flp recombination with no other recombination products apparent (FIG. 8, lanes 4 and 6). Similarly, Cre recombinase precisely recombined the targeted lacZ allele (FIG. 9, lanes 7-10). Thus site specific recombination can be readily coupled with ET cloning to remove operational sequences and leave a 34 bp site specific recombination target site at the point of DNA manipulation.

In the second way to remove the selectable marker gene, two rounds of ET cloning, combining positive and counter selection steps, were used to leave the DNA product free of any operational sequences (FIG. 10a).

Additionally this experiment was designed to evaluate, by a functional test based on β-galactosidase activity, whether ET cloning promoted small mutations such as frame shift or point mutations within the region being manipulated. In the first round, the lacZ gene of pSVpaX1 was disrupted with a 3.3 kb PCR fragment carrying the neo and B. subtilis sacB (Blomfield et al., Mol. Microbiol. 5 (1991), 1447-1457) genes, by selection for kanamycin resistance (FIG. 10a). As shown above for other positively selected recombination products, virtually all selected colonies were white (FIG. 10b), indicative of successful lacZ disruption, and 17 of 17 were confirmed as correct recombinants by DNA analysis. In the second round, a 1.5 kb PCR fragment designed to repair lacZ was introduced by counter selection against the sacB gene. Repair of lacZ included a silent point mutation to create a BamHl restriction site. Approximately one quarter of sucrose resistant colonies expressed β-galactosidase, and all analyzed (17 of 17; FIG. 10c) carried the repaired lacZ gene with the BamHl point mutation. The remaining three quarters of sucrose resistant colonies did not express β-galactosidase, and all analyzed (17 of 17; FIG. 10c) had undergone a variety of large mutational events, none of which resembled the ET cloning product. Thus, in two rounds of ET cloning directed at the lacZ gene, no disturbances of β-galactosidase activity by small mutations were observed, indicating the RecE/RecT recombination works with high fidelity. The significant presence of incorrect products observed in the counter selection step is an inherent limitation of the use of counter selection, since any mutation that ablates expression of the counter selection gene will be selected. Notably, all incorrect products were large mutations and therefore easily distinguished from the correct ET product by DNA analysis. In a different experiment (FIG. 5), we observed that ET cloning into pZero2.1 (InVitroGen) by counter selection against the ccdB gene gave a lower background of incorrect products (8%), indicating that the counter selection background is variable according to parameters that differ from those that influence ET cloning efficiencies.

2.5 Transference of ET Cloning between E. coli Hosts

The experiments shown above were performed in recBC- E. coli hosts since the sbcA mutation had been identified as a suppressor of recBC (Barbour et al., Proc. Natl. Acad. Sci.

USA 67 (1970), 128-135; Clark, Genetics 78 (1974), 259-271). However, many useful *E. coli* strains are recBC+, including strains commonly used for propagation of P1, BAC or PAC episomes. To transfer ET cloning into recBC+ strains, we developed pBAD-ETγ and pBAD-αβγ (FIGS. 13 and 14). These plasmids incorporate three features important to the mobility of ET cloning. First, RecBC is the major *E. coli* exonuclease and degrades introduced linear fragments. Therefore the RecBC inhibitor, Redγ (Murphy, J. Bacteriol. 173 (1991), 5808-5821), was included. Second, the recombinogenic potential of RecE/RecT, or Redα/Redβ, was regulated by placing recE or redα under an inducible promoter. Consequently ET cloning can be induced when required and undesired recombination events which are restricted at other times. Third, we observed that ET cloning efficiencies are enhanced when RecT, or Redβ, but not RecE, or Redα, is overexpressed. Therefore we placed recT, or redβ, under the strong, constitutive, EM7 promoter.

pBAD-ETγ was transformed into NS3145 *E. coli* harboring the original Hoxa P1 episome (FIG. 11*a*). A region in the P1 vector backbone was targeted by PCR amplification of the chloramphenicol resistance gene (cm) flanked by n and p homology arms. As described above for positively selected ET cloning reactions, most (>90%) chloramphenicol resistant colonies were correct. Notably, the overall efficiency of ET cloning, in terms of linear DNA transformed, was nearly three times better using pBAD-ETγ than with similar experiments based on targeting the same episome in the sbcA host, JC9604. This is consistent with our observation that overexpression of RecT improves ET cloning efficiencies.

Figure 12:
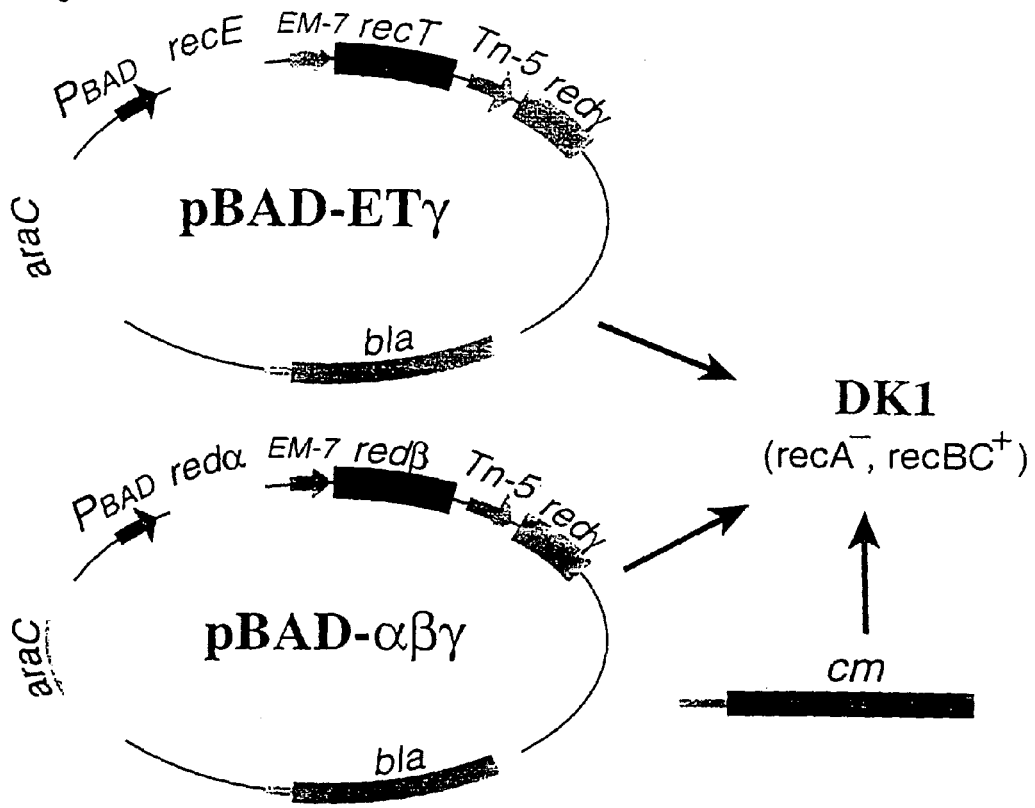
Figure 12:
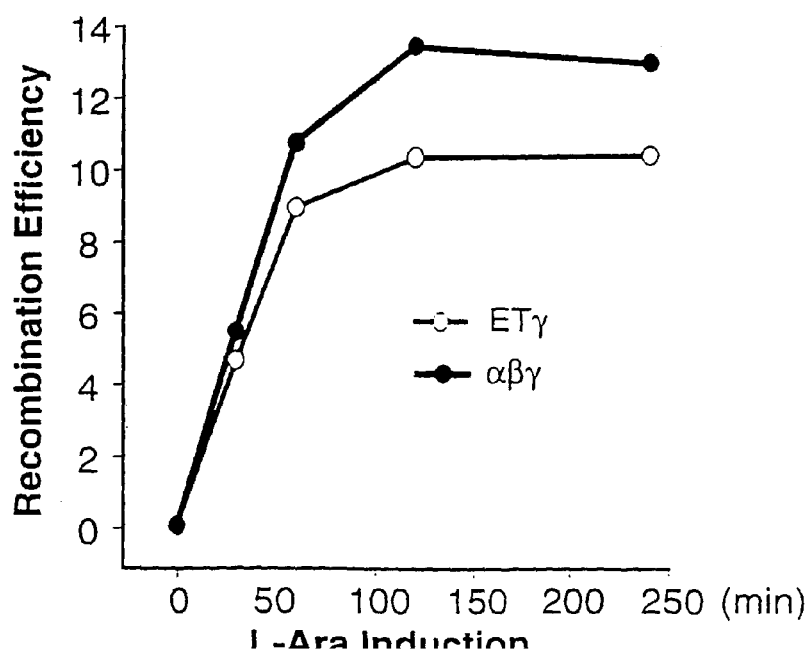

A comparison between ET cloning efficiencies mediated by RecE/RecT, expressed from pBAD-ETγ, and Redα/Redβ, expressed from pBAD-αβγ was made in the recA−, recBC+*E. coli* strain, DK1 (FIG. 12). After transformation of *E. coli* DK1 with either pBAD-ETγ or pBAD-αβγ, the same experiment as described in FIG. 6*a,c*, to replace the bla gene of the pBAD vector with a chloramphenicol gene was performed. Both pBAD-ETγ or pBAD-αβγ presented similar ET cloning efficiencies in terms of responsiveness to arabinose induction of RecE and Redα, and number of targeted events.

TABLE 1

| E. coli Strains | Genotypes | Amp + Kan | Amp × $10^8/\mu g$ |
|---|---|---|---|
| JC8679 | recBC sbcA | 318 | 2.30 |
| JC9604 | recA recBC sbcA | 114 | 0.30 |
| JC8691 | recBC sbcA recE | 0 | 0.37 |
| JC5547 | recA recBC | 0 | 0.37 |
| JC5519 | recBC | 0 | 1.80 |
| JC15329 | recA recBC sbcBC | 0 | 0.03 |
| JC9387 | recBC sbcBC | 0 | 2.20 |
| JC8111 | recBC sbcBC recF | 0 | 2.40 |
| JC9366 | recA | 0 | 0.37 |
| JC13031 | recJ | 0 | 0.45 |

The invention claimed is:

1. A method for cloning DNA molecules in procaryotic cells comprising the steps of:
   a) providing a procaryotic host cell capable of performing RecET homologous recombination, wherein the host cell expresses redα and redβ genes,
   b) contacting in said host cell a circular first DNA molecule which is capable of being replicated in said host cell with a linear second DNA molecule comprising at least two regions of sequence homology to regions on the first DNA molecule and further comprising a DNA fragment to be cloned under conditions which favour homologous recombination between said first and second DNA molecules and
   c) selecting a host cell in which homologous recombination between said first and second DNA molecules has occurred,
   wherein a second DNA molecule is introduced into the host cell in a form which allows recombination without further modification; and
   wherein when said RecET homologous recombination occurs, it is mediated by gene products of said redα and redβ genes.

2. The method according to claim 1 wherein the host cell is transformed with at least one vector capable of expressing redα and/or redβ genes.

3. The method of claim 1 wherein the expression of the redα and/or redβ genes is under control of a regulatable promoter.

4. The method of claim 2 wherein the redβ gene is overexpressed versus the redα gene.

5. The method according to claim 1 wherein the host cell is a gram-negative bacterial cell.

6. The method according to claim 5 wherein the host cell is an *Escherichia coli* cell.

7. The method according to claim 6 wherein the host cell is an *Escherichia coli* K12 strain.

8. The method according to claim 7 wherein the *E. coli* strain is selected from JC 8679 and JC 9604.

9. The method according to claim 1 wherein the host cell further expresses a redγ inhibitor gene.

10. The method according to claim 9 wherein the host cell is transformed with a vector expressing the redγ inhibitor gene.

11. The method according to claim 1 wherein the first DNA molecule is an extra chromosomal DNA molecule containing an origin of replication which is operative in the host cell.

12. The method according to claim 11 wherein the first DNA molecule is selected from plasmids, cosmids, P1 vectors, BAC vectors and PAC vectors.

13. The method according to claim 1 wherein the first DNA molecule is a host cell chromosome.

14. The method according to claim 1 wherein the regions of sequence homology are at least 15 nucleotides each.

15. The method according to claim 1 wherein the second DNA molecule is obtained by an amplification reaction.

16. The method according claim 1 wherein the first and/or second DNA molecules are introduced into the host cells by transformation.

17. The method according to claim 16 wherein the transformation method is electroporation.

18. The method according to claim 1 wherein the first and second DNA molecules are introduced into the host cell simultaneously by co-transformation.

19. The method according to claim 1 wherein the second DNA molecule is introduced into a host cell in which the first DNA molecule is already present.

20. The method according to claim 1 wherein the second DNA molecule contains at least one marker gene placed between the two regions of sequence homology and wherein homologous recombination is detected by expression of said marker gene.

21. The method according to claim 20 wherein the marker gene is selected from antibiotic resistance genes, deficiency complementation genes and reporter genes.

22. The method of claim 1 wherein the first DNA molecule contains at least one marker gene between the two regions of sequence homology and wherein homologous recombination is detected by lack of expression of said marker gene.

23. The method of any claim 1 wherein said marker gene is selected from genes which, under selected conditions, convey a toxic or bacteriostatic effect on the cell, and reporter genes.

24. A method according to claim 1 wherein the first DNA molecule contains at least one target site for a site specific recombinase between the two regions of sequence homology and wherein homologous recombination is detected by removal of said target site.

* * * * *

SEQUENCE LISTING

```
<160> NUMBER OF SEQ ID NOS: 14

<210> SEQ ID NO 1
<211> LENGTH: 6150
<212> TYPE: DNA
<213> ORGANISM: Artificial Sequence
<220> FEATURE:
<221> NAME/KEY: misc_feature
<222> LOCATION: (1)..(6150)
<223> OTHER INFORMATION: plasmid pBAD24-rec ET
<220> FEATURE:
<221> NAME/KEY: misc_feature
<222> LOCATION: (96)..(974)
<223> OTHER INFORMATION: product = "araC"
<220> FEATURE:
<221> NAME/KEY: misc_feature
<222> LOCATION: (1320)..(2162)
<223> OTHER INFORMATION: product = "t-recE"
<220> FEATURE:
<221> NAME/KEY: misc_feature
<222> LOCATION: (2155)..(2972)
<223> OTHER INFORMATION: product = "recT"
<220> FEATURE:
<221> NAME/KEY: misc_feature
<222> LOCATION: (3493)..(4353)
<223> OTHER INFORMATION: product = "bla"

<400> SEQUENCE: 1
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt  cttcacaacc ggcacggaac tcgctcgggc tggccccggt gcatttttta     180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
```

```
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttccccct tgcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840 taaccttttca ttcccagcgg tcggtcgata aaaaaatcga gataaccgtt ggcctcaatc    900
ggcgttaaac ccgccaccag atgggcatta acgagtatc ccggcagcag gggatcattt    960
tgcgcttcag cctactttt catactcccg ccattcagag aagaaaccaa ttgtccatat   1020
tgcatcagac attgccgtca ctgcgtcttt tactggctct ctcgctaac caaaccggta   1080 acccccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgctttta   1260 tcgcaactct ctactgtttc tccataccccg ttttttttggg ctagcaggag gaattcacca   1320
tggatcccgt aatcgtagaa gacatagagc caggtattta ttacggaatt cgaatgaga   1380 attaccacgc gggtcccggt atcagtaagt ctcagctcga tgacattgct gatactccgg   1440
cactatattt gtggcgtaaa aatgcccccg tggacaccac aaagacaaaa acgctcgatt   1500
taggaactgc tttccactgc cgggtacttg aaccggaaga attcagtaac cgctttatcg   1560
tagcacctga atttaaccgc cgtacaaacg ccggaaaaga agaagagaaa gcgtttctga   1620
tggaatgcgc aagcacagga aaaacggtta tcactgcgga agaaggccgg aaaattgaac   1680
tcatgtatca aagcgttatg ctttgccgc tggggcaatg gcttgttgaa agcgccggac   1740
acgctgaatc atcaatttac tgggaagatc ctgaaacagg aattttgtgt cggtgccgtc   1800
cggacaaaat tatccctgaa tttcactgga tcatggacgt gaaaactacg gcggatattc   1860
aacgattcaa aaccgcttat tacgactacc gctatcacgt tcaggatgca ttctacagtg   1920
acggttatga agcacagttt ggagtgcagc aactttcgt ttttctggtt gccagcacaa   1980
ctattgaatg cggacgttat ccggttgaaa ttttcatgat gggcgaagaa gcaaaactgg   2040
caggtcaaca ggaatatcac cgcaatctgc gaaccctgtc tgactgcctg aataccgatg   2100
aatggccagc tattaagaca ttatcactgc cccgctgggc taaggaatat gcaaatgact   2160
aagcaaccac caatcgcaaa agccgatctg caaaaaactc agggaaaccg tgcaccagca   2220
gcagttaaaa atagcgacgt gattagtttt attaaccagc catcaatgaa agagcaactg   2280
gcagcagctc ttccacgcca tatgacggct gaacgtatga tccgtatcgc caccacagaa   2340
attcgtaaag ttccggcgtt aggaaactgt gacactatga gttttgtcag tcgatcgta   2400 cagtgttcac agctcggact tgagccaggt agcgccctcg gtcatgcata tttactgcct   2460
tttggtaata aaaacgaaaa gagcggtaaa aagaacgttc agctaatcat tggctatcgc   2520
ggcatgattg atctggctcg ccgttctggt caaatcgcca gcctgtcagc ccgtgttgtc   2580
cgtgaaggtg acgagtttag cttcgaattt ggccttgatg aaaagttaat acaccgcccg   2640
ggagaaaacg aagatgcccc ggttacccac gtctatgctg tcgcaagact gaaagacgga   2700
```

```
ggtactcagt tgaagttat gacgcgcaaa cagattgagc tggtgcgcag cctgagtaaa    2760
gctggtaata acgggccgtg ggtaactcac tgggaagaaa tggcaaagaa aacggctatt    2820
cgtcgcctgt tcaaatattt gcccgtatca attgagatcc agcgtgcagt atcaatggat    2880
gaaaaggaac cactgacaat cgatcctgca gattcctctg tattaaccgg ggaatacagt    2940
gtaatcgata attcagagga atagatctaa gcttggctgt tttggcggat gagagaagat    3000
tttcagcctg atacagatta aatcagaacg cagaagcggt ctgataaaac agaatttgcc    3060
tggcggcagt agcgcggtgg tcccacctga ccccatgccg aactcagaag tgaaacgccg    3120
tagcgccgat ggtagtgtgg ggtctcccca tgcgagagta gggaactgcc aggcatcaaa    3180
taaaacgaaa ggctcagtcg aaagactggg cctttcgttt tatctgttgt ttgtcggtga    3240
acgctctcct gagtaggaca atccgccgg gagcggattt gaacgttgcg aagcaacggc    3300
ccggagggtg gcgggcagga cgcccgccat aaactgccag gcatcaaatt aagcagaagg    3360
ccatcctgac ggatggcctt tttgcgtttc tacaaactct tttgtttatt tttctaaata    3420
cattcaaata tgtatccgct catgagacaa taaccctgat aaatgcttca ataatattga    3480
aaaaggaaga gtatgagtat tcaacatttc cgtgtcgccc ttattccctt ttttgcggca    3540
ttttgccttc ctgttttgc tcacccagaa acgctggtga agtaaaaga tgctgaagat    3600 cagttgggtg cacgagtggg ttacatcgaa ctggatctca acagcggtaa gatccttgag    3660
agttttcgcc ccgaagaacg ttttccaatg atgagcactt ttaaagttct gctatgtggc    3720
gcggtattat cccgtgttga cgccgggcaa gagcaactcg gtcgccgcat acactattct    3780
cagaatgact tggttgagta ctcaccagtc acagaaaagc atcttacgga tggcatgaca    3840
gtaagagaat tatgcagtgc tgccataacc atgagtgata acactgcggc caacttactt    3900
ctgacaacga tcggaggacc gaaggagcta accgcttttt tgcacaacat ggggatcat    3960 gtaactcgcc ttgatcgttg ggaaccggag ctgaatgaag ccataccaaa cgacgagcgt    4020
gacaccacga tgcctgtagc aatggcaaca acgttgcgca aactattaac tggcgaacta    4080
cttactctag cttcccggca acaattaata gactggatgg aggcggataa agttgcagga    4140
ccacttctgc gctcggccct tccggctggc tggtttattg ctgataaatc tggagccggt    4200
gagcgtgggt ctcgcggtat cattgcagca ctggggccag atggtaagcc ctcccgtatc    4260
gtagttatct acacgacggg gagtcaggca actatggatg aacgaaatag acagatcgct    4320
gagataggtg cctcactgat taagcattgg taactgtcag accaagttta ctcatatata    4380
ctttagattg atttacgcgc cctgtagcgg cgcattaagc gcggcgggtg tggtggttac    4440
gcgcagcgtg accgctacac ttgccagcgc cctagcgccc gctcctttcg ctttcttccc    4500
ttcctttctc gccacgttcg ccggctttcc ccgtcaagct ctaaatcggg ggctcccttt    4560
agggttccga tttagtgctt tacggcacct cgaccccaaa aaacttgatt tgggtgatgg    4620
ttcacgtagt gggccatcgc cctgatagac ggttttcgc cctttgacgt tggagtccac    4680
gttctttaat agtggactct tgttccaaac ttgaacaaca ctcaacccta tctcgggcta    4740
ttcttttgat ttataaggga ttttgccgat ttcggcctat tggttaaaaa atgagctgat    4800
ttaacaaaaa tttaacgcga attttaacaa atattaacg tttacaattt aaaaggatct    4860
aggtgaagat cctttttgat aatctcatga ccaaaatccc ttaacgtgag ttttcgttcc    4920
actgagcgtc agaccccgta gaaaagatca aaggatcttc ttgagatcct ttttttctgc    4980
gcgtaatctg ctgcttgcaa acaaaaaaac caccgctacc agcggtggtt tgtttgccgg    5040
atcaagagct accaactctt tttccgaagg taactggctt cagcagagcg cagataccaa    5100
```

-continued

```
atactgtcct tctagtgtag ccgtagttag gccaccactt caagaactct gtagcaccgc    5160
ctacatacct cgctctgcta atcctgttac cagtggctgc tgccagtggc gataagtcgt    5220
gtcttaccgg gttggactca agacgatagt taccggataa ggcgcagcgg tcgggctgaa    5280
cggggggttc gtgcacacag cccagcttgg agcgaacgac ctacaccgaa ctgagatacc    5340
tacagcgtga gctatgagaa agcgccacgc ttcccgaagg gagaaaggcg gacaggtatc    5400
cggtaagcgg cagggtcgga acaggagagc gcacgaggga gcttccaggg ggaaacgcct    5460
ggtatcttta tagtcctgtc gggtttcgcc acctctgact tgagcgtcga ttttttgtgat   5520 gctcgtcagg ggggcggagc ctatggaaaa acgccagcaa cgcggccttt ttacggttcc    5580
tggccttttg ctggcctttt gctcacatgt tctttcctgc gttatcccct gattctgtgg    5640
ataaccgtat taccgccttt gagtgagctg ataccgctcg ccgcagccga acgaccgagc    5700
gcagcgagtc agtgagcgag gaagcggaag agcgcctgat gcggtatttt ctccttacgc    5760
atctgtgcgg tatttcacac cgcataggt catggctgcg ccccgacacc cgccaacacc     5820
cgctgacgcg ccctgacggg cttgtctgct cccggcatcc gcttacagac aagctgtgac    5880
cgtctccggg agctgcatgt gtcagaggtt ttcaccgtca tcaccgaaac gcgcgaggca    5940
gcaaggagat ggcgcccaac agtccccgg ccacggggcc tgccaccata cccacgccga     6000
aacaagcgct catgagcccg aagtggcgag cccgatcttc cccatcggtg atgtcggcga    6060
tataggcgcc agcaaccgca cctgtggcgc cggtgatgcc ggccacgatg cgtccggcgt    6120
agaggatctg ctcatgtttg acagcttatc                                    6150
```

<210> SEQ ID NO 2
<211> LENGTH: 843
<212> TYPE: DNA
<213> ORGANISM: Artificial Sequence
<220> FEATURE:
<221> NAME/KEY: misc_feature
<222> LOCATION: (1)..(843)
<223> OTHER INFORMATION: t-recE on plasmid pBAD24-recET at 1320-2162
<220> FEATURE:
<221> NAME/KEY: CDS
<222> LOCATION: (1)..(843)
<223> OTHER INFORMATION: t-recE

<400> SEQUENCE: 2

```
atg gat ccc gta atc gta gaa gac ata gag cca ggt att tat tac gga         48
Met Asp Pro Val Ile Val Glu Asp Ile Glu Pro Gly Ile Tyr Tyr Gly
  1               5                  10                  15 att tcg aat gag aat tac cac gcg ggt ccc ggt atc agt aag tct cag         96
Ile Ser Asn Glu Asn Tyr His Ala Gly Pro Gly Ile Ser Lys Ser Gln
             20                  25                  30 ctc gat gac att gct gat act ccg gca cta tat ttg tgg cgt aaa aat       144
Leu Asp Asp Ile Ala Asp Thr Pro Ala Leu Tyr Leu Trp Arg Lys Asn
         35                  40                  45 gcc ccc gtg gac acc aca aag aca aaa acg ctc gat tta gga act gct       192
Ala Pro Val Asp Thr Thr Lys Thr Lys Thr Leu Asp Leu Gly Thr Ala
     50                  55                  60 ttc cac tgc cgg gta ctt gaa ccg gaa gaa ttc agt aac cgc ttt atc       240
Phe His Cys Arg Val Leu Glu Pro Glu Glu Phe Ser Asn Arg Phe Ile
 65                  70                  75                  80 gta gca cct gaa ttt aac cgc cgt aca aac gcc gga aaa gaa gaa gag       288
Val Ala Pro Glu Phe Asn Arg Arg Thr Asn Ala Gly Lys Glu Glu Glu
                 85                  90                  95 aaa gcg ttt ctg atg gaa tgc gca agc aca gga aaa acg gtt atc act       336
Lys Ala Phe Leu Met Glu Cys Ala Ser Thr Gly Lys Thr Val Ile Thr
```

```
                    100                 105                 110
gcg gaa gaa ggc cgg aaa att gaa ctc atg tat caa agc gtt atg gct    384
Ala Glu Glu Gly Arg Lys Ile Glu Leu Met Tyr Gln Ser Val Met Ala
            115                 120                 125 ttg ccg ctg ggg caa tgg ctt gtt gaa agc gcc gga cac gct gaa tca    432
Leu Pro Leu Gly Gln Trp Leu Val Glu Ser Ala Gly His Ala Glu Ser
        130                 135                 140 tca att tac tgg gaa gat cct gaa aca gga att ttg tgt cgg tgc cgt    480
Ser Ile Tyr Trp Glu Asp Pro Glu Thr Gly Ile Leu Cys Arg Cys Arg
145                 150                 155                 160 ccg gac aaa att atc cct gaa ttt cac tgg atc atg gac gtg aaa act    528
Pro Asp Lys Ile Ile Pro Glu Phe His Trp Ile Met Asp Val Lys Thr
                165                 170                 175 acg gcg gat att caa cga ttc aaa acc gct tat tac gac tac cgc tat    576
Thr Ala Asp Ile Gln Arg Phe Lys Thr Ala Tyr Tyr Asp Tyr Arg Tyr
            180                 185                 190 cac gtt cag gat gca ttc tac agt gac ggt tat gaa gca cag ttt gga    624
His Val Gln Asp Ala Phe Tyr Ser Asp Gly Tyr Glu Ala Gln Phe Gly
        195                 200                 205 gtg cag cca act ttc gtt ttt ctg gtt gcc agc aca act att gaa tgc    672
Val Gln Pro Thr Phe Val Phe Leu Val Ala Ser Thr Thr Ile Glu Cys
    210                 215                 220 gga cgt tat ccg gtt gaa att ttc atg atg ggc gaa gaa gca aaa ctg    720
Gly Arg Tyr Pro Val Glu Ile Phe Met Met Gly Glu Glu Ala Lys Leu
225                 230                 235                 240 gca ggt caa cag gaa tat cac cgc aat ctg cga acc ctg tct gac tgc    768
Ala Gly Gln Gln Glu Tyr His Arg Asn Leu Arg Thr Leu Ser Asp Cys
                245                 250                 255 ctg aat acc gat gaa tgg cca gct att aag aca tta tca ctg ccc cgc    816
Leu Asn Thr Asp Glu Trp Pro Ala Ile Lys Thr Leu Ser Leu Pro Arg
            260                 265                 270 tgg gct aag gaa tat gca aat gac taa                                843
Trp Ala Lys Glu Tyr Ala Asn Asp *
        275                 280

<210> SEQ ID NO 3
<211> LENGTH: 280
<212> TYPE: PRT
<213> ORGANISM: Artificial Sequence
<220> FEATURE:
<221> NAME/KEY: misc_feature
<222> LOCATION: (1)..(280)
<223> OTHER INFORMATION: t-recE on plasmid pBAD24-recET at 1320-2162

<400> SEQUENCE: 3

Met Asp Pro Val Ile Val Glu Asp Ile Glu Pro Gly Ile Tyr Tyr Gly
1               5                   10                  15

Ile Ser Asn Glu Asn Tyr His Ala Gly Pro Gly Ile Ser Lys Ser Gln
            20                  25                  30

Leu Asp Asp Ile Ala Asp Thr Pro Ala Leu Tyr Leu Trp Arg Lys Asn
        35                  40                  45

Ala Pro Val Asp Thr Thr Lys Thr Lys Thr Leu Asp Leu Gly Thr Ala
    50                  55                  60

Phe His Cys Arg Val Leu Glu Pro Glu Glu Phe Ser Asn Arg Phe Ile
65                  70                  75                  80

Val Ala Pro Glu Phe Asn Arg Arg Thr Asn Ala Gly Lys Glu Glu Glu
                85                  90                  95

Lys Ala Phe Leu Met Glu Cys Ala Ser Thr Gly Lys Thr Val Ile Thr
            100                 105                 110
```

```
Ala Glu Glu Gly Arg Lys Ile Glu Leu Met Tyr Gln Ser Val Met Ala
            115                 120                 125

Leu Pro Leu Gly Gln Trp Leu Val Glu Ser Ala Gly His Ala Glu Ser
        130                 135                 140

Ser Ile Tyr Trp Glu Asp Pro Glu Thr Gly Ile Leu Cys Arg Cys Arg
145                 150                 155                 160

Pro Asp Lys Ile Ile Pro Glu Phe His Trp Ile Met Asp Val Lys Thr
                165                 170                 175

Thr Ala Asp Ile Gln Arg Phe Lys Thr Ala Tyr Tyr Asp Tyr Arg Tyr
            180                 185                 190

His Val Gln Asp Ala Phe Tyr Ser Asp Gly Tyr Glu Ala Gln Phe Gly
        195                 200                 205

Val Gln Pro Thr Phe Val Phe Leu Val Ala Ser Thr Thr Ile Glu Cys
    210                 215                 220

Gly Arg Tyr Pro Val Glu Ile Phe Met Met Gly Glu Glu Ala Lys Leu
225                 230                 235                 240

Ala Gly Gln Gln Glu Tyr His Arg Asn Leu Arg Thr Leu Ser Asp Cys
                245                 250                 255

Leu Asn Thr Asp Glu Trp Pro Ala Ile Lys Thr Leu Ser Leu Pro Arg
            260                 265                 270

Trp Ala Lys Glu Tyr Ala Asn Asp
        275                 280

<210> SEQ ID NO 4
<211> LENGTH: 810
<212> TYPE: DNA
<213> ORGANISM: Artificial Sequence
<220> FEATURE:
<221> NAME/KEY: misc_feature
<222> LOCATION: (1)..(810)
<223> OTHER INFORMATION: recT on plasmid pBAD24-recET at 2155-2972
<220> FEATURE:
<221> NAME/KEY: CDS
<222> LOCATION: (1)..(810)
<223> OTHER INFORMATION: recT

<400> SEQUENCE: 4 atg act aag caa cca cca atc gca aaa gcc gat ctg caa aaa act cag      48
Met Thr Lys Gln Pro Pro Ile Ala Lys Ala Asp Leu Gln Lys Thr Gln
            285                 290                 295 gga aac cgt gca cca gca gca gtt aaa aat agc gac gtg att agt ttt      96
Gly Asn Arg Ala Pro Ala Ala Val Lys Asn Ser Asp Val Ile Ser Phe
        300                 305                 310 att aac cag cca tca atg aaa gag caa ctg gca gca gct ctt cca cgc     144
Ile Asn Gln Pro Ser Met Lys Glu Gln Leu Ala Ala Ala Leu Pro Arg
    315                 320                 325 cat atg acg gct gaa cgt atg atc cgt atc gcc acc aca gaa att cgt     192
His Met Thr Ala Glu Arg Met Ile Arg Ile Ala Thr Thr Glu Ile Arg
330                 335                 340                 345 aaa gtt ccg gcg tta gga aac tgt gac act atg agt ttt gtc agt gcg     240
Lys Val Pro Ala Leu Gly Asn Cys Asp Thr Met Ser Phe Val Ser Ala
                350                 355                 360 atc gta cag tgt tca cag ctc gga ctt gag cca ggt agc gcc ctc ggt     288
Ile Val Gln Cys Ser Gln Leu Gly Leu Glu Pro Gly Ser Ala Leu Gly
            365                 370                 375 cat gca tat tta ctg cct ttt ggt aat aaa aac gaa aag agc ggt aaa     336
His Ala Tyr Leu Leu Pro Phe Gly Asn Lys Asn Glu Lys Ser Gly Lys
        380                 385                 390 aag aac gtt cag cta atc att ggc tat cgc ggc atg att gat ctg gct     384
Lys Asn Val Gln Leu Ile Ile Gly Tyr Arg Gly Met Ile Asp Leu Ala
```

-continued

```
                395                 400                 405
cgc cgt tct ggt caa atc gcc agc ctg tca gcc cgt gtt gtc cgt gaa      432
Arg Arg Ser Gly Gln Ile Ala Ser Leu Ser Ala Arg Val Val Arg Glu
410             415                 420                 425 ggt gac gag ttt agc ttc gaa ttt ggc ctt gat gaa aag tta ata cac      480
Gly Asp Glu Phe Ser Phe Glu Phe Gly Leu Asp Glu Lys Leu Ile His
                    430                 435                 440 cgc ccg gga gaa aac gaa gat gcc ccg gtt acc cac gtc tat gct gtc      528
Arg Pro Gly Glu Asn Glu Asp Ala Pro Val Thr His Val Tyr Ala Val
                445                 450                 455 gca aga ctg aaa gac gga ggt act cag ttt gaa gtt atg acg cgc aaa      576
Ala Arg Leu Lys Asp Gly Gly Thr Gln Phe Glu Val Met Thr Arg Lys
            460                 465                 470 cag att gag ctg gtg cgc agc ctg agt aaa gct ggt aat aac ggg ccg      624
Gln Ile Glu Leu Val Arg Ser Leu Ser Lys Ala Gly Asn Asn Gly Pro
        475                 480                 485 tgg gta act cac tgg gaa gaa atg gca aag aaa acg gct att cgt cgc      672
Trp Val Thr His Trp Glu Glu Met Ala Lys Lys Thr Ala Ile Arg Arg
490                 495                 500                 505 ctg ttc aaa tat ttg ccc gta tca att gag atc cag cgt gca gta tca      720
Leu Phe Lys Tyr Leu Pro Val Ser Ile Glu Ile Gln Arg Ala Val Ser
                    510                 515                 520 atg gat gaa aag gaa cca ctg aca atc gat cct gca gat tcc tct gta      768
Met Asp Glu Lys Glu Pro Leu Thr Ile Asp Pro Ala Asp Ser Ser Val
                525                 530                 535 tta acc ggg gaa tac agt gta atc gat aat tca gag gaa tag              810
Leu Thr Gly Glu Tyr Ser Val Ile Asp Asn Ser Glu Glu *
            540                 545                 550

<210> SEQ ID NO 5
<211> LENGTH: 269
<212> TYPE: PRT
<213> ORGANISM: Artificial Sequence
<220> FEATURE:
<221> NAME/KEY: misc_feature
<222> LOCATION: (1)..(269)
<223> OTHER INFORMATION: recT on plasmid pBAD24-recET at 2155-2972

<400> SEQUENCE: 5

Met Thr Lys Gln Pro Pro Ile Ala Lys Ala Asp Leu Gln Lys Thr Gln
1               5                   10                  15

Gly Asn Arg Ala Pro Ala Ala Val Lys Asn Ser Asp Val Ile Ser Phe
            20                  25                  30

Ile Asn Gln Pro Ser Met Lys Glu Gln Leu Ala Ala Ala Leu Pro Arg
        35                  40                  45

His Met Thr Ala Glu Arg Met Ile Arg Ile Ala Thr Thr Glu Ile Arg
    50                  55                  60

Lys Val Pro Ala Leu Gly Asn Cys Asp Thr Met Ser Phe Val Ser Ala
65                  70                  75                  80

Ile Val Gln Cys Ser Gln Leu Gly Leu Glu Pro Gly Ser Ala Leu Gly
                85                  90                  95

His Ala Tyr Leu Leu Pro Phe Gly Asn Lys Asn Glu Lys Ser Gly Lys
            100                 105                 110

Lys Asn Val Gln Leu Ile Ile Gly Tyr Arg Gly Met Ile Asp Leu Ala
        115                 120                 125

Arg Arg Ser Gly Gln Ile Ala Ser Leu Ser Ala Arg Val Val Arg Glu
    130                 135                 140

Gly Asp Glu Phe Ser Phe Glu Phe Gly Leu Asp Glu Lys Leu Ile His
145                 150                 155                 160
```

```
Arg Pro Gly Glu Asn Glu Asp Ala Pro Val Thr His Val Tyr Ala Val
                165                 170                 175

Ala Arg Leu Lys Asp Gly Gly Thr Gln Phe Glu Val Met Thr Arg Lys
            180                 185                 190

Gln Ile Glu Leu Val Arg Ser Leu Ser Lys Ala Gly Asn Asn Gly Pro
        195                 200                 205

Trp Val Thr His Trp Glu Met Ala Lys Lys Thr Ala Ile Arg Arg
    210                 215                 220

Leu Phe Lys Tyr Leu Pro Val Ser Ile Glu Ile Gln Arg Ala Val Ser
225                 230                 235                 240

Met Asp Glu Lys Glu Pro Leu Thr Ile Asp Pro Ala Asp Ser Ser Val
                245                 250                 255

Leu Thr Gly Glu Tyr Ser Val Ile Asp Asn Ser Glu Glu
                260                 265

<210> SEQ ID NO 6
<211> LENGTH: 876
<212> TYPE: DNA
<213> ORGANISM: Artificial Sequence
<220> FEATURE:
<221> NAME/KEY: misc_feature
<222> LOCATION: (1)..(876)
<223> OTHER INFORMATION: araC on plasmid pBAD24-recET at 974-996
<220> FEATURE:
<221> NAME/KEY: CDS
<222> LOCATION: (1)..(876)
<223> OTHER INFORMATION: araC

<400> SEQUENCE: 6
tgacaacttg acggctacat cattcacttt ttcttcacaa ccggcacgga actcgctcgg      60
gctggccccg gtgcattttt taaatacccg cgagaaatag agttgatcgt caaaaccaac    120
attgcgaccg acggtggcga taggcatccg ggtggtgctc aaaagcagct tcgcctggct    180
gatacgttgg tcctcgcgcc agcttaagac gctaatccct aactgctggc ggaaaagatg    240
tgacagacgc gacggcgaca agcaaacatg ctgtgcgacg ctggcgatat caaaattgct    300
gtctgccagg tgatcgctga tgtactgaca agcctcgcgt acccgattat ccatcggtgg    360
atggagcgac tcgttaatcg cttccatgcg ccgcagtaac aattgctcaa gcagatttat    420
cgccagcagc tccgaatagc gcccttcccc ttgcccggcg ttaatgattt gcccaaacag    480
gtcgctgaaa tgcggctggt gcgcttcatc cgggcgaaag aaccccgtat tggcaaatat    540
tgacggccag ttaagccatt catgccagta ggcgcgcgga cgaaagtaaa cccactggtg    600
ataccattcg cgagcctccg gatgacgacc gtagtgatga atctctcctg gcgggaacag    660
caaaatatca cccggtcggc aaacaaattc tcgtccctga ttttttcacca ccccctgacc    720
gcgaatggtg agattgagaa tataaccttt cattcccagc ggtcggtcga taaaaaaatc    780
gagataaccg ttggcctcaa tcggcgttaa acccgccacc agatgggcat taaacgagta    840
tcccggcagc aggggatcat tttgcgcttc agccat                               876

<210> SEQ ID NO 7
<211> LENGTH: 292
<212> TYPE: PRT
<213> ORGANISM: Artificial Sequence
<220> FEATURE:
<221> NAME/KEY: misc_feature
<222> LOCATION: (1)..(292)
<223> OTHER INFORMATION: araC on plasmid pBAD24-recET at 974-996

<400> SEQUENCE: 7
```

```
Met Ala Glu Ala Gln Asn Asp Pro Leu Leu Pro Gly Tyr Ser Phe Asn
 1               5                   10                  15

Ala His Leu Val Ala Gly Leu Thr Pro Ile Glu Ala Asn Gly Tyr Leu
            20                  25                  30

Asp Phe Phe Ile Asp Arg Pro Leu Gly Met Lys Gly Tyr Ile Leu Asn
        35                  40                  45

Leu Thr Ile Arg Gly Gln Gly Val Val Lys Asn Gln Gly Arg Glu Phe
    50                  55                  60

Val Cys Arg Pro Gly Asp Ile Leu Leu Phe Pro Pro Gly Glu Ile His
65                  70                  75                  80

His Tyr Gly Arg His Pro Glu Ala Arg Glu Trp Tyr His Gln Trp Val
                85                  90                  95

Tyr Phe Arg Pro Arg Ala Tyr Trp His Glu Trp Leu Asn Trp Pro Ser
            100                 105                 110

Ile Phe Ala Asn Thr Gly Phe Phe Arg Pro Asp Glu Ala His Gln Pro
        115                 120                 125

His Phe Ser Asp Leu Phe Gly Gln Ile Ile Asn Ala Gly Gln Gly Glu
    130                 135                 140

Gly Arg Tyr Ser Glu Leu Leu Ala Ile Asn Leu Leu Glu Gln Leu Leu
145                 150                 155                 160

Leu Arg Arg Met Glu Ala Ile Asn Glu Ser Leu His Pro Pro Met Asp
                165                 170                 175

Asn Arg Val Arg Glu Ala Cys Gln Tyr Ile Ser Asp His Leu Ala Asp
            180                 185                 190

Ser Asn Phe Asp Ile Ala Ser Val Ala Gln His Val Cys Leu Ser Pro
        195                 200                 205

Ser Arg Leu Ser His Leu Phe Arg Gln Gln Leu Gly Ile Ser Val Leu
    210                 215                 220

Ser Trp Arg Glu Asp Gln Arg Ile Ser Gln Ala Lys Leu Leu Leu Ser
225                 230                 235                 240

Thr Thr Arg Met Pro Ile Ala Thr Val Gly Arg Asn Val Gly Phe Asp
                245                 250                 255

Asp Gln Leu Tyr Phe Ser Arg Val Phe Lys Lys Cys Thr Gly Ala Ser
            260                 265                 270

Pro Ser Glu Phe Arg Ala Gly Cys Glu Glu Lys Val Asn Asp Val Ala
        275                 280                 285

Val Lys Leu Ser
    290

<210> SEQ ID NO 8
<211> LENGTH: 861
<212> TYPE: DNA
<213> ORGANISM: Artificial Sequence
<220> FEATURE:
<221> NAME/KEY: misc_feature
<222> LOCATION: (1)..(861)
<223> OTHER INFORMATION: bla gene on plasmid pBAD24-recET at 3493-4353
<220> FEATURE:
<221> NAME/KEY: CDS
<222> LOCATION: (1)..(861)
<223> OTHER INFORMATION: bla

<400> SEQUENCE: 8 atg agt att caa cat ttc cgt gtc gcc ctt att ccc ttt ttt gcg gca    48
Met Ser Ile Gln His Phe Arg Val Ala Leu Ile Pro Phe Phe Ala Ala
        295                 300                 305 ttt tgc ctt cct gtt ttt gct cac cca gaa acg ctg gtg aaa gta aaa    96
```

```
gat gct gaa gat cag ttg ggt gca cga gtg ggt tac atc gaa ctg gat      144
Asp Ala Glu Asp Gln Leu Gly Ala Arg Val Gly Tyr Ile Glu Leu Asp
325                 330                 335                 340 ctc aac agc ggt aag atc ctt gag agt ttt cgc ccc gaa gaa cgt ttt      192
Leu Asn Ser Gly Lys Ile Leu Glu Ser Phe Arg Pro Glu Glu Arg Phe
                345                 350                 355 cca atg atg agc act ttt aaa gtt ctg cta tgt ggc gcg gta tta tcc      240
Pro Met Met Ser Thr Phe Lys Val Leu Leu Cys Gly Ala Val Leu Ser
            360                 365                 370 cgt gtt gac gcc ggg caa gag caa ctc ggt cgc cgc ata cac tat tct      288
Arg Val Asp Ala Gly Gln Glu Gln Leu Gly Arg Arg Ile His Tyr Ser
        375                 380                 385 cag aat gac ttg gtt gag tac tca cca gtc aca gaa aag cat ctt acg      336
Gln Asn Asp Leu Val Glu Tyr Ser Pro Val Thr Glu Lys His Leu Thr
    390                 395                 400 gat ggc atg aca gta aga gaa tta tgc agt gct gcc ata acc atg agt      384
Asp Gly Met Thr Val Arg Glu Leu Cys Ser Ala Ala Ile Thr Met Ser
405                 410                 415                 420 gat aac act gcg gcc aac tta ctt ctg aca acg atc gga gga ccg aag      432
Asp Asn Thr Ala Ala Asn Leu Leu Leu Thr Thr Ile Gly Gly Pro Lys
                425                 430                 435 gag cta acc gct ttt ttg cac aac atg ggg gat cat gta act cgc ctt      480
Glu Leu Thr Ala Phe Leu His Asn Met Gly Asp His Val Thr Arg Leu
            440                 445                 450 gat cgt tgg gaa ccg gag ctg aat gaa gcc ata cca aac gac gag cgt      528
Asp Arg Trp Glu Pro Glu Leu Asn Glu Ala Ile Pro Asn Asp Glu Arg
        455                 460                 465 gac acc acg atg cct gta gca atg gca aca acg ttg cgc aaa cta tta      576
Asp Thr Thr Met Pro Val Ala Met Ala Thr Thr Leu Arg Lys Leu Leu
    470                 475                 480 act ggc gaa cta ctt act cta gct tcc cgg caa caa tta ata gac tgg      624
Thr Gly Glu Leu Leu Thr Leu Ala Ser Arg Gln Gln Leu Ile Asp Trp
485                 490                 495                 500 atg gag gcg gat aaa gtt gca gga cca ctt ctg cgc tcg gcc ctt ccg      672
Met Glu Ala Asp Lys Val Ala Gly Pro Leu Leu Arg Ser Ala Leu Pro
                505                 510                 515 gct ggc tgg ttt att gct gat aaa tct gga gcc ggt gag cgt ggg tct      720
Ala Gly Trp Phe Ile Ala Asp Lys Ser Gly Ala Gly Glu Arg Gly Ser
            520                 525                 530 cgc ggt atc att gca gca ctg ggg cca gat ggt aag ccc tcc cgt atc      768
Arg Gly Ile Ile Ala Ala Leu Gly Pro Asp Gly Lys Pro Ser Arg Ile
        535                 540                 545 gta gtt atc tac acg acg ggg agt cag gca act atg gat gaa cga aat      816
Val Val Ile Tyr Thr Thr Gly Ser Gln Ala Thr Met Asp Glu Arg Asn
    550                 555                 560 aga cag atc gct gag ata ggt gcc tca ctg att aag cat tgg taa          861
Arg Gln Ile Ala Glu Ile Gly Ala Ser Leu Ile Lys His Trp *
565                 570                 575
```

<210> SEQ ID NO 9
<211> LENGTH: 286
<212> TYPE: PRT
<213> ORGANISM: Artificial Sequence
<220> FEATURE:
<221> NAME/KEY: DOMAIN
<222> LOCATION: (1)..(286)
<223> OTHER INFORMATION: bla gene on plasmid pBAD24-recET at 3493-4353

<400> SEQUENCE: 9

Phe Cys Leu Pro Val Phe Ala His Pro Glu Thr Leu Val Lys Val Lys
310                 315                 320

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Arg Phe
     50                  55                  60

Pro Met Met Ser Thr Phe Lys Val Leu Leu Cys Gly Ala Val Leu Ser
 65                  70                  75                  80

Arg Val Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285

<210> SEQ ID NO 10
<211> LENGTH: 7195
<212> TYPE: DNA
<213> ORGANISM: Artificial Sequence
<220> FEATURE:
<221> NAME/KEY: misc_feature
<222> LOCATION: (1)..(7195)
<223> OTHER INFORMATION: plasmid pBAD-ET-gamma
<220> FEATURE:
<221> NAME/KEY: CDS
<222> LOCATION: (1)..(7195)
<223> OTHER INFORMATION: red gamma

<400> SEQUENCE: 10
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120 ttcactttt cttcacaacc ggcacggaac tcgctcgggc tggccccggt gcattttta     180 aataccgcg agaaatagag ttgatcgtca aaaccaacat tgcgaccgac ggtggcgata     240
ggcatccggg tggtgctcaa aagcagcttc gcctggctga tacgttggtc ctcgcgccag     300
```

```
cttaagacgc taatccctaa ctgctggcgg aaaagatgtg acagacgcga cggcgacaag    360
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttcccctt gcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatcc ccggcagcag gggatcattt    960
tgcgcttcag ccatactttt catactcccg ccattcagag aagaaaccaa ttgtccatat   1020
tgcatcagac attgccgtca ctgcgtcttt tactggctct tctcgctaac caaaccggta   1080
accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgcttttta   1260
tcgcaactct ctactgtttc tccatacccg ttttttttggg ctagcaggag gaattcacca   1320
tggatcccgt aatcgtagaa gacatagagc caggtattta ttacggaatt tcgaatgaga   1380
attaccacgc gggtcccggt atcagtaagt ctcagctcga tgacattgct gatactccgg   1440
cactatattt gtggcgtaaa aatgcccccg tggacaccac aaagacaaaa acgctcgatt   1500
taggaactgc tttccactgc cgggtacttg aaccggaaga attcagtaac cgctttatcg   1560
tagcacctga atttaaccgc cgtacaaacg ccggaaaaga agaagagaaa gcgtttctga   1620
tggaatgcgc aagcacagga aaaacggtta tcactgcgga agaaggccgg aaaattgaac   1680
tcatgtatca aagcgttatg gctttgccgc tggggcaatg gcttgttgaa agcgccggac   1740
acgctgaatc atcaatttac tgggaagatc ctgaaacagg aattttgtgt cggtgccgtc   1800
cggacaaaat tatccctgaa tttcactgga tcatggacgt gaaaactacg gcggatattc   1860
aacgattcaa aaccgcttat tacgactacc gctatcacgt tcaggatgca ttctacagtg   1920
acggttatga agcacagttt ggagtgcagc caactttcgt ttttctggtt gccagcacaa   1980
ctattgaatg cggacgttat ccggttgaaa ttttcatgat gggcgaagaa gcaaaactgg   2040
caggtcaaca ggaatatcac cgcaatctgc gaaccctgtc tgactgcctg aataccgatg   2100
aatggccagc tattaagaca ttatcactgc cccgctgggc taaggaatat gcaaatgact   2160
agatctcgag gtacccgagc acgtgttgac aattaatcat cggcatagta tatcggcata   2220
gtataatacg acaaggtgag gaactaaacc atggctaagc aaccaccaat cgcaaaagcc   2280
gatctgcaaa aaactcaggg aaaccgtgca ccagcagcag ttaaaaatag cgacgtgatt   2340
agttttatta accagccatc aatgaaagag caactggcag cagctcttcc acgccatatg   2400
acggctgaac gtatgatccg tatcgccacc acagaaattc gtaaagttcc ggcgttagga   2460
aactgtgaca ctatgagttt tgtcagtcgc gatcgtacagt gttcacagct cggacttgag   2520
ccaggtagcg ccctcggtca tgcatattta ctgcctttttg gtaataaaaa cgaaaagagc   2580
ggtaaaaaga acgttcagct aatcattggc tatcgcggca tgattgatct ggctcgccgt   2640
```

```
tctggtcaaa tcgccagcct gtcagcccgt gttgtccgtg aaggtgacga gtttagcttc    2700
gaatttggcc ttgatgaaaa gttaatacac cgcccgggag aaaacgaaga tgccccggtt    2760
acccacgtct atgctgtcgc aagactgaaa gacggaggta ctcagtttga agttatgacg    2820
cgcaaacaga ttgagctggt gcgcagcctg agtaaagctg gtaataacgg gccgtgggta    2880
actcactggg aagaaatggc aaagaaaacg ctattcgtc gcctgttcaa atatttgccc     2940
gtatcaattg agatccagcg tgcagtatca atggatgaaa ggaaccact gacaatcgat     3000
cctgcagatt cctctgtatt aaccggggaa tacagtgtaa tcgataattc agaggaatag    3060
atctaagctt cctgctgaac atcaaaggca agaaaacatc tgttgtcaaa gacagcatcc    3120
ttgaacaagg acaattaaca gttaacaaat aaaaacgcaa agaaaatgc cgatatccta     3180
ttggcatttt cttttatttc ttatcaacat aaaggtgaat cccatacctc gagcttcacg    3240
ctgccgcaag cactcagggc gcaagggctg ctaaaaggaa gcggaacacg tagaaagcca    3300
gtccgcagaa acgtgctga ccccggatga atgtcagcta ctgggctatc tggacaaggg     3360
aaaacgcaag cgcaaagaga aagcaggtag cttgcagtgg gcttacatgg cgatagctag    3420
actgggcggt tttatggaca gcaagcgaac cggaattgcc agctggggcg ccctctggta    3480
aggttgggaa gccctgcaaa gtaaactgga tggctttctt gccgccaagg atctgatggc    3540
gcagggatc aagatctgat caagagacag gatgaggatc gtttcgcatg gatattaata    3600
ctgaaactga gatcaagcaa aagcattcac taacccccctt tcctgttttc ctaatcagcc   3660
cggcatttcg cgggcgatat tttcacagct atttcaggag ttcagccatg aacgcttatt    3720
acattcagga tcgtcttgag gctcagagct gggcgcgtca ctaccagcag ctcgcccgtg    3780
aagagaaaga ggcagaactg gcagacgaca tggaaaaagg cctgccccag cacctgtttg    3840
aatcgctatg catcgatcat ttgcaacgcc acggggccag caaaaaatcc attcccgtg     3900
cgtttgatga cgatgttgag tttcaggagc gcatggcaga acacatccgg tacatggttg    3960
aaaccattgc tcaccaccag gttgatattg attcagaggt ataaaacgag tagaagcttg    4020
gctgttttgg cggatgagag aagattttca gcctgataca gattaaatca gaacgcagaa    4080
gcggtctgat aaaacagaat ttgcctggcg gcagtagcgc ggtggtccca cctgaccccca   4140
tgccgaactc agaagtgaaa cgccgtagcg ccgatggtag tgtggggtct ccccatgcga    4200
gagtagggaa ctgccaggca tcaaataaaa cgaaaggctc agtcgaaaga ctgggccttt    4260
cgttttatct gttgtttgtc ggtgaacgct ctcctgagta ggacaaatcc gccgggagcg    4320
gatttgaacg ttgcgaagca acgggcccgga gggtggcggg caggacgccc gccataaact   4380
gccaggcatc aaattaagca gaaggccatc ctgacggatg gcctttttgc gtttctacaa    4440
actcttttgt ttatttttct aaatacattc aaatatgtat ccgctcatga acaataacc     4500
ctgataaatg cttcaataat attgaaaaag gaagagtatg agtattcaac atttccgtgt    4560
cgcccttatt ccctttttg cggcattttg ccttcctgtt tttgctcacc cagaaacgct     4620
ggtgaaagta aaagatgctg aagatcagtt gggtgcacga gtgggttaca tcgaactgga    4680
tctcaacagc ggtaagatcc ttgagagttt tcgccccgaa gaacgttttc caatgatgag    4740
cacttttaaa gttctgctat gtggcgcggt attatcccgt gttgacgccg ggcaagagca    4800
actcggtcgc cgcatacact attctcagaa tgacttggtt gagtactcac cagtcacaga    4860
aaagcatctt acggatggca tgacagtaag agaattatgc agtgctgcca taaccatgag    4920
tgataacact gcggccaact tacttctgac aacgatcgga ggaccgaagg agctaaccgc    4980
ttttttgcac aacatggggg atcatgtaac tcgccttgat cgttgggaac cggagctgaa    5040
```

```
tgaagccata ccaaacgacg agcgtgacac cacgatgcct gtagcaatgg caacaacgtt    5100
gcgcaaacta ttaactggcg aactacttac tctagcttcc cggcaacaat aatagactg    5160 gatggaggcg ataaagttg caggaccact tctgcgctcg cccttccgg ctggctggtt    5220 tattgctgat aaatctggag ccggtgagcg tgggtctcgc ggtatcattg cagcactggg    5280
gccagatggt aagccctccc gtatcgtagt tatctcacg acggggagtc aggcaactat    5340
ggatgaacga atagacaga tcgctgagat aggtgcctca ctgattaagc attggtaact    5400
gtcagaccaa gtttactcat atatacttta gattgattta cgcgcccgt agcggcgcat    5460 taagcgcggc gggtgtggtg gttacgcgca gcgtgaccgc tacacttgcc agcgccctag    5520
cgcccgctcc tttcgctttc ttcccttcct ttctcgccac gttcgccggc tttcccgtc    5580 aagctctaaa tcggggctc cctttagggt tccgatttag tgctttacgg cacctcgacc    5640
ccaaaaaact tgatttgggt gatggttcac gtagtgggcc atcgccctga tagacggttt    5700
ttcgcccttt gacgttggag tccacgttct ttaatagtgg actcttgttc caaacttgaa    5760
caacactcaa ccctatctcg ggctattctt ttgatttata agggattttg ccgatttcgg    5820
cctattggtt aaaaaatgag ctgatttaac aaaaatttaa cgcgaatttt aacaaaatat    5880
taacgtttac aatttaaaag gatctaggtg aagatccttt ttgataatct catgaccaaa    5940
atcccttaac gtgagttttc gttccactga gcgtcagacc ccgtagaaaa gatcaaagga    6000
tcttcttgag atcctttttt tctgcgcgta atctgctgct tgcaaacaaa aaaaccaccg    6060
ctaccagcgg tggtttgttt gccggatcaa gagctaccaa ctctttttcc gaaggtaact    6120
ggcttcagca gagcgcagat accaaatact gtccttctag tgtagccgta gttaggccac    6180
cacttcaaga actctgtagc accgcctaca tacctcgctc tgctaatcct gttaccagtg    6240
gctgctgcca gtggcgataa gtcgtgtctt accgggttgg actcaagacg atagttaccg    6300
gataaggcgc agcggtcggg ctgaacgggg gttcgtgca cacagcccag cttggagcga    6360
acgacctaca ccgaactgag atacctacag cgtgagctat gagaaagcgc cacgcttccc    6420
gaagggagaa aggcggacag gtatccggta agcggcaggg tcggaacagg agagcgcacg    6480
agggagcttc caggggaaa cgcctggtat ctttatagtc ctgtcgggtt tcgccacctc    6540
tgacttgagc gtcgattttt gtgatgctcg tcagggggc ggagcctatg gaaaaacgcc    6600
agcaacgcgg ccttttacg gttcctggcc ttttgctggc cttttgctca catgttcttt    6660
cctgcgttat cccctgattc tgtggataac cgtattaccg cctttgagtg agctgatacc    6720
gctcgccgca gccgaacgac cgagcgcagc gagtcagtga gcgaggaagc ggaagagcgc    6780
ctgatgcggt attttctcct tacgcatctg tgcggtattt cacaccgcat agggtcatgg    6840
ctgcgccccg acaccgcca cacccgctg acgcgccctg acgggcttgt ctgctcccgg    6900
catccgctta cagacaagct gtgaccgtct ccgggagctg catgtgtcag aggttttcac    6960
cgtcatcacc gaaacgcgcg aggcagcaag gagatggcgc ccaacagtcc cccggccacg    7020
gggcctgcca ccatacccac gccgaaacaa gcgctcatga gcccgaagtg gcgagcccga    7080
tcttccccat cggtgatgtc ggcgatatag gcgccagcaa ccgcacctgt ggcgccggtg    7140
atgccggcca cgatgcgtcc ggcgtagagg atctgctcat gtttgacagc ttatc         7195
```

<210> SEQ ID NO 11
<211> LENGTH: 7010
<212> TYPE: DNA
<213> ORGANISM: Artificial Sequence
<220> FEATURE:

-continued

```
<221> NAME/KEY: misc_feature
<222> LOCATION: (1)..(7010)
<223> OTHER INFORMATION: plasmid pBAD-alpha-beta-gamma
<220> FEATURE:
<221> NAME/KEY: CDS
<222> LOCATION: (1320)..(2000)
<223> OTHER INFORMATION: red alpha
<220> FEATURE:
<221> NAME/KEY: CDS
<222> LOCATION: (2086)..(2871)
<223> OTHER INFORMATION: red beta
<220> FEATURE:
<221> NAME/KEY: CDS
<222> LOCATION: (3403)..(3819)
<223> OTHER INFORMATION: red gamma

<400> SEQUENCE: 11
```

| | |
|---|---|
| atcgatgcat aatgtgcctg tcaaatggac gaagcaggga ttctgcaaac cctatgctac | 60 |
| tccgtcaagc cgtcaattgt ctgattcgtt accaattatg acaacttgac ggctacatca | 120 |
| ttcactttt cttcacaacc ggcacggaac tcgctcgggc tggccccggt gcattttta | 180 |
| aatacccgcg agaaatagag ttgatcgtca aaaccaacat tgcgaccgac ggtggcgata | 240 |
| ggcatccggg tggtgctcaa aagcagcttc gcctggctga tacgttggtc ctcgcgccag | 300 |
| cttaagacgc taatccctaa ctgctggcgg aaaagatgtg acagacgcga cggcgacaag | 360 |
| caaacatgct gtgcgacgct ggcgatatca aaattgctgt ctgccaggtg atcgctgatg | 420 |
| tactgacaag cctcgcgtac ccgattatcc atcggtggat ggagcgactc gttaatcgct | 480 |
| tccatgcgcc gcagtaacaa ttgctcaagc agatttatcg ccagcagctc cgaatagcgc | 540 |
| ccttcccctt gcccggcgtt aatgatttgc ccaaacaggt cgctgaaatg cggctggtgc | 600 |
| gcttcatccg ggcgaaagaa ccccgtattg gcaaatattg acggccagtt aagccattca | 660 |
| tgccagtagg cgcgcggacg aaagtaaacc cactggtgat accattcgcg agcctccgga | 720 |
| tgacgaccgt agtgatgaat ctctcctggc gggaacagca aaatatcacc cggtcggcaa | 780 |
| acaaattctc gtccctgatt tttcaccacc ccctgaccgc gaatggtgag attgagaata | 840 |
| taacctttca ttcccagcgg tcggtcgata aaaaaatcga gataaccgtt ggcctcaatc | 900 |
| ggcgttaaac ccgccaccag atgggcatta acgagtatc ccggcagcag gggatcattt | 960 |
| tgcgcttcag ccatactttt catactcccg ccattcagag aagaaaccaa ttgtccatat | 1020 |
| tgcatcagac attgccgtca ctgcgtcttt tactggctct ctcgctaac caaaccggta | 1080 |
| accccgctta ttaaaagcat tctgtaacaa agcgggacca aagccatgac aaaaacgcgt | 1140 |
| aacaaaagtg tctataatca cggcagaaaa gtccacattg ttatttgca cggcgtcaca | 1200 |
| ctttgctatg ccatagcatt tttatccata agattagcgg atcctacctg acgcttttta | 1260 |
| tcgcaactct ctactgtttc tccatacccg ttttttggg ctagcaggag gaattcacc | 1319 |

| | | |
|---|---|---|
| atg aca ccg gac att atc ctg cag cgt acc ggg atc gat gtg aga gct | | 1367 |
| Met Thr Pro Asp Ile Ile Leu Gln Arg Thr Gly Ile Asp Val Arg Ala | | |
| 290 | 295 | 300 |
| gtc gaa cag ggg gat gat gcg tgg cac aaa tta cgg ctc ggc gtc atc | | 1415 |
| Val Glu Gln Gly Asp Asp Ala Trp His Lys Leu Arg Leu Gly Val Ile | | |
| 305 | 310 | 315 |
| acc gct tca gaa gtt cac aac gtg ata gca aaa ccc cgc tcc gga aag | | 1463 |
| Thr Ala Ser Glu Val His Asn Val Ile Ala Lys Pro Arg Ser Gly Lys | | |
| 320 | 325 | 330 | 335 |
| aag tgg cct gac atg aaa atg tcc tac ttc cac acc ctg ctt gct gag | | 1511 |
| Lys Trp Pro Asp Met Lys Met Ser Tyr Phe His Thr Leu Leu Ala Glu | | |
| 340 | 345 | 350 |
| gtt tgc acc ggt gtg gct ccg gaa gtt aac gct aaa gca ctg gcc tgg | | 1559 |

```
                Val Cys Thr Gly Val Ala Pro Glu Val Asn Ala Lys Ala Leu Ala Trp
                            355                 360                 365 gga aaa cag tac gag aac gac gcc aga acc ctg ttt gaa ttc act tcc          1607
Gly Lys Gln Tyr Glu Asn Asp Ala Arg Thr Leu Phe Glu Phe Thr Ser
            370                 375                 380 ggc gtg aat gtt act gaa tcc ccg atc atc tat cgc gac gaa agt atg          1655
Gly Val Asn Val Thr Glu Ser Pro Ile Ile Tyr Arg Asp Glu Ser Met
385                 390                 395 cgt acc gcc tgc tct ccc gat ggt tta tgc agt gac ggc aac ggc ctt          1703
Arg Thr Ala Cys Ser Pro Asp Gly Leu Cys Ser Asp Gly Asn Gly Leu
400                 405                 410                 415 gaa ctg aaa tgc ccg ttt acc tcc cgg gat ttc atg aag ttc cgg ctc          1751
Glu Leu Lys Cys Pro Phe Thr Ser Arg Asp Phe Met Lys Phe Arg Leu
                420                 425                 430 ggt ggt ttc gag gcc ata aag tca gct tac atg gcc cag gtg cag tac          1799
Gly Gly Phe Glu Ala Ile Lys Ser Ala Tyr Met Ala Gln Val Gln Tyr
            435                 440                 445 agc atg tgg gtg acg cga aaa aat gcc tgg tac ttt gcc aac tat gac          1847
Ser Met Trp Val Thr Arg Lys Asn Ala Trp Tyr Phe Ala Asn Tyr Asp
        450                 455                 460 ccg cgt atg aag cgt gaa ggc ctg cat tat gtc gtg att gag cgg gat          1895
Pro Arg Met Lys Arg Glu Gly Leu His Tyr Val Val Ile Glu Arg Asp
        465                 470                 475 gaa aag tac atg gcg agt ttt gac gag atc gtg ccg gag ttc atc gaa          1943
Glu Lys Tyr Met Ala Ser Phe Asp Glu Ile Val Pro Glu Phe Ile Glu
480                 485                 490                 495 aaa atg gac gag gca ctg gct gaa att ggt ttt gta ttt ggg gag caa          1991
Lys Met Asp Glu Ala Leu Ala Glu Ile Gly Phe Val Phe Gly Glu Gln
                500                 505                 510 tgg cga tag atccggtacc cgagcacgtg ttgacaatta atcatcggca                  2040
Trp Arg * tagtatatcg gcatagtata atacgacaag gtgaggaact aaacc atg agt act            2094
                                                    Met Ser Thr
                                                      1 gca ctc gca acg ctg gct ggg aag ctg gct gaa cgt gtc ggc atg gat          2142
Ala Leu Ala Thr Leu Ala Gly Lys Leu Ala Glu Arg Val Gly Met Asp
    5                  10                  15 tct gtc gac cca cag gaa ctg atc acc act ctt cgc cag acg gca ttt          2190
Ser Val Asp Pro Gln Glu Leu Ile Thr Thr Leu Arg Gln Thr Ala Phe
 20                  25                  30                  35 aaa ggt gat gcc agc gat gcg cag ttc atc gca tta ctg atc gtt gcc          2238
Lys Gly Asp Ala Ser Asp Ala Gln Phe Ile Ala Leu Leu Ile Val Ala
                40                  45                  50 aac cag tac ggc ctt aat ccg tgg acg aaa gaa att tac gcc ttt cct          2286
Asn Gln Tyr Gly Leu Asn Pro Trp Thr Lys Glu Ile Tyr Ala Phe Pro
             55                  60                  65 gat aag cag aat ggc atc gtt ccg gtg gtg ggc gtt gat ggc tgg tcc          2334
Asp Lys Gln Asn Gly Ile Val Pro Val Val Gly Val Asp Gly Trp Ser
             70                  75                  80 cgc atc atc aat gaa aac cag cag ttt gat ggc atg gac ttt gag cag          2382
Arg Ile Ile Asn Glu Asn Gln Gln Phe Asp Gly Met Asp Phe Glu Gln
 85                  90                  95 gac aat gaa tcc tgt aca tgc cgg att tac cgc aag gac cgt aat cat          2430
Asp Asn Glu Ser Cys Thr Cys Arg Ile Tyr Arg Lys Asp Arg Asn His
100                 105                 110                 115 ccg atc tgc gtt acc gaa tgg atg gat gaa tgc cgc cgc gaa cca ttc          2478
Pro Ile Cys Val Thr Glu Trp Met Asp Glu Cys Arg Arg Glu Pro Phe
                120                 125                 130 aaa act cgc gaa ggc aga gaa atc acg ggg ccg tgg cag tcg cat ccc          2526
```

```
Lys Thr Arg Glu Gly Arg Glu Ile Thr Gly Pro Trp Gln Ser His Pro
            135                 140                 145 aaa cgg atg tta cgt cat aaa gcc atg att cag tgt gcc cgt ctg gcc      2574
Lys Arg Met Leu Arg His Lys Ala Met Ile Gln Cys Ala Arg Leu Ala
            150                 155                 160 ttc gga ttt gct ggt atc tat gac aag gat gaa gcc gag cgc att gtc      2622
Phe Gly Phe Ala Gly Ile Tyr Asp Lys Asp Glu Ala Glu Arg Ile Val
            165                 170                 175 gaa aat act gca tac act gca gaa cgt cag ccg gaa cgc gac atc act      2670
Glu Asn Thr Ala Tyr Thr Ala Glu Arg Gln Pro Glu Arg Asp Ile Thr
180             185                 190                 195 ccg gtt aac gat gaa acc atg cag gag att aac act ctg ctg atc gcc      2718
Pro Val Asn Asp Glu Thr Met Gln Glu Ile Asn Thr Leu Leu Ile Ala
                200                 205                 210 ctg gat aaa aca tgg gat gac gac tta ttg ccg ctc tgt tcc cag ata      2766
Leu Asp Lys Thr Trp Asp Asp Asp Leu Leu Pro Leu Cys Ser Gln Ile
            215                 220                 225 ttt cgc cgc gac att cgt gca tcg tca gaa ctg aca cag gcc gaa gca      2814
Phe Arg Arg Asp Ile Arg Ala Ser Ser Glu Leu Thr Gln Ala Glu Ala
            230                 235                 240 gta aaa gct ctt gga ttc ctg aaa cag aaa gcc gca gag cag aag gtg      2862
Val Lys Ala Leu Gly Phe Leu Lys Gln Lys Ala Ala Glu Gln Lys Val
245                 250                 255 gca gca tag atctcgagaa gcttcctgct gaacatcaaa ggcaagaaaa              2911
Ala Ala *
260 catctgttgt caaagacagc atccttgaac aaggacaatt aacagttaac aaataaaaac    2971 gcaaaagaaa atgccgatat cctattggca ttttctttta tttcttatca acataaaggt    3031 gaatcccata cctcgagctt cacgctgccg caagcactca gggcgcaagg gctgctaaaa    3091 ggaagcggaa cacgtagaaa gccagtccgc agaaacggtg ctgaccccgg atgaatgtca    3151 gctactgggc tatctggaca agggaaaacg caagcgcaaa gagaaagcag gtagcttgca    3211 gtgggcttac atggcgatag ctagactggg cggttttatg gacagcaagc gaaccggaat    3271 tgccagctgg ggcgccctct ggtaaggttg ggaagccctg caaagtaaac tggatggctt    3331 tcttgccgcc aaggatctga tggcgcaggg gatcaagatc tgatcaagag acaggatgag    3391 gatcgtttcg c atg gat att aat act gaa act gag atc aag caa aag cat    3441
         Met Asp Ile Asn Thr Glu Thr Glu Ile Lys Gln Lys His
           1               5                  10 tca cta acc ccc ttt cct gtt ttc cta atc agc ccg gca ttt cgc ggg      3489
Ser Leu Thr Pro Phe Pro Val Phe Leu Ile Ser Pro Ala Phe Arg Gly
            15                  20                  25 cga tat ttt cac agc tat ttc agg agt tca gcc atg aac gct tat tac      3537
Arg Tyr Phe His Ser Tyr Phe Arg Ser Ser Ala Met Asn Ala Tyr Tyr
30              35                  40                  45 att cag gat cgt ctt gag gct cag agc tgg gcg cgt cac tac cag cag      3585
Ile Gln Asp Arg Leu Glu Ala Gln Ser Trp Ala Arg His Tyr Gln Gln
                50                  55                  60 ctc gcc cgt gaa gag aaa gag gca gaa ctg gca gac gac atg gaa aaa      3633
Leu Ala Arg Glu Glu Lys Glu Ala Glu Leu Ala Asp Asp Met Glu Lys
            65                  70                  75 ggc ctg ccc cag cac ctg ttt gaa tcg cta tgc atc gat cat ttg caa      3681
Gly Leu Pro Gln His Leu Phe Glu Ser Leu Cys Ile Asp His Leu Gln
            80                  85                  90 cgc cac ggg gcc agc aaa aaa tcc att acc cgt gcg ttt gat gac gat      3729
Arg His Gly Ala Ser Lys Lys Ser Ile Thr Arg Ala Phe Asp Asp Asp
        95                  100                 105
```

-continued

| | | |
|---|---|---|
| gtt gag ttt cag gag cgc atg gca gaa cac atc cgg tac atg gtt gaa<br>Val Glu Phe Gln Glu Arg Met Ala Glu His Ile Arg Tyr Met Val Glu<br>110                     115                     120                     125 | | 3777 |
| acc att gct cac cac cag gtt gat att gat tca gag gta taa<br>Thr Ile Ala His His Gln Val Asp Ile Asp Ser Glu Val *<br>                          130                     135 | | 3819 |
| aacgagtaga agcttggctg ttttggcgga tgagagaaga ttttcagcct gatacagatt | | 3879 |
| aaatcagaac gcagaagcgg tctgataaaa cagaatttgc ctggcggcag tagcgcggtg | | 3939 |
| gtcccacctg accccatgcc gaactcagaa gtgaaacgcc gtagcgccga tggtagtgtg | | 3999 |
| gggtctcccc atgcgagagt agggaactgc caggcatcaa ataaaacgaa aggctcagtc | | 4059 |
| gaaagactgg gcctttcgtt ttatctgttg tttgtcggtg aacgctctcc tgagtaggac | | 4119 |
| aaatccgccg ggagcggatt tgaacgttgc gaagcaacgg cccggagggt ggcgggcagg | | 4179 |
| acgcccgcca taaactgcca ggcatcaaat taagcagaag gccatcctga cggatggcct | | 4239 |
| ttttgcgttt ctacaaactc ttttgtttat ttttctaaat acattcaaat atgtatccgc | | 4299 |
| tcatgagaca ataaccctga taaatgcttc aataatattg aaaaggaag agtatgagta | | 4359 |
| ttcaacattt ccgtgtcgcc cttattccct tttttgcggc attttgcctt cctgtttttg | | 4419 |
| ctcacccaga aacgctggtg aaagtaaaag atgctgaaga tcagttgggt gcacgagtgg | | 4479 |
| gttacatcga actggatctc aacagcggta agatccttga gttttcgc cccgaagaac | | 4539 |
| gttttccaat gatgagcact tttaaagttc tgctatgtgg cgcggtatta tcccgtgttg | | 4599 |
| acgccgggca agagcaactc ggtcgccgca tacactattc tcagaatgac ttggttgagt | | 4659 |
| actcaccagt cacagaaaag catcttacgg atggcatgac agtaagagaa ttatgcagtg | | 4719 |
| ctgccataac catgagtgat aacactgcgg ccaacttact tctgacaacg atcggaggac | | 4779 |
| cgaaggagct aaccgctttt ttgcacaaca tgggggatca tgtaactcgc cttgatcgtt | | 4839 |
| gggaaccgga gctgaatgaa gccataccaa acgacgagcg tgacaccacg atgcctgtag | | 4899 |
| caatggcaac aacgttgcgc aaactattaa ctggcgaact acttactcta gcttcccggc | | 4959 |
| aacaattaat agactggatg gaggcggata aagttgcagg accacttctg cgctcggccc | | 5019 |
| ttccggctgg ctggtttatt gctgataaat ctggagccgg tgagcgtggg tctcgcggta | | 5079 |
| tcattgcagc actggggcca gatggtaagc cctcccgtat cgtagttatc tacacgacgg | | 5139 |
| ggagtcaggc aactatggat gaacgaaata gacagatcgc tgagataggt gcctcactga | | 5199 |
| ttaagcattg gtaactgtca gaccaagttt actcatatat actttagatt gatttacgcg | | 5259 |
| ccctgtagcg gcgcattaag cgcggcgggt gtggtggtta cgcgcagcgt gaccgctaca | | 5319 |
| cttgccagcg ccctagcgcc cgctcctttc gctttcttcc cttcctttct cgccacgttc | | 5379 |
| gccggctttc cccgtcaagc tctaaatcgg ggctcccctt tagggttccg atttagtgct | | 5439 |
| ttacggcacc tcgaccccaa aaaacttgat ttgggtgatg gttcacgtag tgggccatcg | | 5499 |
| ccctgataga cggtttttcg ccctttgacg ttggagtcca cgttctttaa tagtggactc | | 5559 |
| ttgttccaaa cttgaacaac actcaaccct atctcgggct attcttttga tttataaggg | | 5619 |
| attttgccga tttcggccta ttggttaaaa atgagctgat ttaacaaaa atttaacgcg | | 5679 |
| aattttaaca aaatattaac gtttacaatt taaaggatc taggtgaaga tccttttga | | 5739 |
| taatctcatg accaaaatcc cttaacgtga gttttcgttc cactgagcgt cagacccgt | | 5799 |
| agaaaagatc aaaggatctt cttgagatcc tttttttctg cgcgtaatct gctgcttgca | | 5859 |
| aacaaaaaaa ccaccgctac cagcggtggt ttgtttgccg gatcaagagc taccaactct | | 5919 |
| ttttccgaag gtaactggct tcagcagagc gcagatacca aatactgtcc ttctagtgta | | 5979 |

-continued

```
gccgtagtta ggccaccact tcaagaactc tgtagcaccg cctacatacc tcgctctgct    6039
aatcctgtta ccagtggctg ctgccagtgg cgataagtcg tgtcttaccg ggttggactc    6099
aagacgatag ttaccggata aggcgcagcg gtcgggctga acgggggggtt cgtgcacaca    6159 gcccagcttg gagcgaacga cctacaccga actgagatac ctacagcgtg agctatgaga    6219
aagcgccacg cttcccgaag ggagaaaggc ggacaggtat ccggtaagcg cagggtcgg     6279 aacaggagag cgcacgaggg agcttccagg gggaaacgcc tggtatcttt atagtcctgt    6339
cgggtttcgc cacctctgac ttgagcgtcg attttttgtga tgctcgtcag ggggggcggag  6399 cctatggaaa aacgccagca acgcggcctt tttacggttc ctggccttttt gctggccttt  6459 tgctcacatg ttctttcctg cgttatcccc tgattctgtg gataaccgta ttaccgcctt   6519
tgagtgagct gataccgctc gccgcagccg aacgaccgag cgcagcgagt cagtgagcga   6579
ggaagcggaa gagcgcctga tgcggtattt tctccttacg catctgtgcg gtatttcaca   6639
ccgcataggg tcatggctgc gccccgacac ccgccaacac ccgctgacgc gccctgacgg   6699
gcttgtctgc tcccggcatc cgcttacaga caagctgtga ccgtctccgg gagctgcatg   6759
tgtcagaggt tttcaccgtc atcaccgaaa cgcgcgaggc agcaaggaga tggcgcccaa   6819
cagtcccccg gccacggggc ctgccaccat cccacgccg aaacaagcgc tcatgagccc    6879
gaagtggcga gcccgatctt ccccatcggt gatgtcggcg atataggcgc cagcaaccgc   6939
acctgtggcg ccggtgatgc cggccacgat gcgtccggcg tagaggatct gctcatgttt   6999
gacagcttat c                                                        7010
```

<210> SEQ ID NO 12
<211> LENGTH: 226
<212> TYPE: PRT
<213> ORGANISM: Artificial Sequence
<220> FEATURE:
<221> NAME/KEY: DOMAIN
<222> LOCATION: (1)..(226)
<223> OTHER INFORMATION: Red-alpha from plasmid pBAD-alpha-beta-gamma

<400> SEQUENCE: 12

```
Met Thr Pro Asp Ile Ile Leu Gln Arg Thr Gly Ile Asp Val Arg Ala
 1               5                  10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160
```

```
Ser Met Trp Val Thr Arg Lys Asn Ala Trp Tyr Phe Ala Asn Tyr Asp
            165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
            195                 200                 205

Lys Met Asp Glu Ala Leu Ala Glu Ile Gly Phe Val Phe Gly Glu Gln
            210                 215                 220

Trp Arg
225

<210> SEQ ID NO 13
<211> LENGTH: 261
<212> TYPE: PRT
<213> ORGANISM: Artificial Sequence
<220> FEATURE:
<221> NAME/KEY: DOMAIN
<222> LOCATION: (1)..(261)
<223> OTHER INFORMATION: Red-beta from plasmid pBAD-alpha-beta-gamma

<400> SEQUENCE: 13

Met Ser Thr Ala Leu Ala Thr Leu Ala Gly Lys Leu Ala Glu Arg Val
  1               5                  10                  15

Gly Met Asp Ser Val Asp Pro Gln Glu Leu Ile Thr Thr Leu Arg Gln
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
     50                  55                  60

Ala Phe Pro Asp Lys Gln Asn Gly Ile Val Pro Val Val Gly Val Asp
 65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
            115                 120                 125

Glu Pro Phe Lys Thr Arg Glu Gly Arg Glu Ile Thr Gly Pro Trp Gln
        130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
        195                 200                 205

Leu Ile Ala Leu Asp Lys Thr Trp Asp Asp Asp Leu Leu Pro Leu Cys
    210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
                245                 250                 255

Gln Lys Val Ala Ala
            260
```

```
-continued

<210> SEQ ID NO 14
<211> LENGTH: 138
<212> TYPE: PRT
<213> ORGANISM: Artificial Sequence
<220> FEATURE:
<221> NAME/KEY: DOMAIN
<222> LOCATION: (1)..(138)
<223> OTHER INFORMATION: Red-gamma from plasmid pBAD-alpha-beta-gamma
      and plasmid pBAD-ET-gamma

<400> SEQUENCE: 14

Met Asp Ile Asn Thr Glu Thr Glu Ile Lys Gln Lys His Ser Leu Thr
 1               5                  10                  15

Pro Phe Pro Val Phe Leu Ile Ser Pro Ala Phe Arg Gly Arg Tyr Phe
                20                  25                  30

His Ser Tyr Phe Arg Ser Ser Ala Met Asn Ala Tyr Tyr Ile Gln Asp
            35                  40                  45

Arg Leu Glu Ala Gln Ser Trp Ala Arg His Tyr Gln Gln Leu Ala Arg
        50                  55                  60

Glu Glu Lys Glu Ala Glu Leu Ala Asp Asp Met Glu Lys Gly Leu Pro
 65                  70                  75                  80

Gln His Leu Phe Glu Ser Leu Cys Ile Asp His Leu Gln Arg His Gly
                85                  90                  95

Ala Ser Lys Lys Ser Ile Thr Arg Ala Phe Asp Asp Asp Val Glu Phe
            100                 105                 110

Gln Glu Arg Met Ala Glu His Ile Arg Tyr Met Val Glu Thr Ile Ala
        115                 120                 125

His His Gln Val Asp Ile Asp Ser Glu Val
    130                 135
```